(12) United States Patent
Zeitlinger et al.

(10) Patent No.: US 10,287,628 B2
(45) Date of Patent: May 14, 2019

(54) METHODS AND KITS FOR IDENTIFYING POLYPEPTIDE BINDING SITES IN A GENOME

(71) Applicant: STOWERS INSTITUTE FOR MEDICAL RESEARCH, Kansas city, MO (US)

(72) Inventors: Julia Zeitlinger, Kansas City, MO (US); Qiye He, Shanghai (CN); Jeffrey Johnston, Kansas City, MO (US)

(73) Assignee: Stowers Institute for Medical Research, Kansas City, MO (US)

( * ) Notice: Subject to any disclaimer, the term of this patent is extended or adjusted under 35 U.S.C. 154(b) by 0 days.

(21) Appl. No.: 15/536,107

(22) PCT Filed: Dec. 18, 2015

(86) PCT No.: PCT/US2015/066861
§ 371 (c)(1),
(2) Date: Jun. 14, 2017

(87) PCT Pub. No.: WO2016/100911
PCT Pub. Date: Jun. 23, 2016

(65) Prior Publication Data
US 2017/0362650 A1    Dec. 21, 2017

Related U.S. Application Data

(60) Provisional application No. 62/094,937, filed on Dec. 19, 2014.

(51) Int. Cl.
| | | |
|---|---|---|
| C12Q 1/68 | (2018.01) | |
| C12Q 1/6869 | (2018.01) | |
| C12Q 1/6806 | (2018.01) | |
| C12Q 1/6853 | (2018.01) | |

(52) U.S. Cl.
CPC ......... *C12Q 1/6869* (2013.01); *C12Q 1/6806* (2013.01); *C12Q 1/6853* (2013.01); *C12Q 2535/122* (2013.01); *C12Q 2537/159* (2013.01); *C12Q 2563/179* (2013.01)

(58) Field of Classification Search
None
See application file for complete search history.

(56) References Cited

U.S. PATENT DOCUMENTS

2010/0323361 A1* 12/2010 Pugh .................... C12Q 1/6804
435/6.1

OTHER PUBLICATIONS

Huppertz et al. (Methods 65.3 (2014): 274-287) published online Oct. 25, 2013 (Year: 2014).*
Rhee et al.( Current protocols in molecular biology (2012): 21-24) (Year: 2012).*
International Search Report and Written Opinion of the ISA for PCT/US2015/066861.
Zinzen, R.P. et al. Computational models for neurogenic gene expression in the *Drosophila* embryo. Curr Biol 16, 1358-1365 (2006).
Huppertz, et al. iCLIP: Protein-RNA Interactions At Nucleotide Resolution. Methods. 25 1-12, 13/6, 13/10-12, Oct. 2013, vol. 65, pp. 274-287.
He, et al. ChIP-Nexus Protocol. Zeitlinger Lab. Jul. 2014, pp. 1-12.
Arnold, T. et al. 2008. The Use of Detergents to Purify Membrane Proteins. Current Protocols in Protein Science. 53:4.8.1-4.830.
Bardet, A.F. et al. Identification of transcription factor binding sites from ChIP-seq data at high resolution. Bioinformatics 29, 2705-2713 (2013).
Blackwood, E.M. et al. Max: a helix-loop-helix zipper protein that forms a sequence-specific DNA-binding complex with Myc. Science 251, 1211-1217 (1991).
Bohnuud, T. et al. Computational mapping reveals dramatic effect of Hoogsteen breathing on duplex DNA reactivity with formaldehyde. Nucleic Acids Research 40, 7644-7652 (2012).
Bonifacino, et al. 2001. Immunoprecipitation. Current Protocols in Immunology. 41:8.3.1-8.3.28.
Bystrykh LV (2012) Generalized DNA Barcode Design Based on Hamming Codes. PLoS ONE 7(5): e36852. doi:10.1371/journal.pone.0036852.
Casbon, J.A. et al. A method for counting PCR template molecules with application to next-generation sequencing. Nucleic Acids Research 39, e81 (2011).
Chen, F.E. et al. Crystal structure of p50/p65 heterodimer of transcription factor NF-kappaB bound to DNA. Nature 391, 410-413 (1998).
Evans, T. C. et al. 2008. DNA Repair Enzymes. Current Protocols in Molecular Biology. 84:3.9.1-3.9.12.
Fakhouri, W.D. et al. Deciphering a transcriptional regulatory code: modeling short-range repression in the *Drosophila* embryo. Mol Syst Biol 6, 341 (2010).
Feng, J. et al. Identifying ChIP-seq enrichment using MACS. Nat Protoc 7, 1728-1740 (2012).

(Continued)

*Primary Examiner* — Tracy Vivlemore
*Assistant Examiner* — Sahana S Kaup
(74) *Attorney, Agent, or Firm* — Bryan Cave Leighton Paisner LLP

(57) ABSTRACT

The present invention provides, inter alia, methods and kits for identifying where a polypeptide of interest binds in a genome. The methods include a) carrying out a chromatin immunoprecipitation coupled to exonuclease digestion (ChIP-exo) process with an antibody against the polypeptide of interest; (b) extracting a polynucleotide fragment to which the polypeptide of interest binds; (c) carrying out a library preparation protocol adapted from an individual nucleotide resolution UV cross-linking and immunoprecipitation (iCLIP) process on the ChIP-exo processed polynucleotide fragment; and (d) sequencing the resulting polynucleotides. The kits include: (a) reagents sufficient to carry out ChIP-exo; (b) reagents sufficient to carry out the library preparation protocol adapted from the iCLIP process; and (c) instructions for use.

28 Claims, 23 Drawing Sheets
Specification includes a Sequence Listing.

(56) References Cited

OTHER PUBLICATIONS

Ferre-D'Amare, A.R. et al. Recognition by Max of its cognate DNA through a dimeric b/HLH/Z domain. Nature 363, 38-45 (1993).
Gentleman, R.C. et al. Bioconductor: open software development for computational biology and bioinformatics. Genome Biology 5, R80 (2004).
Gordan, R. et al. Genomic regions flanking E-box binding sites influence DNA binding specificity of bHLH transcription factors through DNA shape. Cell Rep 3,1093-1104 (2013).
He, Q. et al. High conservation of transcriptional factor binding and evidence for combinatorial regulation across six *Drosophila* species. Nature Genetics 43, 414-420 (2011).
Hesselberth, J.R. et al. Global mapping of protein-DNA interactions in vivo by digital genomic footprinting. Nat Methods 6, 283-289 (2009).
Huang, J.D. et al. The interplay between multiple enhancer and silencer elements defines the pattern of decapentaplegic expression. Genes & Development 7, 694-704 (1993).
Ip, Y.T. et al. The dorsal gradient morphogen regulates strips of rhomboid expression in the presumptive neuroectoderm of the *Drosophila* embryo. Genes & Development 6, 1728-1739 (1992).
Ip, Y.T. et al. The dorsal morphogen is a sequence-specific DNA-binding protein that interacts with a long-range repression element in *Drosophila*. Cell 64, 439-446 (1991).
Kivioja, T. et al. Counting absolute numbers of molecules using unique molecular identifiers. Nat Methods 9, 72-74 (2012).
Konig, J. et al. iCLIP reveals the function of hnRNP particles in splicing at individual nucleotide resolution. Nat Struct Mol Biol 17, 909-915 (2010).
Langmead, B. et al. Ultrafast and memory-efficient alignment of short DNA sequences to the human genome. Genome Biology 10, R25 (2009).
Li, H. et al. The sequence alignment/Map format and SAMtools. Bioinformatics 25, 2078-2079 (2009).
Liu, X. et al. Whole-genome comparison of Leu3 binding in vitro and in vivo reveals the importance of nucleosome occupancy in target site selection. Genome Research 16, 1517-1528 (2006).
Martin, M. Cutadapt removes adaptor sequences from high-throughput sequencing reads. EMBnet.journal 17, 3 (2011).
Mir, K. et al. Short Barcodes for Next Generation Sequencing. PloS one 8.12 (2013): e82933.
Nair, S.K. et al. X-ray structures of Myc-Max and Mad-Max recognizing DNA. Molecular bases of regulation by proto-oncogenic transcription factors. Cell 112, 193-205 (2003).
Orian, A. et al. Genomic binding by the *Drosophila* Myc, Max, Mad/Mnt transcription factor network. Genes & Development 17, 1101-1114 (2003).

Orlando, V. Mapping chromosomal proteins in vivo by formaldehyde-crosslinked-chromatin immunoprecipitation. Trend Biochem Sci 25, 99-104 (2000).
Ozdemir, A. et al. High resolution mapping of Twist to DNA in *Drosophila* embryos: Efficient functional analysis and evolutionary conservation. Genome Res 21, 566-577 (2011).
Prendergast, G.C. et al. Association of Myn, the murine homolog of max with c-Myc stimulates methylation-sensitive DNA binding and ras cotransformation. Cell 65, 395-407 (1991).
Rhee, H.S. et al. ChIP-exo method for identifying genomic location of DNA-binding proteins with near-single-nucleotide accuracy. Curr Protoc Mol Biol Chapter 21, Unit 21 24 (2012b).
Rhee, H.S. et al. Comprehensive genome-wide protein-DNA interactions detected at single-nucleotide resolution. Cell 147, 1408-1419 (2011).
Rhee, H.S. et al. Genome-wide structure and organization of eukaryotic pre-initiation complexes. Nature 483, 295-301 (2012a).
Sandmann, T et al. A core transcriptional network for early mesoderm development in *Drosophila melanogaster*. Genes & Development 21, 436-449 (2007).
Serandour, A.A. et al. Development of an Illumina-based ChIP-exonuclease method provides insight into FoxA1-DNA binding properties. Genome Biology 14, R147 (2013).
Spitz, F. et al. Transcription factors: from enhancer binding to developmental control. Nat Rev Genet 13, 613-626 (2012).
Szymanski, P. et al. Multiple modes of dorsal-bHLH transcriptional synergy in the *Drosophila* embryo. Embo J 14, 2229-2238 (1995).
Thompson, J. F. et al. 2010. Single Molecule Sequencing with a HeliScope Genetic Analysis System. Current Protocols in Molecular Biology. 92:7.10.1-7.10.14.
Venters, B.J. et al. Genomic organization of human transcription initiation complexes. Nature 502, 53-58 (2013).
Walhout, A.J. et al. c-Myc/Max heterodimers bind cooperatively to the E-box sequences located in the first intron of the rat ornithine decarboxylase (ODC) gene. Nucleic Acids Research 25, 1493-1501 (1997).
Wechsler, D.S. et al. Differential binding of c-Myc and Max to nucleosomal DNA. Molecular and Cellular Biology 14, 4097-4107 (1994).
White, M.A. et al. Massively parallel in vivo enhancer assay reveals that highly local features determine the cis-regulatory function of ChIP-seq peaks. PNAS 110, 11952-11957 (2013).
Zeitlinger, J. et al. Whole-genome ChIP-chip analysis of Dorsal, Twist, and Snail suggest integration of diverse patterning processes in the *Drosophila* embryo. Genes & Development 21, 385-390 (2007).
Zhou, T. et al. DNAshape: a method for the high-throughput prediction of DNA structural features on a genomic scale. Nucleic Acids Research 41, W56-62 (2013).
Zhu, L.J. et al. FlyFactorSurvey: a database of *Drosophila* transcription factor binding specificities determined using the bacterial one-hybrid system. Nucleic Acids Res 39, D111-117 (2011).

* cited by examiner

FIG. 2, Con't
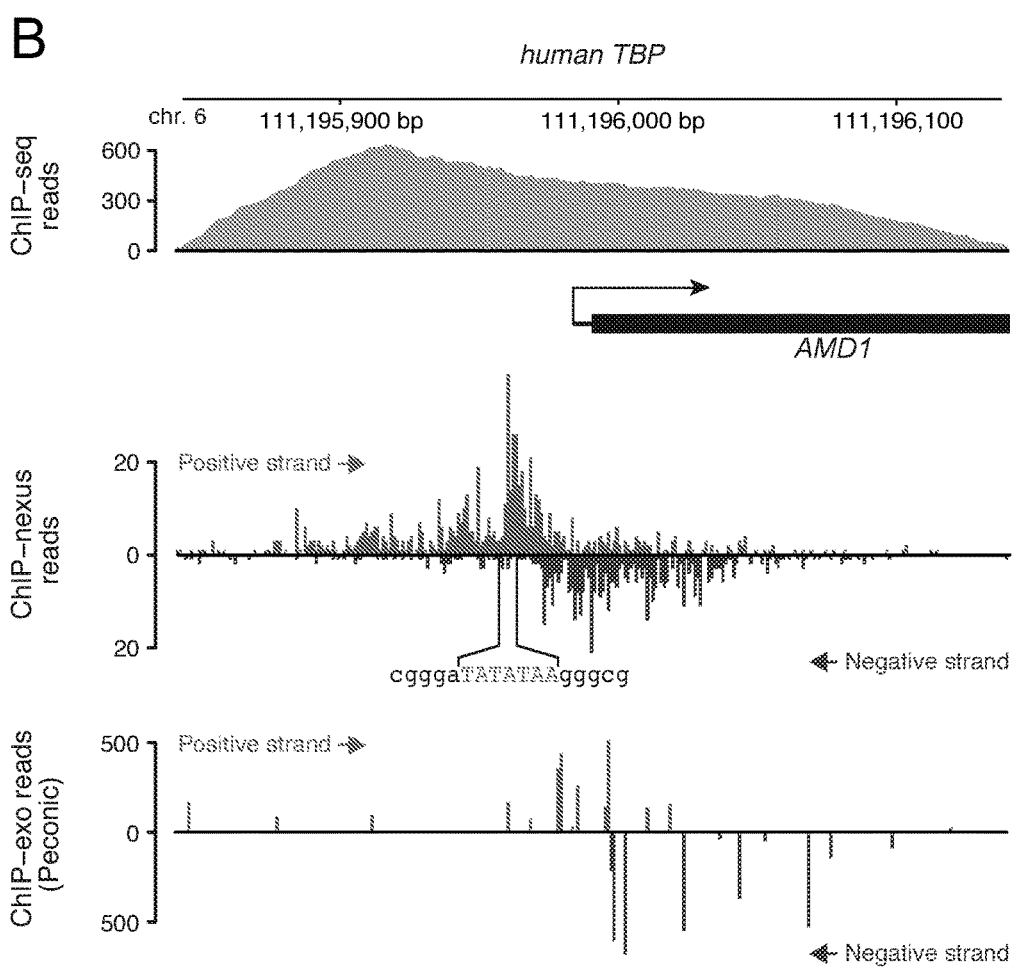

FIG. 2, Con't
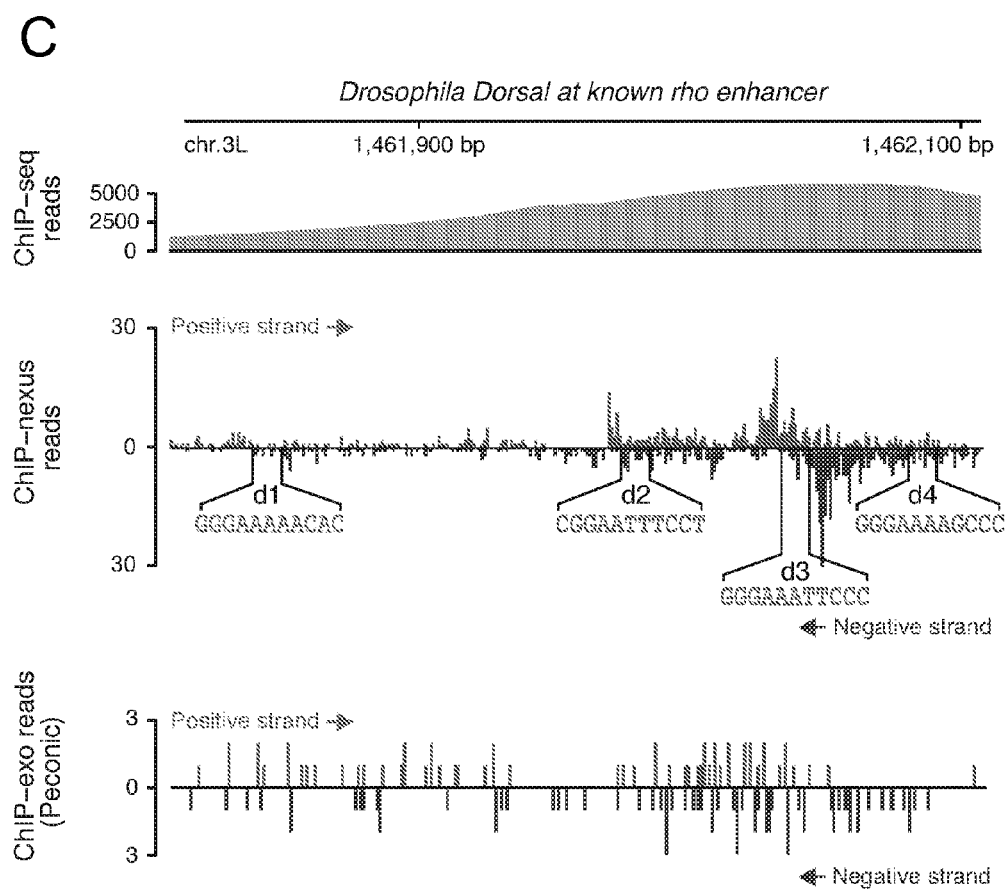

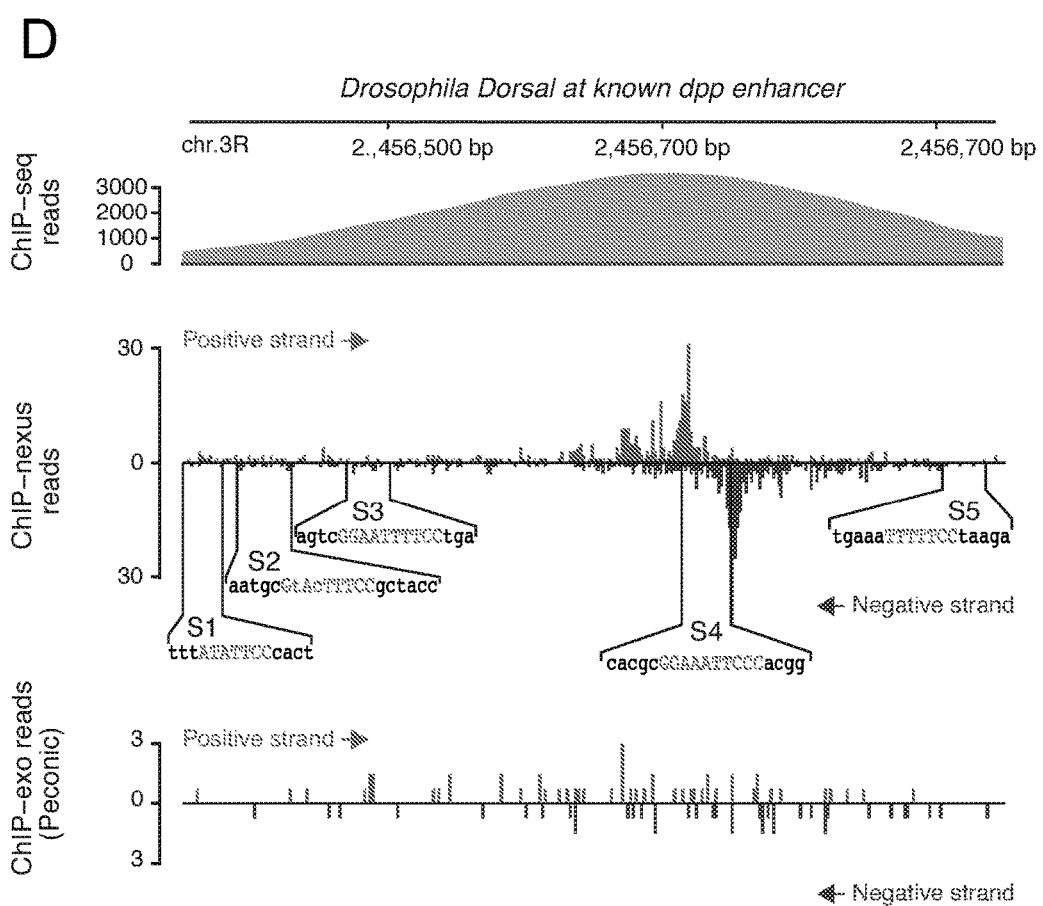
FIG. 2, Con't

FIG. 2, Con't
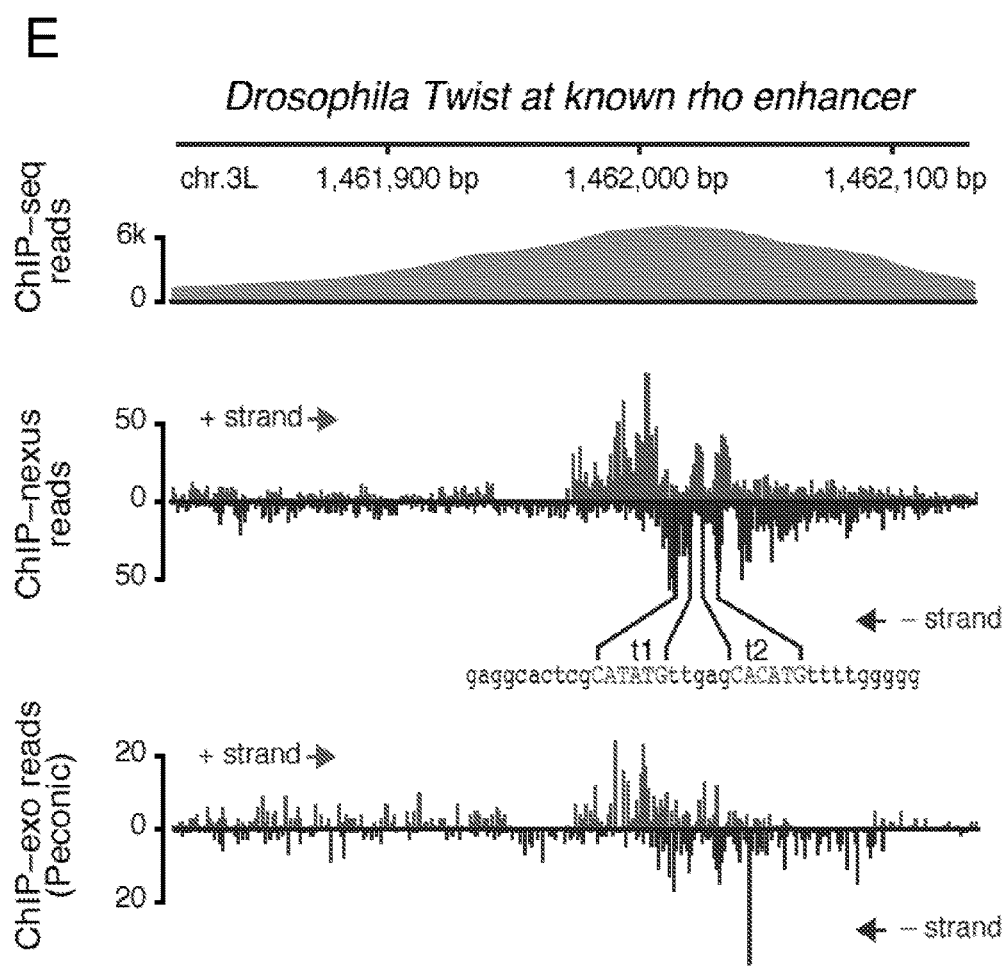

FIG. 4, Con't
B
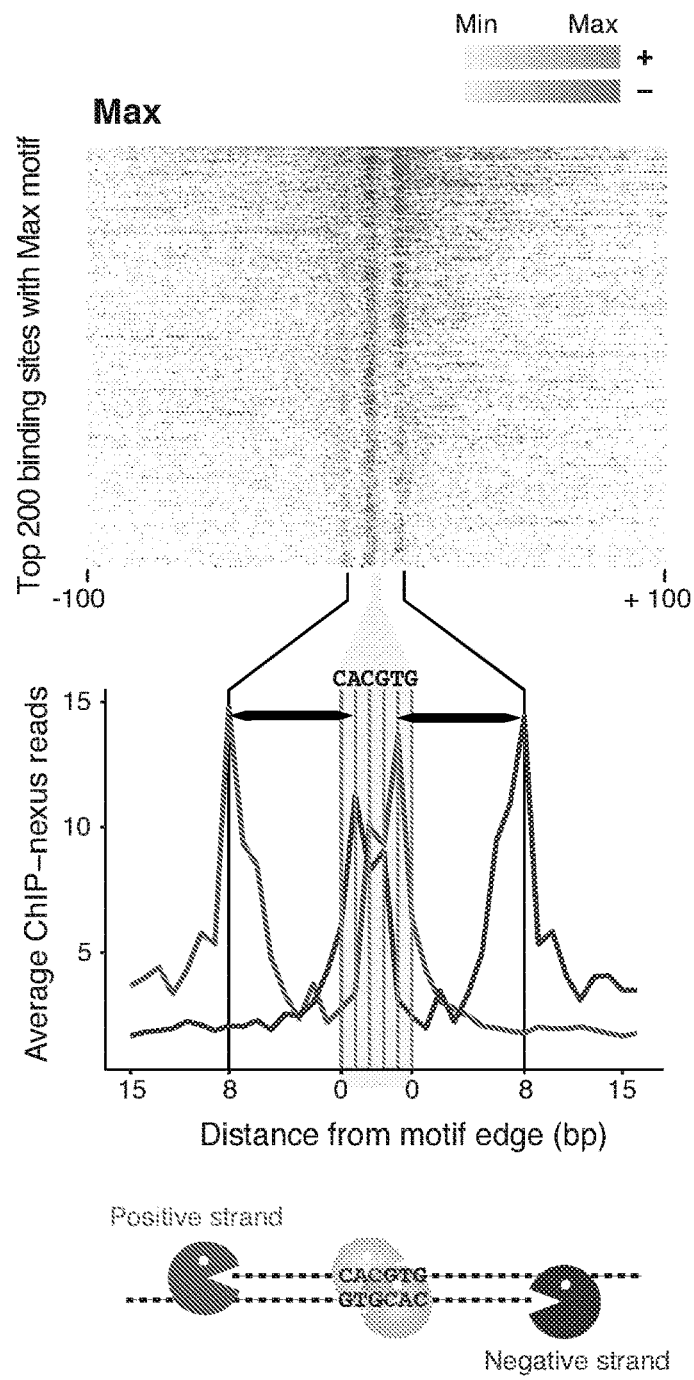

FIG. 4, Con't
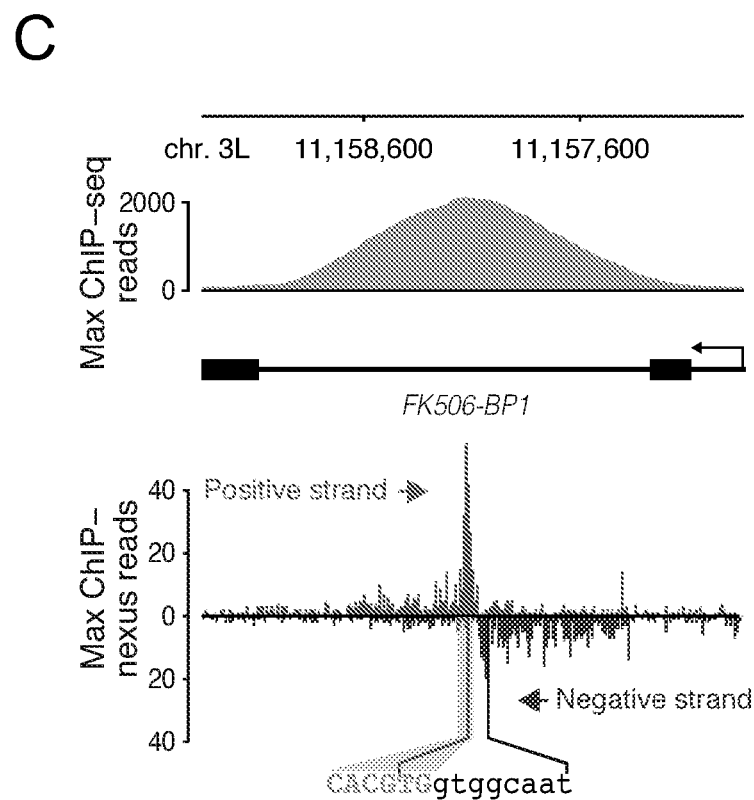

FIG. 4, Con't
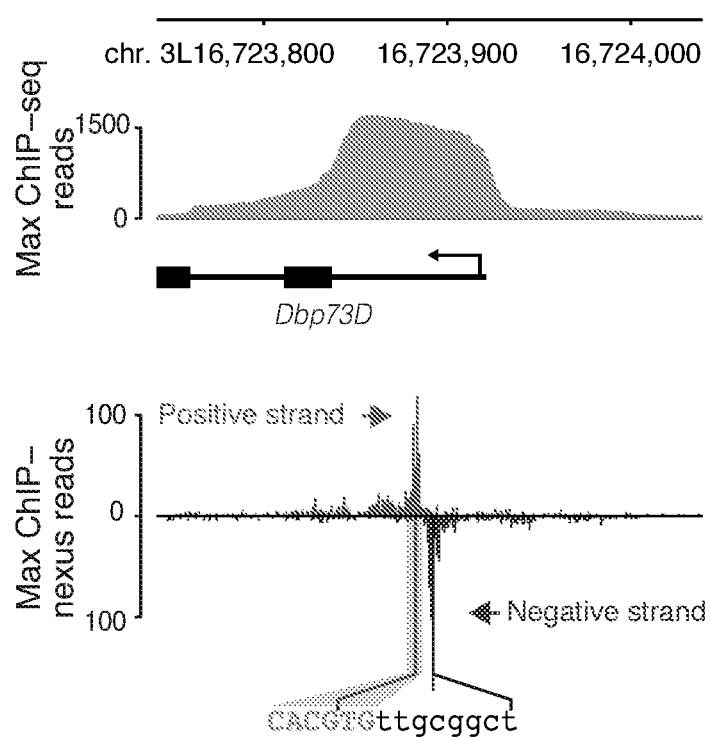

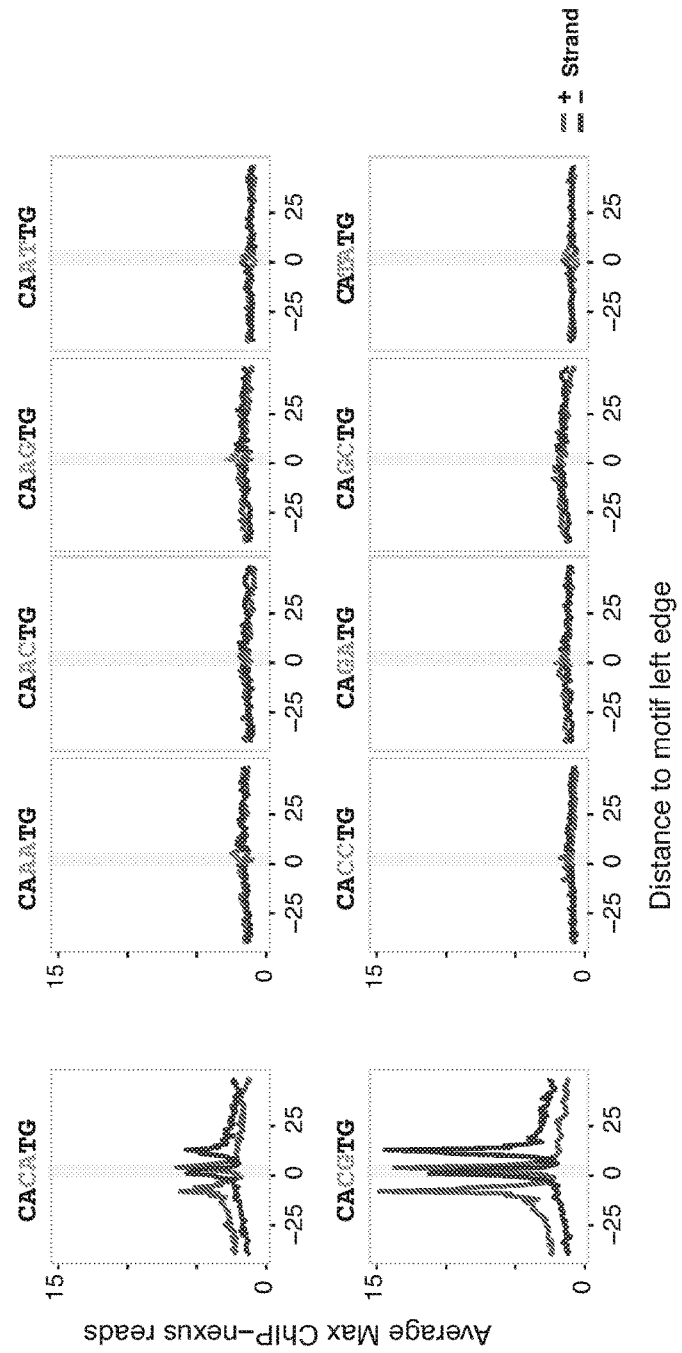
FIG. 4, Con't

FIG. 4, Con't
F
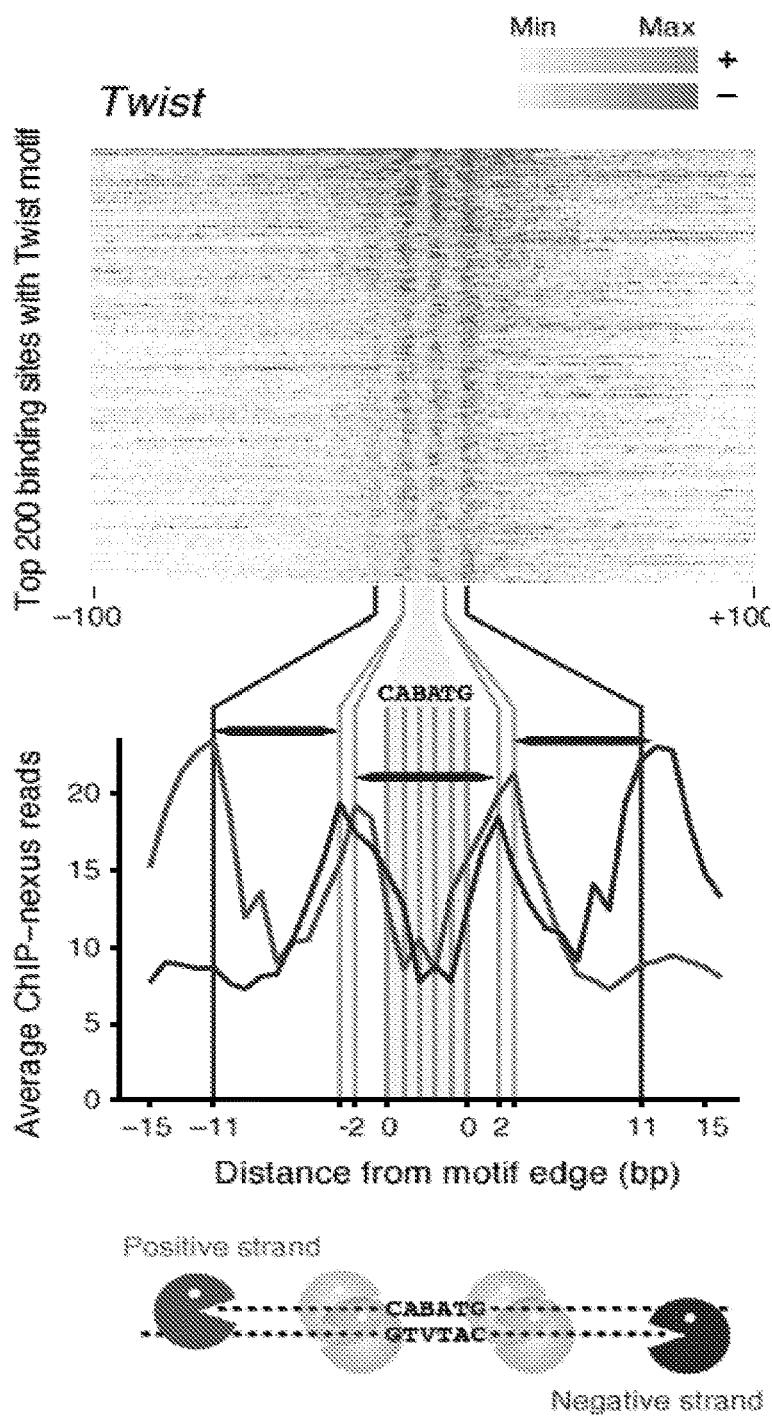

FIG. 4, Con't
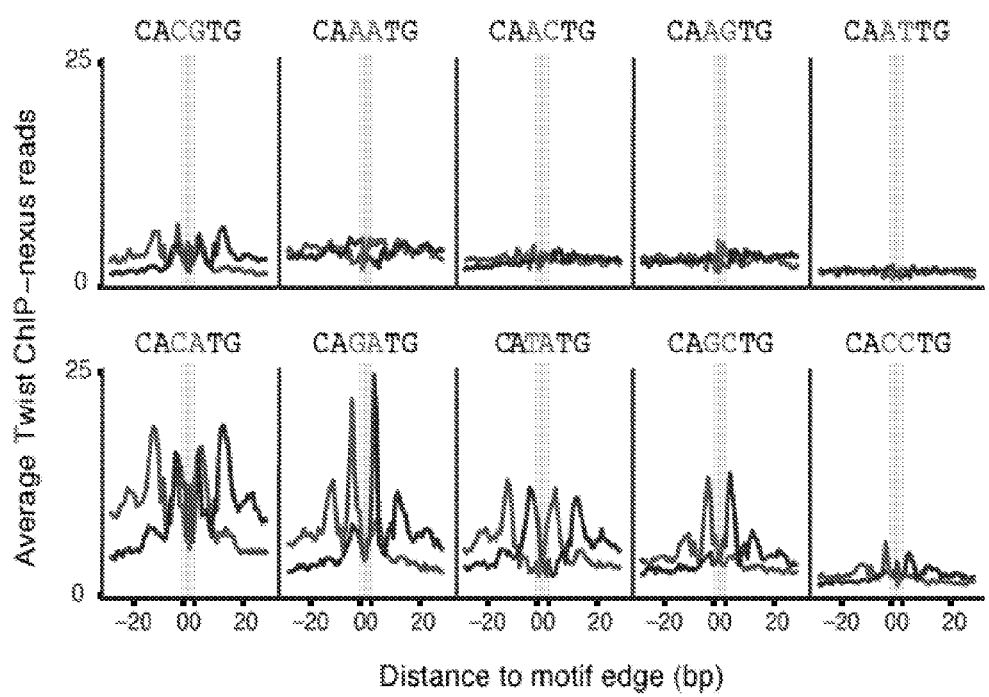

FIG. 5, Con't
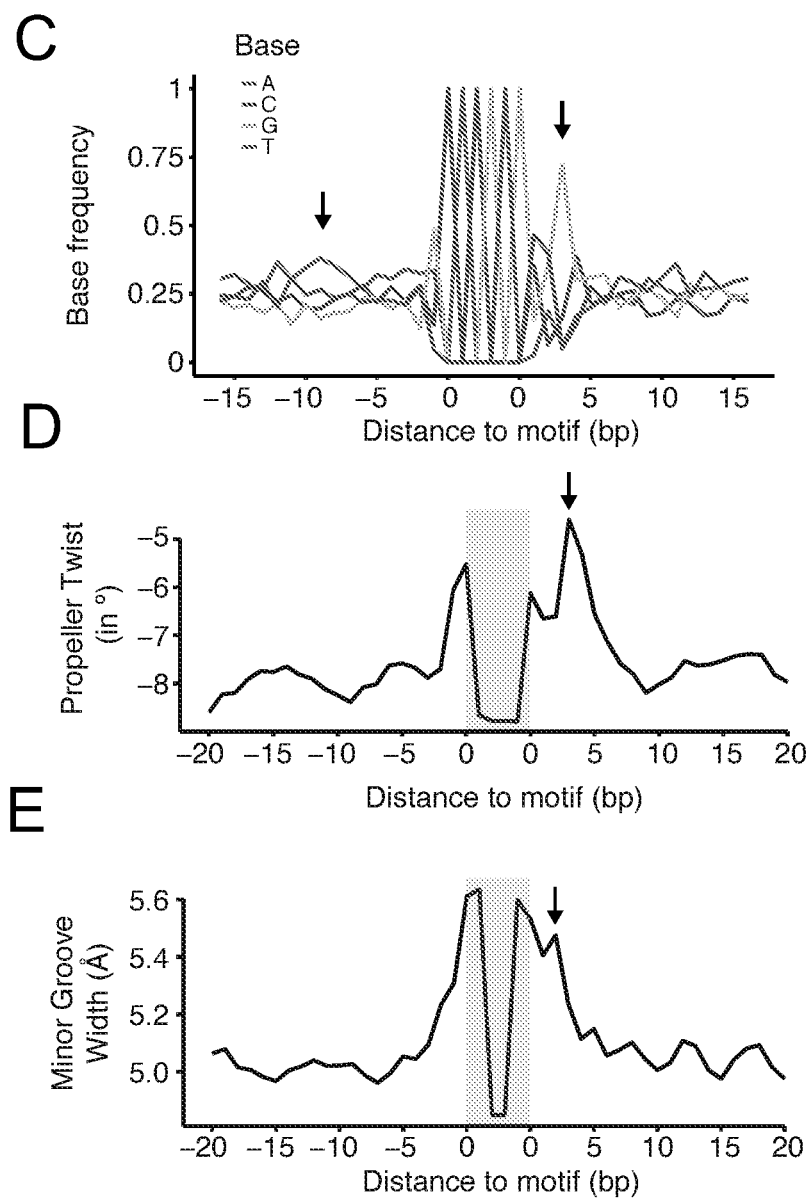

FIG. 5, Con't
F
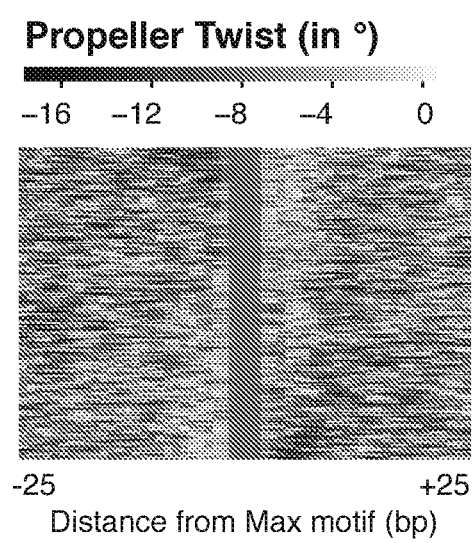
Propeller Twist (in °)
−16  −12  −8  −4  0
−25                              +25
Distance from Max motif (bp)
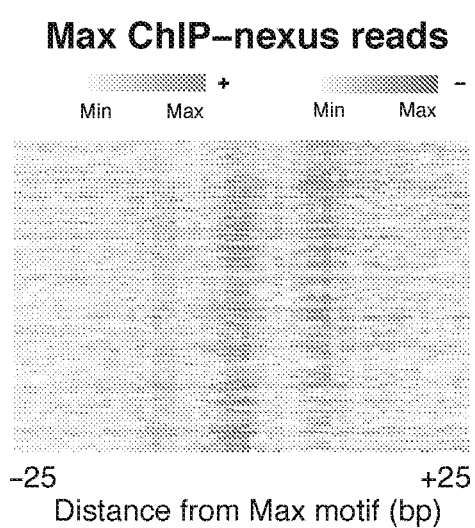
Max ChIP-nexus reads
+                       −
Min   Max      Min   Max
−25                              +25
Distance from Max motif (bp)

FIG. 7, Con't
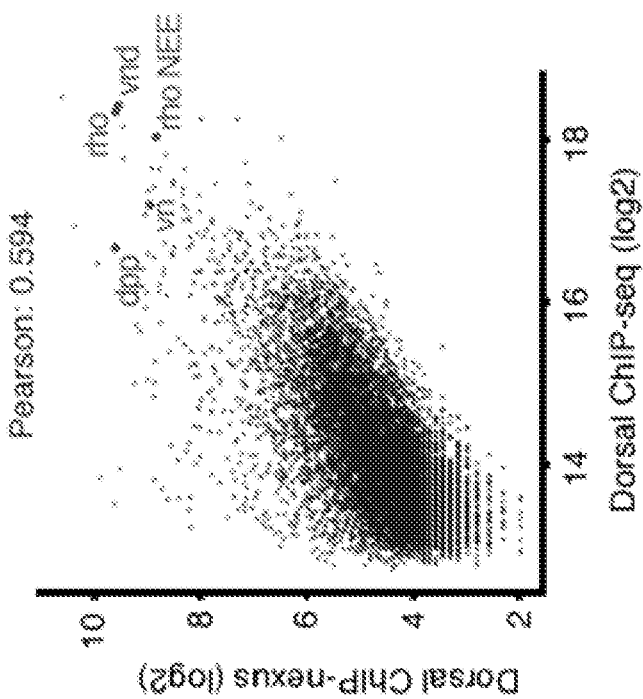
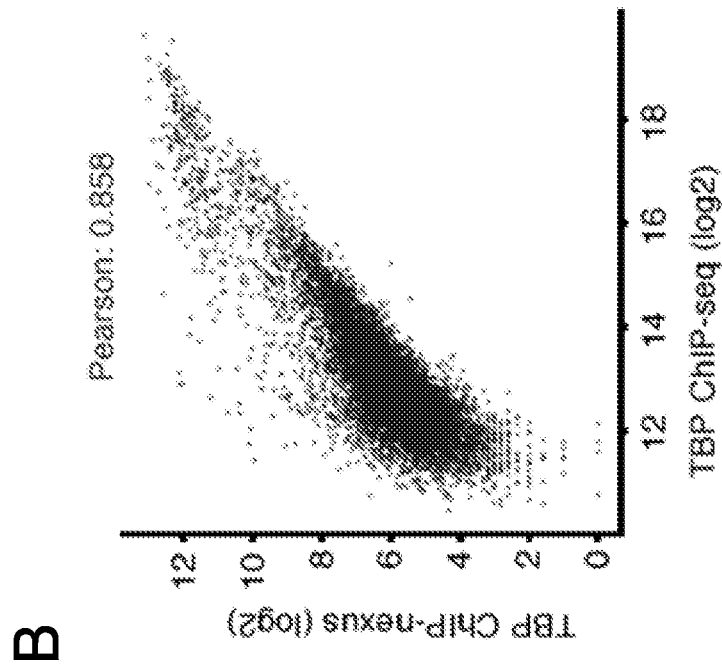

FIG. 7, Con't
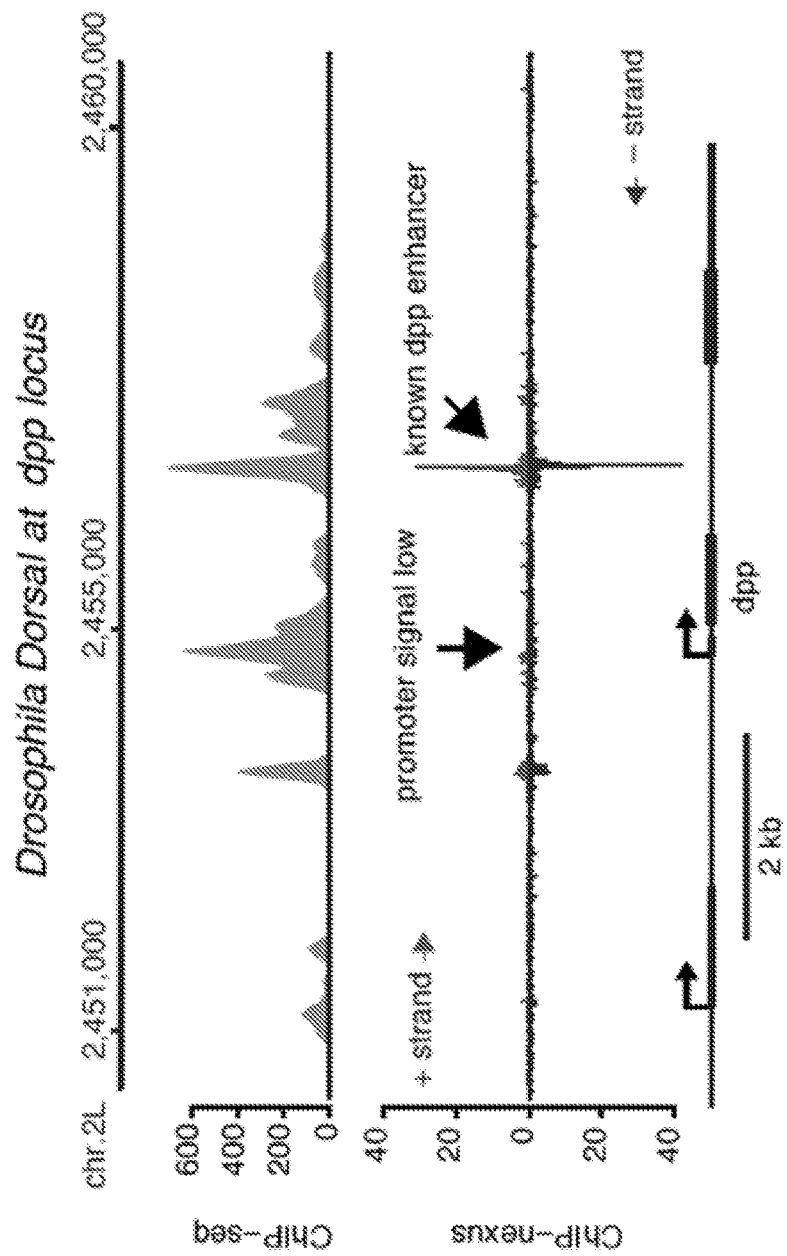

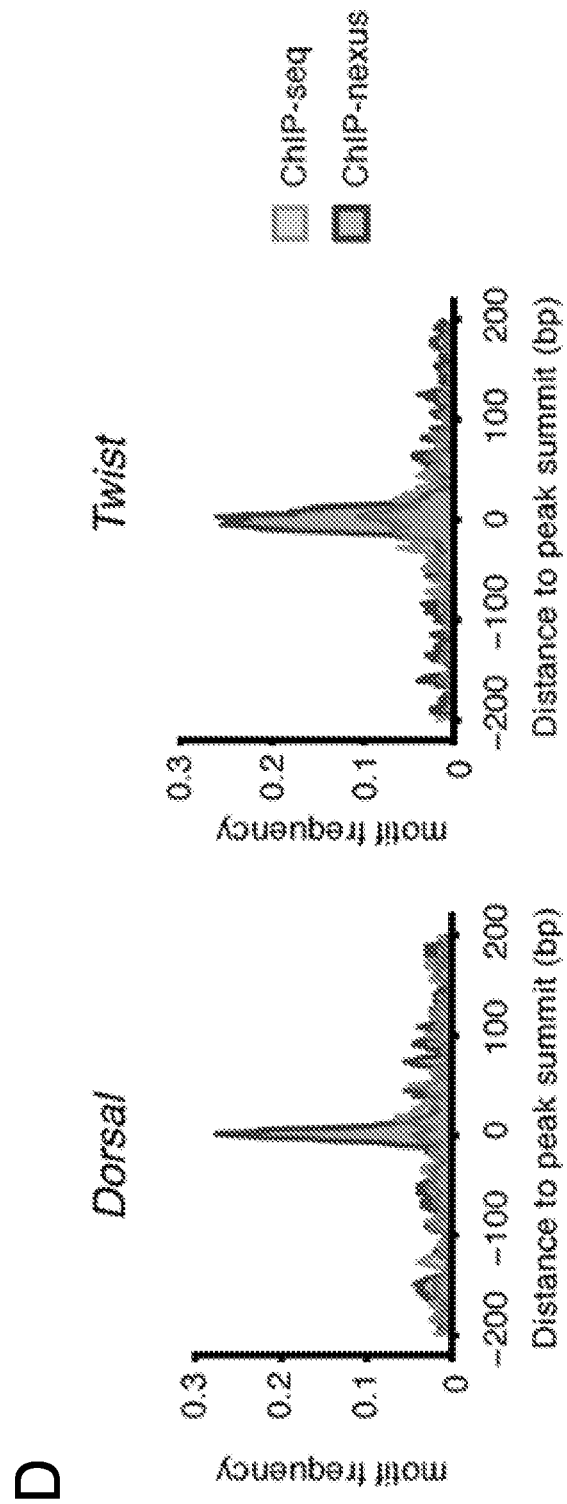
FIG. 7, Con't

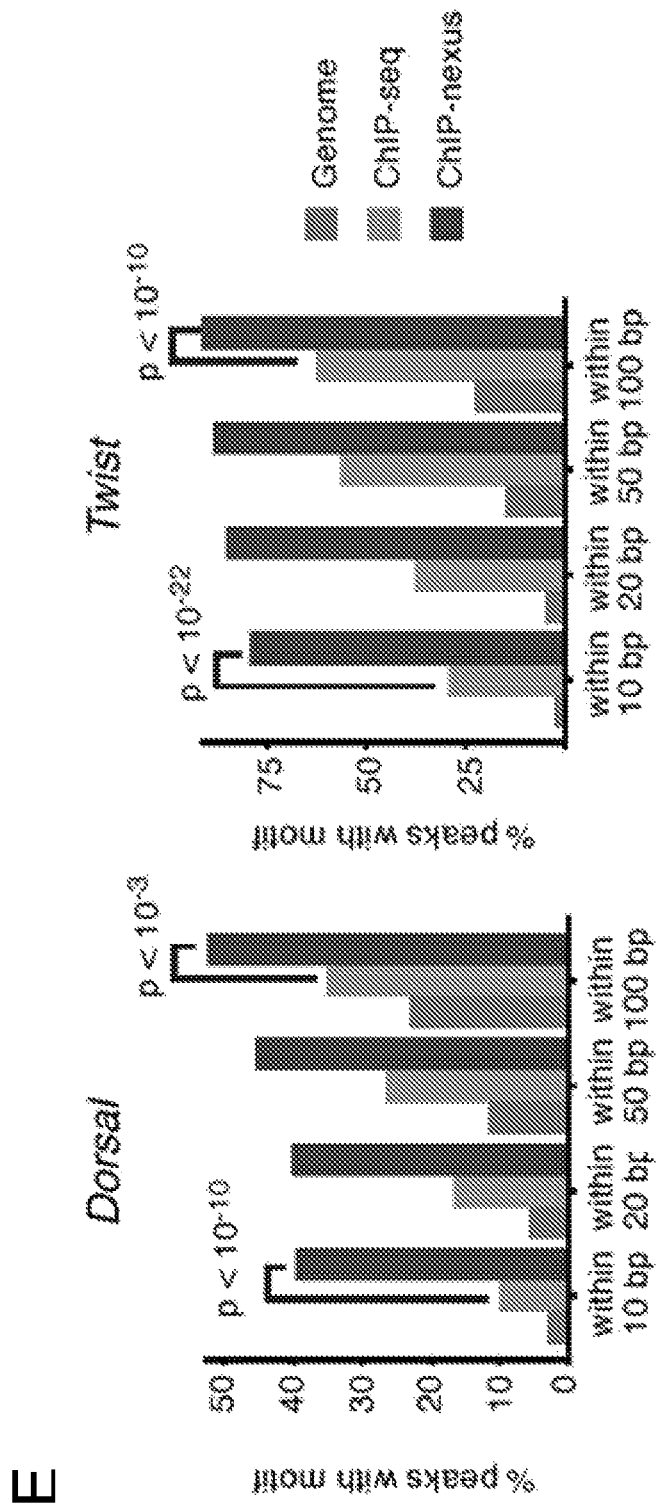
FIG. 7, Con't

SEQUENCE LISTING

```
<160> NUMBER OF SEQ ID NOS: 10

<210> SEQ ID NO 1
<211> LENGTH: 39
<212> TYPE: DNA
<213> ORGANISM: Artificial sequence
<220> FEATURE:
<223> OTHER INFORMATION: Synthetic sequence

<400> SEQUENCE: 1
gatcggaaga gcacacgtct ggatccacga cgctcttcc                          39

<210> SEQ ID NO 2
<211> LENGTH: 54
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<222> LOCATION: (5)..(9)
<223> OTHER INFORMATION: n is a, c, g, or t

<400> SEQUENCE: 2
tcagnnnnna gatcggaaga gcgtcgtgga tccagacgtg tgctcttccg atct         54

<210> SEQ ID NO 3
<211> LENGTH: 25
<212> TYPE: DNA
<213> ORGANISM: Artificial sequence
<220> FEATURE:
<223> OTHER INFORMATION: Synthetic sequence

<400> SEQUENCE: 3
gaagagcgtc gtggatccag acgtg                                         25
```

<210> SEQ ID NO 4
<211> LENGTH: 58
<212> TYPE: DNA
<213> ORGANISM: Artificial sequence
<220> FEATURE:
<223> OTHER INFORMATION: Synthetic sequence

<400> SEQUENCE: 4
aatgatacgg cgaccaccga gatctacact ctttccctac acgacgctct tccgatct         58

<210> SEQ ID NO 5
<211> LENGTH: 64
<212> TYPE: DNA
<213> ORGANISM: Artificial sequence
<220> FEATURE:
<223> OTHER INFORMATION: Synthetic sequence

<400> SEQUENCE: 5
caagcagaag acggcatacg agatcgtgat gtgactggag ttcagacgtg tgctcttccg         60
atct                                                                      64

<210> SEQ ID NO 6
<211> LENGTH: 64
<212> TYPE: DNA
<213> ORGANISM: Artificial sequence
<220> FEATURE:
<223> OTHER INFORMATION: Synthetic sequence

<400> SEQUENCE: 6
caagcagaag acggcatacg agatacatcg gtgactggag ttcagacgtg tgctcttccg         60
atct                                                                      64

<210> SEQ ID NO 7
<211> LENGTH: 64
<212> TYPE: DNA
<213> ORGANISM: Artificial sequence
<220> FEATURE:
<223> OTHER INFORMATION: Synthetic sequence

<400> SEQUENCE: 7
caagcagaag acggcatacg agatgcctaa gtgactggag ttcagacgtg tgctcttccg         60
atct                                                                      64

<210> SEQ ID NO 8
<211> LENGTH: 64
<212> TYPE: DNA
<213> ORGANISM: Artificial sequence
<220> FEATURE:
<223> OTHER INFORMATION: Synthetic sequence

<400> SEQUENCE: 8
caagcagaag acggcatacg agattggtca gtgactggag ttcagacgtg tgctcttccg         60
atct                                                                      64

<210> SEQ ID NO 9
<211> LENGTH: 64
<212> TYPE: DNA
<213> ORGANISM: Artificial sequence
<220> FEATURE:
<223> OTHER INFORMATION: Synthetic sequence

```
<400> SEQUENCE: 9
caagcagaag acggcatacg agatcactgt gtgactggag ttcagacgtg tgctcttccg    60
atct                                                                64

<210> SEQ ID NO 10
<211> LENGTH: 64
<212> TYPE: DNA
<213> ORGANISM: Artificial sequence
<220> FEATURE:
<223> OTHER INFORMATION: Synthetic sequence

<400> SEQUENCE: 10
caagcagaag acggcatacg agatattggc gtgactggag ttcagacgtg tgctcttccg    60
atct                                                                64
```

METHODS AND KITS FOR IDENTIFYING POLYPEPTIDE BINDING SITES IN A GENOME

CROSS-REFERENCES TO RELATED APPLICATIONS

The present application is the National Stage of International Application No. PCT/US2015/066861, filed on Dec. 18, 2015 which claims benefit to U.S. Provisional Application No. 62/094,937, filed Dec. 19, 2014. The entire contents of the above applications are incorporated by reference as if recited in full herein.

GOVERNMENT FUNDING

This invention was made with government support under grant no. 1DP2 OD004561-01 from the National Institutes of Health. The government has certain rights in the invention.

FIELD OF INVENTION

The present invention provides, inter alia, methods and kits for identifying where a polypeptide of interest binds in the genome.

INCORPORATION BY REFERENCE OF SEQUENCE LISTING

This application contains references to amino acids and/or nucleic acid sequences that have been filed concurrently herewith as sequence listing text file 0367335pct.txt, file size of 2.67 KB, created on Dec. 17, 2015. The aforementioned sequence listing is hereby incorporated by reference in its entirety pursuant to 37 C.F.R. § 1.52(e)(5).

BACKGROUND OF THE INVENTION

To understand the mechanisms of combinatorial control by transcription factors (Spitz et al., 2012), it was reasoned that an important contribution would be the ability to precisely map transcription factor binding footprints in vivo at a single nucleotide resolution. The occupancy of specific transcription factors can be mapped by chromatin immunoprecipitation (ChIP) coupled to deep sequencing (ChIP-seq), but the resolution of this technique is limited since a minimal DNA fragment size is required for unique alignment to the genome (Bardet et al., 2013). In an improvement to ChIP-seq called ChIP-exo, the immunoprecipitated chromatin fragments are digested by lambda exonuclease, which digests one strand of the double stranded DNA (dsDNA) in a 5'-to-3' direction and stops when it encounters a cross-linked protein. In this manner, the exact bases bordering a DNA-bound protein (the 'stop bases') may be accurately and uniquely mapped, revealing the binding footprint of a protein at essentially nucleotide resolution.

ChIP-exo has proven to be a very powerful technique and has revealed interesting insights into the binding of transcription factors and chromatin remodeling factors (Venters et al., 2013, Rhee et al., 2012a, Rhee et al., 2012b). However, there are technical hurdles in establishing and applying the technique to biological problems. Notably, the additional wash and digestion steps in ChIP-exo produce lower amounts of DNA as compared to conventional ChIP-seq experiments. The amount of recovered DNA fragments, however, is critical for the quality of a ChIP library. For amplification during library preparation, DNA fragments have to successfully complete two inefficient ligation steps in order to acquire adaptors on both of their ends (Rhee et al., 2012b, Rhee et al., 2011). Low amounts of starting DNA often lead to over-amplification artifacts during PCR, producing noisy data that are not reproducible (Kivioja et al., 2012, Casbon et al., 2011). The original ChIP-exo protocol was designed for a particular platform—the SOLiD platform—it would be beneficial to have a protocol that works with other platforms, such as, e.g., Illumina-based platforms. (See, e.g., Venters et al., 2013, Serandour et al., 2013). The present invention is directed to meeting the above-identified and other needs and that has high robustness and reproducibility, even with transcription factors whose ChIP experiments typically yield low amounts of DNA.

SUMMARY OF THE INVENTION

One embodiment of the present invention is a method for identifying where a polypeptide of interest binds in a genome. The method comprises:
 (a) carrying out a chromatin immunoprecipitation coupled to an exonuclease digestion (ChIP-exo) process with an antibody against the polypeptide of interest;
 (b) extracting a polynucleotide fragment to which the polypeptide of interest binds;
 (c) carrying out a library preparation protocol adapted from an individual nucleotide resolution UV cross-linking and immunoprecipitation (iCLIP) process on the ChIP-exo processed polynucleotide fragment; and
 (d) sequencing the resulting polynucleotides.

Another embodiment of the present invention is a method for identifying where a polypeptide of interest binds in a genome. The method comprises:
 (a) immunoprecipitating the polypeptide of interest which is cross-linked to a polynucleotide fragment using an antibody linked to a substrate;
 (b) ligating an adaptor to the polynucleotide fragment, which adaptor comprises two tail-to-tail primer sequences, a restriction site, and a polynucleotide barcode, which barcode protrudes as a 5' end overhang to prevent ligation to the barcode optionally followed by a washing step;
 (c) filling in the 5' overhang to copy the barcode and generate blunt ends for exonuclease digestion;
 (d) digesting the blunt-ended polynucleotide fragment from step (c) with an exonuclease, which terminates digestion of the polynucleotide upon encountering a physical barrier caused by the polypeptide (stop base);
 (e) extracting the single-stranded polynucleotide fragment produced by the exonuclease digestion from step (d) and purifying a single-stranded polynucleotide;
 (f) self-circularizing the single-stranded polynucleotide from step (e) to place the barcode adjacent to the stop base;
 (g) contacting the circularized polynucleotide with (1) an oligonucleotide designed to produce localized double-stranded DNA around the restriction site in the adaptor and (2) a restriction enzyme that recognizes and cleaves the circularized polynucleotide at the restriction site in the adaptor to re-linearize the polynucleotide fragment, wherein upon relinearization the polynucleotide fragment comprises a primer sequence at each end; and
 (h) amplifying the polynucleotide sequence to an extent sufficient for sequencing.

A further embodiment of the present invention is a kit for carrying out any of the methods disclosed herein together with instructions for its use.

An additional embodiment of the present invention is a kit for identifying where a polypeptide of interest binds in a genome. The kit comprising:
  (a) reagents sufficient to carry out ChIP-exo;
  (b) reagents sufficient to carry out a library preparation protocol adapted from an iCLIP process; and
  (c) instructions for use.

Another embodiment of the present invention is a kit for identifying where a polypeptide of interest binds in a genome. The kit comprising:
  (a) reagents to wash chromatin;
  (b) reagents for carrying out end repair;
  (c) reagents for carrying out dA tailing;
  (d) an adaptor;
  (e) reagents for ligating the adaptor to the chromatin;
  (f) reagents for filling in 5' overhang in the chromatin caused by the adaptor;
  (g) reagents for end trimming;
  (h) reagents for carrying out 5'-3' double-stranded-specific exonuclease digestion;
  (i) reagents for carrying out 5'-3' single-stranded-specific exonuclease digestion;
  (j) reagents for carrying out self-circularization of single stranded polynucleotide sequence;
  (k) reagents for re-linearizing the circular polynucleotide sequence; and
  (l) reagents for carrying out PCR amplification of the re-linearized polynucleotide sequence.

BRIEF DESCRIPTION OF THE DRAWINGS

FIGS. 2A and 2B show TATA Box Binding Protein (TBP) profiles in human K562 cells (2A) at the RPS12 promoter and (2B) the AMD1 promoter. While ChIP-nexus and ChIP-exo generally agree on TBP binding footprints, ChIP-nexus provides better coverage and richer details than ChIP-exo, which shows signs of over-amplification because large numbers of reads accumulate at a few discreet bases. FIG. 2C shows Dorsal profiles at the well-characterized *D. melanogaster* rhomboid (rho) enhancer. Four Dorsal binding sites (d1-d4) were previously mapped by in vitro DNase footprinting (Ip et al., 1992). Note that ChIP-nexus identifies d3 as the strong dorsal binding site in vivo, consistent with experimental data and computational modeling (Fakhouri et al., 2010). In contrast, ChIP-exo did not detect any obvious Dorsal footprint within the enhancer, probably due to the low coverage yield from the SOLiD sequencing platform utilized in this protocol. FIG. 2D shows Dorsal profiles at the decapentaplegic (dpp) enhancer. Five "strong" dorsal binding sites (S1-S5) were previously mapped by in vitro DNase footprinting (Huang et al., 1993). Note that ChIP-nexus identifies S4 as the only binding site with significant dorsal binding in vivo. At the same time, ChIP-exo did not detect any clear Dorsal footprint within the enhancer. FIG. 2E shows Twist profiles at the same rho enhancer. Note that ChIP-nexus shows strong Twist footprints surrounding the two Twist binding sites (t1, t2) (Ip et al., 1992). In this case, ChIP-exo performed by Peconic identified a similar Twist footprint. This shows that the Peconic experiments, which were performed with the same chromatin extracts as the Dorsal experiments, worked in principle but were less robust than our ChIP-nexus experiments.

FIG. 4A shows the ChIP-nexus footprints of Dorsal (NFkB) extending beyond the canonical motif. The top 200 dorsal motifs (GGRWWTTCC with up to one mismatch) were selected and ordered based on the highest ChIP-nexus signal. The footprints show a consistent boundary on the positive strand (red) and negative strand (blue) around each motif (heatmap). The zoomed-in average profile below reveals that the footprint extends, on average, 5 bp away from the motif edge. The horizontal black bar denotes the average dorsal footprint, and the pacman symbols represent lambda exonuclease. FIG. 4B shows the Max ChIP-nexus footprints have outside boundaries in addition to signal inside the motif. Similar to FIG. 4A, the top 200 Max E-box motifs (CACGTG, no mismatch) were selected and ordered based on highest ChIP-nexus signal. The zoomed-in average profile shows a consistent outside boundary 8 base pairs upstream of the motif but also another boundary at the A/T base within the E-box motif, suggesting two separate footprints (black bars). The digestion pattern is drawn schematically below using Pacman symbols. FIGS. 4C and 4D show examples of the Max ChIP-nexus footprints showing that the Max profile indeed consists of two separate footprints, one of which is frequently dominant, like the one shown here in FIG. 4C in the Fk506-BP1 intron and FIG. 4D near the Dbp73D promoter. FIG. 4E shows average Max ChIP-nexus footprint at the top 200 sites for all possible E-box variants (CANNTG). Note that each variant profile includes its reverse complement. The results show that the CACGTG profile is the dominant in vivo binding sequence. The CACATG is also bound at lower levels but with the same average footprint, suggesting that the Max footprint pattern is not dependent on the E-box sequence. FIG. 4F shows that the Twist ChIP-nexus footprint on the E-box motif CABATG (no mismatch) has two outside boundaries, one at 11 bp, and one at 2 bp away from the motif edge, suggesting interactions with flanking DNA sequences. Each portion of the footprint is around 8-9 bp long (horizontal black bar). FIG. 4G shows Twist binding specificity and a complex footprint shape. Notably, the outer boundary at −11 bp is stronger at the CATATG and CACATG motif, whereas the inner boundary at −2 bp is stronger at the CAGATG motif.

FIG. 5A shows average Max ChIP-nexus profile at the top 200 CACGTG motifs after orienting each motif such that the higher signal is to the right. FIG. 5B shows average Myc ChIP-nexus profile at the same motifs shown in FIG. 5A and shows that Myc's footprint is generally localized to the same side of the motif as Max. FIG. 5C shows average base composition of the oriented E-box motifs from FIG. 5A. Note the slightly higher A content on the side with lower Max binding (right black arrow), and the frequent presence of a G on the favored interaction side (left black arrow). FIG. 5D shows the average DNA propeller twist score, measured in degrees, of the oriented E-box motifs, which shows a marked decline in the propeller twist on the favored interaction side (black arrow). FIG. 5E shows the average DNA minor groove width, measured in angstroms, of the oriented E-box motifs, which indicate a slight increase on the favored interaction side (black arrow). FIG. 5F shows differences in DNA propeller twist in E-box motifs-flanking regions correlate with Max ChIP-nexus footprint level. In the upper panel, the top 200 motifs were ordered by the difference in the mean DNA propeller twist measurement of the 6 base pairs flanking E-box motifs. The Max ChIP-nexus heatmap with the same order of motifs (lower panel) shows that the favored interaction side is most pronounced when there is an asymmetry in the DNA propeller twist around the motif.

FIG. 7A shows comparisons between biological ChIP-nexus replicates were performed by calling peaks using MACS 2 (Feng et al., 2012 in replicate 1 (200 bp centered on the peak summit, up to 10,000 peaks as arbitrary cutoff) and by plotting the average raw reads for each peak in both replicates. A tight line is observed for all factors, corresponding to Pearson correlations of 0.98-0.99. TBP, which has the highest correlation, is shown on the left, whereas Dorsal, which has the lowest correlation, is shown on the right. FIG. 7B shows comparison between ChIP-seq and ChIP-nexus. Peaks were called in the ChIP-seq data as in (a) and reads in these peaks from ChIP-seq and ChIP-nexus data are shown as a scatter plot. As can be seen for both TBP and Twist, there is an overall good correlation between the bulk data (Pearson correlations between 0.5-0.9). However, the ChIP-nexus data show an increased signal for a fraction of peaks. FIG. 7C shows that for individual examples shows that the ChIP-nexus signal is indeed highly specific. For example, the known dpp enhancer has a strong ChIP-nexus footprint (arrow), whereas the signal at the dpp promoter, which is equally high in the ChIP-seq data, is much lower and more distributed in the ChIP-nexus reads without any typical footprint (arrow). FIG. 7D shows the frequency distribution of consensus motifs in peaks identified by ChIP-seq (green) and ChIP-nexus (purple). Shown are the examples of Dorsal (left), for which ChIP-nexus shows a dramatic increase in motifs directly at the summit of the peaks, as well as for Twist (right), for which ChIP-nexus shows a more moderate improvement in motif frequency over ChIP-seq. FIG. 7E shows a quantification of the motif frequency in random genomic regions, in ChIP-seq peaks and in ChIP-nexus peaks within increasing windows from the peaks' summits for Dorsal and Twist. ChIP-nexus performs much better at a close interval to the peak summit (within 10 bp on either side, $Chi^2$ test, Dorsal $p<10^{-11}$, Twist $p<10^{-14}$), underscoring the increased specificity of ChIP-nexus. But even at wider intervals (within 100 bp on either side of the summit), ChIP-nexus peaks contain more motifs ($Chi^2$ test, Dorsal $p<2\times10^{-3}$, Twist $p<10^{-5}$), suggesting that ChIP-nexus has higher specificity as compared to ChIP-seq.

DETAILED DESCRIPTION OF THE INVENTION

Figure 1:
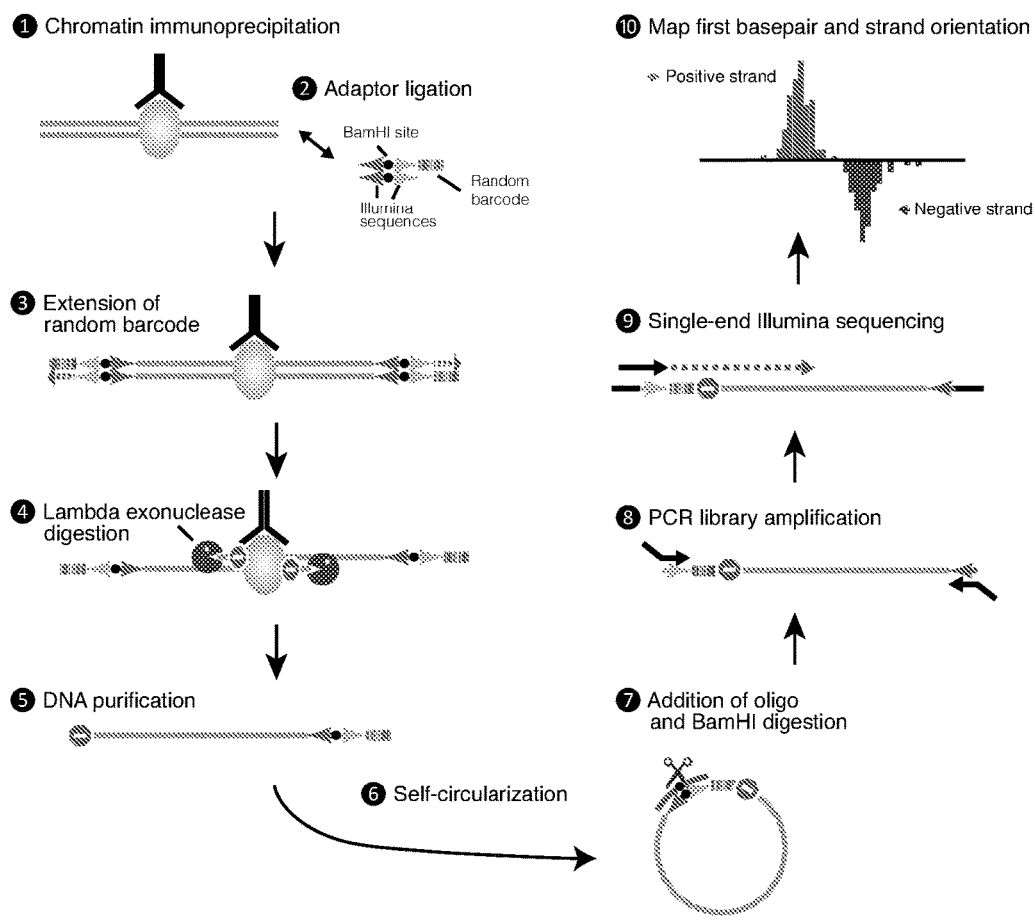
FIG. 1 shows a schematic outline of a ChIP-nexus process according to the present invention. 1) The transcription factor of interest (ovoid) is immunoprecipitated from chromatin fragments with antibodies in the same way as during standard ChIP-seq experiments. 2) While still bound to the antibodies, the DNA ends are repaired, dA-tailed and then ligated to a special adaptor that contains a pair of sequences for library amplification (arrows indicate the correct orientation for them to be functional), a BamHI site (black dot) for linearization, and a 9-nucleotide barcode containing 5 random bases and 4 fixed bases to remove reads resulting from over-amplification of library DNA. The random barcode is present as a 5' overhang, which reduces adaptor-adaptor ligation. 3) After the adaptor ligation step, the 5' overhang is filled, which copies the random barcode and generates blunt ends for lambda exonuclease digestion. 4) Lambda exonuclease (blue Pacman) digests until it encounters a physical barrier such as a cross-linked protein-DNA complex ('stop' base='Do not enter' sign). 5) Single-stranded DNA is eluted and purified. 6) Self-circularization places the barcode next to the 'stop' base. 7) An oligonucleotide (red arc) is paired with the region around the BamHI site for BamHI digestion (black scissors). 8) The digestion places, e.g., the two Illumina sequences, on either end, ready for PCR library amplification. 9) Each barcode followed by the genomic sequence starting with the 'stop' base is sequenced by single-end Illumina sequencing. 10) After alignment of the genomic sequence, reads with identical start positions and identical barcodes are removed. The final output is the position, number and strand orientation of the 'stop' bases. The frequencies of 'stop' bases on the positive strand are shown in red, while those on the negative strand are shown in blue.

One embodiment of the present invention is a method for identifying where a polypeptide of interest binds in a genome. The method comprises:

(a) carrying out a chromatin immunoprecipitation coupled to exonuclease digestion (ChIP-exo) process with an antibody against the polypeptide of interest;

(b) extracting a polynucleotide fragment to which the polypeptide of interest binds;

(c) carrying out a library preparation protocol adapted from an individual nucleotide resolution UV cross-linking and immunoprecipitation (iCLIP) process on the ChIP-exo processed polynucleotide fragment; and (d) sequencing the resulting polynucleotides.

As used herein, a "genome" means the genetic material in a cell or an organism, generally made of deoxyribonucleic acids (or ribonucleic acids for certain viruses). The coding portion of the genome be transcribed to produce messenger ribonucleic acid (mRNA), which can then be translated to generate polypeptides. The genome also includes those regions that are not transcribed to mRNA (or the non-coding portion). The non-coding region may be used to generate other forms of RNA, including transfer RNA (tRNA), ribosomal RNA (rRNA), micro RNA (miRNA), catalytic RNA. The non-coding region may also include nucleic acids that do not encode proteins or RNA, such as introns, promoters, enhancers, and the like.

A polypeptide of interest may bind to one or more location in a genome, such as, for example 2, 3, 4, 5, 6, 7, 8, 9, 10, 15, 20, 25, 30, 35, 40, 45, 50, 60, 70, 80, 90, 100 or more locations in a genome. A location in a genome may be a region of DNA of any length, including 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more base pairs (bp) in length. Locations in a genome at which a polypeptide of interest binds may be a region of consecutive base pairs or multiple, separate regions of consecutive base pairs. Likewise, a polypeptide may bind to a single location in a genome via a single region of the polypeptide or the polypeptide may bind to multiple regions in a genome, via either multiple regions of the polypeptide or multiple polypeptide entities.

As used herein, "binding", and grammatical variations thereof, means an association interaction between two molecules, such as via non-covalent interactions including, but not limited to, hydrogen bonding, hydrophobic interactions, van der Waals interactions, and electrostatic interactions. Binding may be sequence specific or non-sequence specific. Non-sequence specific binding may occur when, for example, a polypeptide of interest (i.e. a histone) binds to a polynucleotide of any sequence. Specific binding may occur when, for example, a polypeptide of interest (i.e. a transcription factor) binds only to specific sequences of nucleotides.

As used herein, a polypeptide of interest may be any polypeptide for which said polypeptide's genomic binding regions are sought. It is envisioned that a polypeptide of the present invention may include full length proteins and protein fragments. While the methods of the present invention may be utilized not only to determine at least one region of a genome at which a polypeptide of interest binds, they may also be utilized to determine if a polypeptide binds to a genome at all. The polypeptide of interest may selected from the group consisting of a transcription factor, a polymerase, a nuclease, and a histone.

In the present invention, polynucleotide fragment extracted in step (b) above may be of any length, including, but not limited to 2-1,000 nucleotides in length, such as 2, 3, 4, 5, 6, 7, 8, 9, 10, 15, 20, 25, 30, 35, 40, 45, 50, 60, 70, 80, 90, 100, 150, 200, 250, 300, 350, 400, 450, 500, 600, 700, 800, 900, 1,000 nucleotides in length, or more. The polynucleotide fragment may comprise a binding site for the polypeptide of interest of the present invention. For example, the polypeptide of interest may show protection beyond the binding motif.

As used herein, a "transcription factor" is any sequence-specific nucleic acid binding protein that affects the synthesis of an mRNA from the coding region of DNA, i.e. a gene. A transcription factor may activate or repress transcription of a gene by binding to regions proximal to or distant from a gene. Regions proximal to a gene may include promoter regions or transcription initiation sites, as well as intronic regions of genes. Conversely, enhancer regions may be found hundreds or thousands of base pairs upstream or downstream from a gene. Transcription factors, upon binding to specific regions of DNA, may activate transcription by, for example, promoting formation of the transcription initiation complex, recruiting RNA polymerase, and combinations thereof.

As used herein, a "polymerase" means an enzyme that generates polymers of nucleic acids. Preferably, the polymerase is an RNA polymerase or DNA polymerase. A polymerase of the present invention may interact with a genome at any position in the genome. In the case of RNA polymerase, the polymerase interacts with regions of the genome that code for functional products, i.e. genes. Transciption of a given gene in eukaryotes typically does not occur constitutively, but instead requires interaction of a transcription initiation complex, comprising, for example, transcription factors, with enhancer elements, promoter elements, and combinations thereof, in order to recruit a polymerase to a transcription start site.

As used herein, a "nuclease" is an enzyme that catalyzes the breakage of phosphodiester bonds connecting the nucleic acid subunits of a polynucleotide. A nuclease of the present invention may be an exonuclease or an endonuclease. Depending on the enzyme, an exonuclease catalyzes breakage of phosphodiester bonds either at the 5' or at the 3' end of a polynucleotide, thereby releasing the nucleic acids at the end of the polynucleotide. An endonuclease catalyzes breakage of phosphodiester bonds connecting nucleic acid subunits not found at the ends of a polynucleotide. Nucleases of the present invention, when acting on dsDNA, preferably catalyze breakage of phosphodiester bonds on both strands of the dsDNA. Nucleases may cleave equivalent phosphodiester bonds of complementary base pairs on each strand of a dsDNA molecule, thereby creating, from one dsDNA molecule, two dsDNA fragments with "blunt ends". Alternatively, nucleases may catalyze cleavage of phosphodiester bonds of non-complementary base pairs, thereby creating, from one dsDNA molecule, two dsDNA fragments with "overhangs" or "sticky ends".

As used herein, a "histone" of the present invention means a member of several protein families responsible for condensing genomic DNA into structures that may be contained in the nucleus. Histones and DNA comprise chromatin, the highly condensed state of a cell's genome. Histones are highly basic proteins that readily interact with negatively charged DNA molecules. Two histones from each of the core histone families, H2A, H2B, H3, and H4, aggregate to form the basic unit of chromatin, the nucleosome. Histone-bound DNA wraps around histone molecules, condensing long genomic DNA into a structure of shorter length. Genomic DNA may be further condensed by the formation of higher order structures of nucleosomes. While histones allow genomic DNA to be contained in the nucleus of a cell, they also provide the cell with an additional layer of gene expression regulation, in addition to transcription factor binding. Condensed chromatin, i.e., heterochromatin, serves as an effective barrier to transcription, preventing transcription factors and RNA polymerase from binding DNA and initiating transcription. Euchromatin comprises less compacted DNA that may be transcribed by the cell. Another layer of control over gene expression relates to histone modifications. Histone modifications include acetylation, methylation, phosphorylation, ubiquitination, ADP ribosylation, and others known to those of skill in the art. For example, histone acetylation reduces the strength of interaction between a histone and DNA, thereby promoting transcription, whereas histone deacetylation strengthens the interaction and represses transcription.

In one aspect of this embodiment, prior to step (a), above, the method further comprises cross-linking the polypeptide to a polypeptide binding site on the polynucleotide fragment with a cross-linking agent to form a reversible complex. This cross-linking step comprises contacting the polypeptide bound to a polynucleotide fragment with a cross-linking agent. As used herein, a "reversible complex" refers to at least two substances, preferably a polypeptide and a polynucleotide, but may also be two different polypeptides and a polynucleotide, covalently bound together as a result of the crosslinking agent. The complex between the polypeptide(s) and the polynucleotide may be separated by various means, including, but not limited to, the application of heat, proteinases, and combinations thereof. Preferably, the cross-linking agent is selected from the group consisting of formaldehyde, glutaraldehyde, and acetaldehyde.

As used herein, a "chromatin immunoprecipitation-exonuclease (ChIP-exo) process" means a protocol wherein an antibody to the protein of interest is used to isolate a plurality of polypeptide of interest-polynucleotide complexes that have been exposed to exonuclease digestion, resulting in polypeptide of interest-polynucleotide complexes that represent at least one location in the polynucleotide at which the polypeptide of interest binds. Preferably, the ChIP-exo process comprises:

(e) immunoprecipitating the polypeptide of interest which is cross-linked to the polynucleotide fragment using an antibody linked to a substrate;

(f) ligating an adaptor to an end of the polynucleotide fragment, which adaptor comprises two tail-to-tail primer sequences, a restriction site, and a polynucleotide barcode, which barcode protrudes as a 5' end overhang to prevent ligation to the barcode optionally followed by a washing step;

(g) filling in the 5' overhang to copy the barcode and to generate blunt ends for exonuclease digestion; and (h) digesting the blunt-ended polynucleotide fragment from step (g) with at least one exonuclease, which terminates digestion of the polynucleotide upon encountering a physical barrier caused by the polypeptide (stop base).

As used herein, "immunoprecipitating", and grammatical variations thereof, refers to a protocol in which polypeptides, such as antibodies, that specifically bind target polypeptides, are utilized to separate the target polypeptides and the substances that are physically linked to such polypeptides (such as a polynucleotide) from a plurality of other cellular materials. For example, cross-linked polypeptide-polynucleotide complexes of the present invention may be separated from other cellular materials by applying a cell extract to an affinity purification matrix, wherein the affinity purification matrix comprises an antibody specific for the target polypeptide linked to a substrate. The target polypeptide-polynucleotide complexes will bind to the antibody and may later be eluted, thereby separating the target polypeptide-polynucleotide complexes from other cellular materials. Detailed conditions for immunoprecipitation are disclosed herein and are also known in the art and may be found in e.g., Bonifacino et al., 2001.

As used herein, an "antibody" encompasses naturally occurring immunoglobulins, fragments thereof, as well as non-naturally occurring immunoglobulins, including, for example, single chain antibodies, chimeric antibodies (e.g., humanized murine antibodies), heteroconjugate antibodies (e.g., bispecific antibodies). Fragments of antibodies include those that bind antigen, (e.g., Fab', F(ab')$_2$, Fab, Fv, and rIgG). See, e.g., Pierce Catalog and Handbook, 1994-1995 (Pierce Chemical Co., Rockford, Ill.); Kuby, J., Immunology, 3rd Ed., W.H. Freeman & Co., New York (1998). The term "antibody" further includes both polyclonal and monoclonal antibodies.

As used herein, an antibody "linked" to a substrate is one that is covalently attached to the substrate via, for example, an inert chemical moiety, or, directly, via a cross-linking reaction between the substrate and the antibody.

As used herein, a "substrate" is a solid platform on which antibodies used in immunoprecipitation are bound. Preferably, the substrate is selected from the group consisting of agarose, sepharose, and magnetic agents. More preferably, the substrate is a Dynabead (Life Technologies, Grand Island, N.Y.).

As used herein, "ligating", and grammatical variations thereof, means the joining of the 5' and the 3' end of the same DNA molecule or two different DNA molecules. The former reaction results in a circular DNA molecule whereas the latter produces a linear DNA molecule. Ligases of the present invention may include T4 DNA Ligase, T7 DNA Ligase, CircLigase, and others known to those of skill in the art. Ligation reactions include, but are not limited to, sticky end ligations and blunt end ligations. Sticky end ligations involve complementary "overhangs" wherein one DNA strand of a dsDNA molecule comprises non-base paired nucleotides at the end of the molecule. Such non-base paired nucleotides may base pair with complementary non-base paired nucleotides on the same or a different DNA molecule, enabling a ligase to catalyze the covalent linkage of the ends of the DNA molecule(s). Blunt end ligations are non-specific ligations that do not involve complementary base pairing and thus are less efficient than sticky end ligations. Ligation may also be performed on either single stranded or double stranded DNA. For example, CircLigase catalyzes the ligation reaction between single stranded DNAs, whereas T4 and T7 DNA ligases join double stranded DNAs.

As used herein, an "adaptor" of the present invention means a piece of nucleic acid of known sequence that is added to the nucleic acid of interest, e.g., the polynucleotide. Two adaptors of the present invention are preferably ligated to the ends of a dsDNA fragment cross-linked to a polypeptide of interest, with one adaptor on each end of the fragment. Adaptors of the present invention comprise two tail-to-tail primer sequences, a restriction site, and a barcode.

Primer sequences are used in downstream polymerase chain reaction (PCR) amplification steps of the current invention and pair with complementary primers that are lengthened in the 5'-3' direction. The complementary primer sequences are used as templates in the 3'-5' direction. As used herein, "tail-to-tail" means that the primer sequences are oriented in inverted tandem direction.

"Restriction sites" of the present invention means to specific DNA sequences that may be recognized by a restriction endonuclease. The restriction endonuclease may catalyze the breakage of a phosphodiester bond in the sequence, thereby providing a sequence-specific means of fragmenting DNA. Preferably, the restriction site is selected from the group consisting of a BamHI site, an AaaI site, an AbaI site, an AbeI site, an AbrI site, an Acc113I site, an Acc16I site, an Acc36I site, an Acc65I site, an AccB1I site, an AccB2I site, an AccB7I site, an AccBSI site, an AccEBI site, an AccI site, an AccII site, an AccIII site, an AceI site, an AceII site, an AceIII site, an AciI site, an AclI site, an AcINI site, an AcIWI site, an AcpI site, an AcpII site, an AcrII site, an AcsI site, an AcuI site, an AcvI site, an AcyI site, an AdeI site, an AeuI site, an Afa16RI site, an Afa22MI site, an AfaI site, an AfeI site, an AflI site, an AflII site, an AflIII site, an AflIIII site, an AgeI site, an AgII site, an AhaB8I site, an AhaI site, an AhaII site, an AhaIII site, an AhdI site, an AhlI site, an AhyI site, an AitI site, an AjnI site, an AjoI site, an AleI site, an AlfI site, an AliAJI site, an AliI site, an AloI site, an AluI site, an Alw21I site, an Alw26I site, an Alw44I site, an AlwI site, an AlwNI site, an AlwXI site, an Ama87I site, an AocI site, an AocII site, an Aor13HI site, an Aor51HI site, an AorI site, an AosI site, an AosII site, an ApaBI site, an ApaCI site, an ApaI site, an ApaLI site, an ApaORI site, an ApeKI site, an ApiI site, an ApoI site, an ApyI site, an AquI site, an AscI site, an AseI site, an AseII site, an AsiAI site, an AsiI site, an AsiSI site, an AsnI site, an Asp10HI site, an Asp10HII site, an Asp26HI site, an Asp27HI site, an Asp35HI site, an Asp36HI site, an Asp40HI site, an Asp50HI site, an Asp700I site, an Asp713I site, an Asp718I site, an Asp745I site, an AspA2I site, an AspAI site, an AspEI site, an AspHI site, an AspI site, an AspLEI site, an AspMDI site, an AspMI site, an AspNI site, an AspS9I site, an AssI site, an AstWI site, an AsuC2I site, an AsuHPI site, an AsuI site, an AsuII site, an AsuIII site, an AsuNHI site, an AtsI site, an AvaI site, an AvaiI site, an AvcI site, an AviII site, an AvrBII site, an AvrII site, an AxyI site, a Bac36I site, a BaeI site, a Bal228I site, a BalI site, a BamNxI site, a BanAI site, a BanI site, a BanII site, a BanIII site, a BasI site, a BauI site, a BavAI site, a BavAII site, a BavBI site, a BavBII site, a BavCI site, a BavI site, a BbeI site, a Bbi24I site, a BbiII site, a Bbr7I site, a BbrI site, a BbrPI site, a BbsI site, a BbuI site, a Bbv12I site, a Bbv16II site, a BbvAI site, a BbvAII site, a BbvAIII site, a BbvBI site, a BbvCI site, a BbvI site, a BbvII site, a Bca77I site, a BccI site, a Bce22I site, a Bce243I site, a Bce4I site, a Bce751I site, a Bce83I site, a BceAI site, a BceBI site, a BceCI site, a BcefI site, a BcgI site, a Bci29I site, a BciBI site, a BciBII site, a BciVI site, a BcII site, a BcmI site, a BcnI site, a Bco116I site, a Bco118I site, a Bco27I site, a Bco5I site, a BcoAI site, a BcoI site, a BcoKI site, a BcuAI site, a BcuI site, a BdiI site, a BdiSI site, a BecAII site, a BepI site, a BetI site, a BfaI site, a Bfi57I site, a Bfi89I site, a BfiI site, a BfII site, a BfmI site, a BfrBI site, a BfrI site, a BfuAI site, a BfuCI site, a BfuI site, a BgII site, a BgIII site, a Bim19I site, a Bim19II site, a BimI site, a BinI site, a BlfI site, a Bli41I site, a Bli736I site, a Bli86I site, a BliAI site, a BliHKI site, a BliRI site, a BlnI site, a BloHI site, a BloHII site, a BlpI site, a BluI site, a Bme12I site, a Bme1390I site, a Bme142I site, a Bme1580I site, a Bme18I site, a Bme216I site, a Bme361I site, a Bme585I site, a BmgBI site, a BmrI site, a BmtI site, a BmyI site, a BnaI site, a BoxI site, a BpcI site, a BpiI site, a BpII site, a BpmI site, a BpoAI site, a BptI site, a Bpu10I site, a Bpu1102I site, a Bpu14I site, a Bpu95I site, a BpuAI site, a BpuAmI site, a BpuB5I site, a BpuDI site, a BpuEI site, a BpuI site, a BpuJI site, a BpuSI site, a Bsa29I site, a BsaAI site, a BsaBI site, a BsaHI site, a BsaI site, a BsaJI site, a BsaMI site, a BsaOI site, a BsaWI site, a BsaXI site, a Bsc107I site, a Bsc4I site, a Bsc91I site, a BscAI site, a BscBI site, a BscCI site, a BscFI site, a BscI site, a Bse118I site, a Bse15I site, a Bse16I site, a Bse17I site, a Bse1I site, a Bse21I site, a Bse24I site, a Bse3DI site, a Bse634I site, a Bse64I site, a Bse8I site, a BseAI site, a BseBI site, a BseCI site, a BseDI site, a BseGI site, a BseJI site, a BseKI site, a BseLI site, a BseMI site, a BseMII site, a BseNI site, a BsePI site, a BseQI site, a BseRI site, a BseSI site, a BseT10I site, a BseT9I site, a BseX3I site, a BseXI site, a BseYI site, a BseZI site, a BsgI site, a Bsh1236I site, a Bsh1285I site, a Bsh1365I site, a Bsh45I site, a BshFI site, a BshGI site, a BshI site, a BshKI site, a BshNI site, a BshTI site, a BsiBI site, a BsiCI site, a BsiEI site, a BsiHKAI site, a BsiHKCI site, a BsiI site, a BsiKI site, a BsiLI site, a BsiMI site, a BsiQI site, a BsiSI site, a BsiWI site, a BsiXI site, a BsiYI site, a BsiZI site, a BslFI site, a BslI site, a BsmAI site, a BsmBI site, a BsmFI site, a BsmI site, a BsmSI site, a Bso31I site, a BsoBI site, a BsoCI site, a BsoFI site, a BsoMAI site, a Bsp105I site, a Bsp106I site, a Bsp119I site, a Bsp120I site, a Bsp123I site, a Bsp1286I site, a Bsp13I site, a Bsp1407I site, a Bsp143I site, a Bsp143II site, a Bsp153AI site, a Bsp1720I site, a Bsp1894I site, a Bsp19I site, a Bsp2095I site, a Bsp211I site, a Bsp24I site, a Bsp4009I site, a Bsp423I site, a Bsp50I site, a Bsp519I site, a Bsp63I site, a Bsp67I site, a Bsp68I site, a Bsp6I site, a Bsp98I site, a BspA2I site, a BspAAI site, a BspAAII site, a BspAAIII site, a BspAI site, a BspANI site, a BspBI site, a BspBII site, a BspBRI site, a BspBS31I site, a BspCI site, a BspCNI site, a BspD6I site, a BspDI site, a BspEI site, a BspF4I site, a BspFI site, a BspHI site, a BspIS4I site, a BspJI site, a BspJII site, a BspKI site, a BspKT5I site, a BspKT6I site, a BspKT8I site, a BspLAI site, a BspLAII site, a BspLAIII site, a BspLI site, a BspLS2I site, a BspLU11I site, a BspLU11III site, a BspLU4I site, a BspM39I site, a BspM90I site, a BspMAI site, a BspMI site, a BspMII site, a BspMKI site, a BspNI site, a BspO4I site, a BspOVI site, a BspOVII site, a BspPI site, a BspR7I site, a BspRI site, a BspST5I site, a BspT104I site, a BspT107I site, a BspTI site, a BspTNI site, a BspTS514I site, a BspWI site, a BspXI site, a BspXII site, a BspZEI site, a BsrAI site, a BsrBI site, a BsrBRI site, a BsrDI site, a BsrFI site, a BsrGI site, a BsrI site, a BsrSI site, a BssAI site, a BssECI site, a BssHI site, a BssHII site, a BssIMI site, a BssKI site, a BssNAI site, a BssNI site, a BssSI site, a BssT1I site, a Bst100I site, a Bst1107I site, a Bst11I site, a Bst12I site, a Bst19I site, a Bst19II site, a Bst1I site, a Bst28I site, a Bst2BI site, a Bst2I site, a Bst2UI site, a Bst31NI site, a Bst31TI site, a Bst38I site, a Bst40I site, a Bst4CI site, a Bst6I site, a Bst71I site, a Bst98I site, a BstACI site, a BstAPI site, a BstAUI site, a BstB7SI site, a BstBAI site, a BstBI site, a BstBS32I site, a BstBSI site, a BstBZ153I site, a BstC8I site, a BstD102I site, a BstDEI site, a BstDSI site, a BstEII site, a BstENI site, a BstENII site, a BstEZ359I site, a BstF5I site, a BstFI site, a BstFNI site, a BstFZ438I site, a BstGZ53I site, a BstH2I site, a BstH9I site, a BstHHI site, a BstHPI site, a BstHZ55I site, a BstI site, a BstIZ316I site, a BstJZ301I site, a BstKTI site, a BstM6I site, a BstMAI site, a BstMBI site, a BstMCI site, a BstMWI site, a BstMZ611I site, a BstNI site, a BstNSI site, a BstNZ169I site, a BstOI site, a BstOZ616I site, a BstPAI site, a BstPI site, a BstPZ418I site, a BstPZ740I site, a BstRZ246I site, a BstSCI site, a BstSFI site, a BstSI site, a BstSNI site, a BstSWI site, a BstT10I site, a BstT7I site, a BstT9I site, a BstTS5I site, a BstUI site, a BstV1I site, a BstV2I site, a BstVI site, a BstX2I site, a BstXI site, a BstYI site, a BstZ17I site, a BstZI site, a Bsu1532I site, a Bsu15I site, a Bsu1854I site, a Bsu23I site, a Bsu36I site, a Bsu54I site, a Bsu6I site, a BsuBI site, a BsuFI site, a BsuMI site, a BsuRI site, a BsuTUI site, a BteI site, a BtgI site, a BtgZI site, a BthAI site, a BthCI site, a BthDI site, a BthEI site, a BtkI site, a BtkII site, a BtrI site, a BtsI site, a BveI site, a BvuBI site, a BvuI site, a Cac8I site, a CacI site, a CaiI site, a CauB3I site, a CauI site, a CauII site, a CbiI site, a CboI site, a CbrI site, a CciNI site, a CcoI site, a CcrI site, a CcuI site, a CcyI site, a CdiI site, a CelI site, a CelII site, a CeqI site, a CfII site, a CfoI site, a Cfr10I site, a Cfr13I site, a Cfr42I site, a Cfr6I site, a Cfr9I site, a CfrA4I site, a CfrBI site, a CfrI site, a CfrJ4I site, a CfuI site, a CfuII site, a ChaI site, a CjeI site, a CjePI site, a ClaI site, a CltI site, a CpfI site, a CpoI site, a CscI site, a CsiAI site, a CsiBI site, a Csp45I site, a Csp68KI site, a Csp68KII site, a Csp68KIII site, a Csp68KVI site, a Csp6I site, a CspAI site, a CspBI site, a CspCI site, a CspI site, a CspKVI site, a CstI site, a CstMI site, a CthII site, a CviAI site, a CviAII site, a CviBI site, a CviJI site, a CviQI site, a CviRI site, a CviRII site, a CviTI site, a CvnI site, a DdeI site, a DmaI site, a DpaI site, a DpnI site, a DpnII site, a DraI site, a DraII site, a DraIII site, a DrdI site, a DriI site, a DsaI site, a DsaII site, a DsaIII site, a DsaIV site, a DsaV site, a DseDI site, an EacI site, an Eae46I site, an EaeAI site, an EaeI site, an EagBI site, an EagI site, an EagMI site, an Eam1104I site, an Eam1105I site, an EarI site, an EcaI site, an Eci125I site, an EciI site, an Ecl136II site, an Ecl18kI site, an Ecl2zI site, an Ecl37kI site, an EclHKI site, an EclI site, an EclRI site, an EclXI site, an Eco105I site, an Eco130I site, an Eco137kI site, an Eco13kI site, an Eco147I site, an Eco1831I site, an Eco21kI site, an Eco24I site, an Eco255I site, an Eco27kI site, an Eco29kI site, an Eco31I site, an Eco32I site, an Eco47I site, an Eco47II site, an Eco52I site, an Eco53kI site, an Eco56I site, an Eco57I site, an Eco57MI site, an Eco64I site, an Eco72I site, an Eco75KI site, an Eco78I site, an Eco81I site, an Eco88I site, an Eco91I site, an EcoA4I site, an EcoHI site, an EcoHK31I site, an EcoICRI site, an EcoNI site, an EcoO109I site, an EcoO128I site, an EcoO44I site, an EcoO65I site, an EcoP15I site, an EcoR124II site, an EcoRI site, an EcoRII site, an EcoRV site, an EcoT14I site, an EcoT22I site, an EcoT38I site, an EcoVIII site, an EgeI site, an EheI site, an ErhB9I site, an ErhB9II site, an ErhI site, an ErpI site, an EsaBC3I site, an EsaBC4I site, an Esp1396I site, an Esp3I site, an Esp4I site, an EspI site, a FalI site, a FalIII site, a FaqI site, a FatI site, a FauBII site, a FauI site, a FauNDI site, a FbaI site, a FbII site, a FbrI site, a FdiI site, a FdiII site, a FgoI site, a FmuI site, a Fnu4HI site, a FnuAI site, a FnuCI site, a FnuDI site, a FnuDII site, a FnuDIII site, a FnuEI site, a FokI site, a FriOI site, a FseI site, a FsiI site, a Fsp1604I site, a Fsp4HI site, a FspAI site, a FspBI site, a FspI site, a FspII site, a FspMSI site, a FssI site, a FunI site, a FunII site, a GaII site, a GceGLI site, a GceI site, a GdiI site, a GdiII site, a GstI site, a GsuI site, a HacI site, a HaeI site, a HaeII site, a HaeIII site, a HaeIV site, a HalI site, a HalIII site, a HapII site, a HgaI site, a HgiAI site, a HgiBI site, a HgiCI site, a HgiCII site, a HgiCIII site, a HgiDI site, a HgiDII site, a HgiEI site, a HgiGI site, a HgiHI site, a HgiHII site, a HgiHIII site, a HgiI site, a HgiJI site, a HgiJII site, a HgiS22I site, a HhaI site, a HhaII site, a Hin1I site, a Hin1II site, a Hin2I site, a Hin4I site, a Hin6I site, a HincII site, a HindII site, a HindIII site, a HinfI site, a HinJCI site, a HinP1I site, a HjaI site, a HpaI site, a HpaII site, a HphI site, a Hpy178III site, a Hpy188I site, a Hpy188III site, a Hpy51I site, a Hpy8I site, a Hpy99I site, a HpyAV site, a HpyBI site, a HpyBII site, a HpyC1I site, a HpyCH4I site, a HpyCH4III site, a HpyCH4IV site, a HpyCH4V site, a HpyCI site, a HpyF10VI site, a HpyF44III site, a HsoI site, a Hsp92I site, a Hsp92II site, a HspAI site, a HsuI site, an ItaI site, a KasI site, a Kaz48kI site, a KoxII site, a Kpn2I site, a Kpn2kI site, a Kpn378I site, a Kpn49kI site, a Kpn49kII site, a KpnI site, a Ksp22I site, a Ksp632I site, a KspAI site, a KspI site, a Kzo49I site, a Kzo9I site, a LcaI site, a LlaAI site, a LlaBI site, a LlaCI site, a LlaG2I site, a Lmu60I site, a LpII site, a LpnI site, a LspI site, a LweI site, a MabI site, a MaeI site, a MaeII site, a MaeIII site, a MaeK81I site, a MaeK81II site, a MamI site, a MavI site, a MbiI site, a MboI site, a MboII site, a MchAI site, a MchAII site, a MchI site, a McrI site, a MfeI site, a MfII site, a MfoAI site, a Mgl14481I site, a MgoI site, a MhaAI site, a MhII site, a MkrAI site, a MlaAI site, a MlaI site, a MlsI site, a MltI site, a Mlu23I site, a Mlu31I site, a MluB2I site, a MluI site, a MluNI site, a Mly113I site, a MlyI site, a MmeI site, a MnII site, a MnoI site, a Mph1103I site, a MroI site, a MroNI site, a MroXI site, a MscI site, a MseI site, a MsII site, a Msp17I site, a Msp20I site, a Msp67I site, a MspA1I site, a MspB4I site, a MspCI site, a MspI site, a MspR9I site, a MspSWI site, a MspV281I site, a MspYI site, a MssI site, a MstI site, a MstII site, a MthZI site, a MunI site, a Mva1269I site, a MvaI site, a MvnI site, a MvrI site, a MwoI site, a MxaI site, a NaeI site, a NarI site, a NbII site, a NciI site, a NcoI site, a NcrI site, a NcuI site, a NdaI site, a NdeI site, a NdeII site, a NgoAIII site, a NgoAIV site, a NgoMIV site, a NgoPII site, a NgoPIII site, a NheI site, a NlaII site, a NlaIII site, a NlaIV site, a Nli3877I site, a NmeCI site, a NmeRI site, a NmuCI site, a NopI site, a NotI site, a NphI site, a NruGI site, a NruI site, a NsbI site, a NsiCI site, a NsiI site, a Nsp29132II site, a Nsp7121I site, a NspBII site, a NspHI site, a NspI site, a NspII site, a NspIII site, a NspIV site, a NspLKI site, a NspMACI site, a NspSAI site, a NspSAII site, a NspSAIV site, a NspV site, a NunII site, a OfoI site, a OkrAI site, an OliI site, an OxaNI site, a PabI site, a Pac25I site, a PacI site, a Pae14kI site, a Pae17kI site, a Pae18kI site, a Pae2kI site, a Pae5kI site, a PaeAI site, a PaeBI site, a PaeHI site, a PaeI site, a PaePI site, a PaeQI site, a PaeR7I site, a PagI site, a PalI site, a PamI site, a PamII site, a PanI site, a PasI site, a PauAI site, a PauAII site, a PauI site, a PceI site, a PciI site, a PctI site, a Pde12I site, a Pde133I site, a Pde137I site, a PdiI site, a PdmI site, a PfaAI site, a PfaAII site, a PfaAIII site, a PfeI site, a Pfl21I site, a Pfl23II site, a Pfl27I site, a Pfl8I site, a PflBI site, a PflFI site, a PflKI site, a PflMI site, a PfoI site, a PgaI site, a PhaI site, a PhoI site, a PinAI site, a PinBI site, a PinBII site, a PlaAI site, a PlaAII site, a PlaI site, a PlaII site, a Ple19I site, a PleI site, a PmaCI site, a Pme55I site, a PmeI site, a PmII site, a PovII site, a PpaAI site, a PpaAII site, a PpeI site, a PpiI site, a PpsI site, a Ppu10I site, a Ppu111I site, a PpuAI site, a PpuMI site, a PpuXI site, a PshAI site, a PshBI site, a PsiI site, a Psp03I site, a Psp124BI site, a Psp1406I site, a Psp23I site, a Psp5II site, a Psp6I site, a PspAI site, a PspALI site, a PspCI site, a PspEI site, a PspGI site, a PspLI site, a PspN4I site, a PspOMI site, a PspPI site, a PspPPI site, a PspXI site, a PsrI site, a PssI site, a PstI site, a PstNHI site, a Psu161I site, a PsuAI site, a PsuI site, a PsyI site, a PtaI site, a Pun14627I site, a Pun14627II site, a PunAI site, a PunAII site, a Pvu84II site, a PvuI site, a PvuII site, a RalF40I site, a RcaI site, a RflFI site, a RflFII site, a RleAI site, a RmaI site, a Rme21I site, a RsaI site, a RshI site, a RspLKI site, a RspLKII site, a RspXI site, a Rsr2I site, a RsrI site, a RsrII site, a Rtr63I site, a RtrI site, a SacI site, a SacII site, a SacNI site, a SalI site, a SalPI site, a SanDI site, a SapI site, a SarI site, a SatI site, a Sau3239I site, a Sau3AI site, a Sau96I site, a SauBMKI site, a SauHPI site, a SauI site, a SauLPI site, a SauLPII site, a SauMI site, a SauNI site, a SauSI site, a SbfI site, a Sbi68I site, a Sbo13I site, a SbvI site, a ScaI site, a SceIII site, a SchI site, a SchZI site, a SciI site, a SciNI site, a ScrFI site, a SdaI site, a SdiI site, a SduI site, a SecI site, a SeII site, a SenPT14bI site, a SenPT16I site, a SepI site, a SexAI site, a SexBI site, a SexCI site, a SfaI site, a SfaNI site, a SfcI site, a SfeI site, a SfiI site, a SfII site, a SfoI site, a Sfr274I site, a Sfr303I site, a SfuI site, a SgfI site, a SgrAI site, a SgrBI site, a SimI site, a SinI site, a SlaI site, a SleI site, a Slu1777I site, a SmaI site, a SmiI site, a SmiMI site, a SmII site, a SmuEI site, a SmuI site, a SnaBI site, a SniI site, a SnoI site, a Sol10179I site, a SoII site, a SpaHI site, a SpeI site, a SphI site, a SpII site, a SpmI site, a SpoI site, a SpuI site, a SrfI site, a Srl32DII site, a Srl55DI site, a Srl56DI site, a Srl5DI site, a SrII site, a Sru30DI site, a Sru4DI site, a SruI site, a SsbI site, a SscL1I site, a Sse1825I site, a Sse232I site, a Sse8387I site, a Sse8647I site, a Sse9I site, a SseAI site, a SseBI site, a SshAI site, a SsiAI site, a SsiBI site, a SsiI site, a SsII site, a SsoI site, a SsoII site, a Ssp1I site, a Ssp27144I site, a Ssp4800I site, a Ssp5230I site, a SspAI site, a SspBI site, a SspCI site, a SspD5I site, a SspD5II site, a SspI site, a SspRFI site, a SsrI site, a Sst12I site, a SstI site, a SstII site, a SteI site, a Sth117I site, a Sth132I site, a Sth134I site, a Sth368I site, a SthI site, a StrI site, a StsI site, a StuI site, a StyD4I site, a StyI site, a SuaI site, a SuiI site, a SunI site, a SurI site, a SviI site, a SwaI site, a TaaI site, a TaiI site, a Taq52I site, a TaqI site, a TaqII site, a TaqXI site, a TasI site, a TatI site, a TauI site, a TelI site, a TfiI site, a ThaI site, a TliI site, a Tru1I site, a Tru201I site, a Tru9I site, a TscI site, a TseI site, a Tsp1I site, a Tsp32I site, a Tsp32II site, a Tsp45I site, a Tsp49I site, a Tsp4CI site, a Tsp509I site, a Tsp8EI site, a TspBI site, a TspDTI site, a TspEI site, a TspGWI site, a TspMI site, a TspRI site, a Tth111I site, a Tth111II site, a TthHB8I site, an Uba153AI site, an Uba4009I site, an UbaM39I site, an UnbI site, an Uur960I site, a Van91I site, a Vha464I site, a VneI site, a VpaK11AI site, a VpaK11BI site, a VpaK32I site, a VspI site, a XagI site, a XapI site, a XbaI site, a XcaI site, a XceI site, a XciI site, a XcmI site, a XcyI site, a XhoI site, a XhoII site, a XmaCI site, a XmaI site, a XmaIII site, a XmaJI site, a XmiI site, a XmnI site, a XorII site, a XpaI site, a XspI site, a YenI site, a ZanI site, a ZhoI site, a ZraI site, a ZrmI site, and a Zsp2I site.

A "barcode", as used herein, refers to a nucleotide sequence that serves as a means of identification for sequenced polynucleotides of the present invention. Barcodes of the present invention may comprise at least 4 random bases, such as 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more bases in length. In addition to the random nucleotides, the barcode may have three or more fixed bases, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more bases in length. Preferably, both random and fixed bases are used as barcodes. More preferably, the barcode is composed of 5 random bases and 4 fixed bases. Methods for designing barcodes are known in the art. See, e.g., Bystrykh et al., 2012; Mir et al., 2013. Barcode sequences of the present invention initially protrude as 5' end overhangs to prevent further adaptor ligation to the barcode. The 5' end overhangs may provide that only a single adaptor is ligated to each end of a polynucleotide-polypeptide complex of the present invention. After adaptor ligation, an optional washing step may be incorporated before the steps described below.

Preferably, prior to the ligation step (step (f)), the immunoprecipitated cross-linked polypeptide-polynucleotide complex is optionally washed at least once in one or more buffers, which may be the same or different. More preferably, in any of the methods disclosed herein, the washing step, optional or otherwise, includes washing sequentially in one or more buffers selected from the group consisting of 10 mM Tris-EDTA buffer, Mixed Micelle buffer, Buffer 500, LiCl/Detergent buffer, and 10 mM Tris-HCl buffer. All buffer recipes are disclosed in the Examples or are well known to those of skill in the art, and may be found in, e.g., Arnold et al., 2008.

Also, prior to the ligation step, the method further comprises:
(i) end repairing the polynucleotide fragment with DNA polymerase I, T4 DNA polymerase, T4 polynucleotide kinase, and dNTPs optionally followed by a washing step; and
(j) dA tailing the polynucleotide fragment with a Klenow fragment and ATP optionally followed by a washing step.

As used herein, "end repairing" the polynucleotide fragment means a protocol in which fragmented DNA, for example, produced by shearing or nuclease treatment, is processed to generate blunt-ended dsDNA fragments with 5' phosphorylated ends on both of the strands. Details for end repair reactions are well known and are disclosed herein or may be found in e.g., Evans et al., 2008. Kits for end repairs are commercially available, for example, from Epicentre, Madison, Wis. After incubation, the reaction products may be washed using any of the wash buffers disclosed herein.

As used herein, "dA tailing" the polynucleotide fragment means a protocol in which 3' deoxyadenine (dA) tails are added to a polynucleotide. The dA tails may be utilized in later steps of the present method for more efficient ligation of adaptor molecules. Components included in a dA tailing reaction include, but are not limited to, ATP and Klenow fragment. A "Klenow fragment" of the present invention refers to a fragment of E. coli DNA polymerase I that has been enzymatically processed to be capable of 5'-3' polymerase activity and 3'-5' exonuclease activity. Preferably, a Klenow fragment of the present invention is not capable of 3'-5' exonuclease activity (3'-5' exo⁻). Details for dA tailing reactions are well known and are disclosed herein or may be found in e.g., Thompson et al., 2010. Kits for dA tailing are commercially available, for example, from New England Biolabs Inc. Ipswich, Mass.

Because, the preferred substrate for lambda exonuclease is blunt-ended dsDNA, step following the ligation of an adaptor (step (f)) is to fill in the 5' overhang to copy the barcode and generate blunt ends for exonuclease digestion. Preferably, a Klenow fragment is used to polymerize sequences complementary to the barcode, as is well known to those of skill in the art.

Preferably, the method further comprises, prior to the exonuclease digestion step (step (h)), end trimming the polynucleotide fragment by contacting it with a T4 DNA polymerase and dNTPs, optionally followed by a washing step. As used herein, "end trimming" the polynucleotide fragment refers to a protocol well known to those of skill in the art wherein "end-filled" polynucleotides are contacted with T4 DNA polymerase to remove potential 3' overhangs. T4 DNA polymerase has 3'-5' exonuclease activity and is thus suitable for this purpose.

As used herein, "digesting" refers to the enzymatic removal of nucleotides from a polynucleotide. The blunt-ended polynucleotide fragments cross-linked to a polypeptide of interest generated via procedures disclosed above may be digested with at least one exonuclease using procedures well known to those of skill in the art. Preferably, the at least one exonuclease has strand-specific dsDNA-specific exonuclease activity, such as 5'-3' dsDNA-specific exonuclease activity or 3'-5' dsDNA-specific exonuclease activity, and is selected from the group consisting of lambda exonuclease, T7 exonuclease, T5 exonuclease, exonuclease II, exonuclease III, exonuclease VIII, and CCR4. The exonuclease digests the cross-linked polynucleotide fragment until it reaches the cross-linked polypeptide of interest. The cross-linked polypeptide of interest causes a physical barrier which terminates digestion of the polynucleotide. The next, undigested base is referred to as the "stop base" and marks the first base in a sequence of bases bound by the polypeptide of interest. Exonuclease digestion occurs on both strands of a polynucleotide fragment cross-linked to a polypeptide of interest, thus, when exonuclease digestion is terminated on both strands, the resulting polynucleotide fragment is double-stranded where the polypeptide of interest causes a physical barrier, and single-stranded where the polypeptide is not interacting with the polynucleotide (i.e., the polynucleotide fragment potentially has long, 3' overhangs on each strand). Furthermore, the adaptor sequences now mark the 3' end of each strand, because the adaptors on the 5' end were digested by the exonuclease.

Preferably, step (h) of the ChIP-exo protocol further comprises optionally washing the polynucleotide fragment after digestion with an exonuclease having strand specific double-stranded-DNA-specific activity followed by contacting the polynucleotide fragment with an exonuclease having strand specific single-stranded-specific exonuclease activity. The exonuclease having strand specific single-stranded-specific exonuclease activity, such as 5'-3' or 3'-5' single-stranded-specific exonuclease activity, may be selected from the group consisting of RecJ$_f$ exonuclease, exonuclease I, and exonuclease VII. Single-stranded-specific exonuclease activity may be used to remove possible contaminants from a sample, such as, but not limited to, single-stranded DNA molecules not bound and cross-linked to a polypeptide of interest.

The extraction step (step (b) in which a polynucleotide fragment to which the polypeptide of interest binds is isolated and purified) may comprise:

(k) washing the polypeptide-polynucleotide complex from step (h) with a buffer;

(l) eluting the polypeptide-polynucleotide complex from the substrate;

(m) reverse cross-linking the polypeptide-polynucleotide complex;

(n) purifying the polynucleotide;

(o) denature the purified polynucleotide to make a single stranded polynucleotide; and (p) precipitating the purified single stranded polynucleotide.

As used herein, "eluting" the polynucleotide fragment-polypeptide of interest complexes from the substrate refers to a protocol well known to those of skill in the art in which an elution buffer is incubated with substrate-linked polynucleotide fragment-polypeptide of interest complexes to separate the complexes from the substrate.

As used herein, "reverse cross-linking" the polypeptide-polynucleotide complex refers to a protocol well known to those of skill in the art in which a protease (i.e., Protease K), heat, or both are utilized to break the covalent linkages between the polypeptides of interest and the polynucleotide fragments.

As used herein, "purifying" the polynucleotides of the present invention refers to a process well known to those of skill in the art in which polynucleotides are substantially separated from other components in a sample, including, but not limited to, polypeptides of interest. For example, phenol/chloroform/isoamyl alcohol (PCIA) may be added to a sample to separate the polynucleotides into an aqueous phase and the polypeptides and other contaminants into an organic phase. Transfer of the aqueous phase to a separate container provides substantially purified polynucleotides of the present invention.

As used herein, "precipitating" the polynucleotides of the present invention refers to a process well known to those of skill in the art in which substantially pure polynucleotides in solution are mixed with ethanol to draw the polynucleotides out of solution and into a solid precipitate. Centrifugation followed by decanting of the ethanol may result in a pellet of precipitated, crude DNA. Further ethanol washes may be performed to remove additional salts from the precipitate. Purified, precipitated DNA may then be resuspended for downstream processing. Preferably, precipitated DNA is denatured via, for example, application of heat, to separate the DNA strands for the subsequent iCLIP process.

The individual nucleotide resolution UV cross-linking and immunoprecipitation (iCLIP) process refers to a method of determining the binding site of RNA-binding proteins wherein native RNA-bound proteins are cross-linked with UV light and the RNA is subsequently used as a template for reverse transcription. The reverse transcriptase generates a DNA molecule complementary to the RNA, but stops short of reverse transcribing the entire RNA molecule due to the RNA-bound proteins acting as physical barriers against the progress of the reverse transcriptase. Further steps in the process are modified and incorporated into the modified iCLIP process disclosed herein.

The library preparation protocol adapted from the iCLIP process disclosed herein comprises:

(q) self-circularizing the purified single-stranded polynucleotide to place the barcode adjacent to the stop base;

(r) contacting the circularized polynucleotide from step (q) with (1) an oligonucleotide designed to produce localized double-stranded DNA around the restriction site in the adaptor and (2) a restriction enzyme that recognizes and cleaves the circularized polynucleotide at the restriction site in the adaptor to re-linearize the polynucleotide fragment, wherein upon relinearization the polynucleotide fragment comprises a primer sequence at each end; and (s) amplifying the polynucleotide sequence to an extent sufficient for sequencing.

As used herein, "self-circularizing" the isolated and purified polynucleotide fragment produced by the ChIP-exo process means the joining of the two ends of the purified polynucleotide fragment. For example, the self-circularizing step may comprise contacting the isolated and purified polynucleotide fragment produced by the ChIP-exo process with CircLigase under conditions and for a period of time sufficient for the polynucleotide fragment to self-circularize. Conditions for self-circularization of a polynucleotide fragment may include incubation at 60° C. with additional reagents such as water, CircLigase buffer, ATP, and $MnCl_2$, as well as the polynucleotide fragment and CircLigase. A period of time sufficient for self-circularization may be, for example, about 30 minutes to about 24 hours, preferably about 1 hour. Self-circularization results in the formation of a phosphodiester bond between the 5'-end and the 3'-end of the polynucleotide, generating a circular molecule. Prior to circularization, the 3'-end of the single-stranded polynucleotide may comprise an adaptor of the present invention, with the barcode region at the 3'-end of the adaptor, and the 5'-end of the polynucleotide may comprise the stop base. Thus, a self-circularized polynucleotide of the present invention preferably has the barcode adjacent to the stop base.

As used herein, an "oligonucleotide designed to produce localized double-stranded DNA around the restriction site in the adaptor" enables relinearization of the single-stranded circularized polynucleotide. Restriction enzyme digestion using, for example, BamHI, requires dsDNA, thus an oligonucleotide (from step (r)(1)) is designed to be complementary to the restriction site around the adaptor. Such an oligonucleotide is contacted with the circularized polynucleotide under conditions and for a period of time sufficient for the oligonucleotide to bind to the restriction site. Conditions and periods of time sufficient for binding may include incubation at: 95° C. for 5 minutes, temperature decrease at about 3.5° C./minute to 25° C., and incubation at 25° C. for about 30 minutes with additional reagents such as water, FastDigest buffer, the oligonucleotide, and the circularized polynucleotide. Once annealed, a restriction enzyme is added to the system that recognizes and cleaves the circularized polynucleotide at the restriction site in the adaptor. Both the designed oligonucleotide and the circularized polynucleotide are cleaved by a restriction enzyme at the restriction site, which results in a re-linearized polynucleotide fragment with primer sequences at each end. The primer sequences comprise those tail-to-tail primer sequences that originated in the adaptors disclosed previously.

Preferably, the method further comprises, after the restriction enzyme digestion of step (r)(2), precipitating the linearized polynucleotide fragment. Precipitation of the polynucleotide fragment may be accomplished using reagents and procedures disclosed herein and is well known to those of skill in the art. Once precipitated, the linearized polynucleotide fragment may be resuspended in a suitable solvent, for example, 25 µl of water.

As used herein, "amplifying the polynucleotide sequence to an extent sufficient for sequencing" refers to the use of methods well known to those of skill in the art to copy and increase the quantity of the linearized polynucleotide fragments for subsequent sequencing. Preferably, the amplifying step comprises carrying out PCR amplification of the linearized polynucleotide fragment. PCR protocols typically involve the use of short, complementary oligonucleotide primers that anneal to primer sequences on a polynucleotide fragment. When sequencing applications are anticipated, primers used in this step additionally contain a sequence complementary to single-end sequencing primers to enable use of the latter in downstream sequencing protocols. Amplification to an extent sufficient sufficient for sequencing may be accomplished through a variety of protocols. For example, a PCR reaction sample comprising 10 µl 5× Phusion buffer, 1.5 µl 10 mM dNTPs, 1 µl each of 10 µM universal (SEQ ID NO: 4) and barcode (SEQ ID NOs: 5-10) primers, 0.5 µl Phusion polymerase, and a volume of dissolved DNA yielding a volume of 50 µl in total (wherein the dissolved DNA is from the previous precipitation step) may be amplified under the following conditions to an extent sufficient for sequencing: 98° C. for 30 seconds, followed by 98° C. for 10 seconds, 65° C. for 10 seconds, and 72° C. for 30 seconds, the latter three repeated 18×, and 72° C. for 5 minutes.

Preferably, the method further comprises, after the amplification step, removing any adaptor dimers from the linearized polynucleotide fragment Removal of adaptor dimers may be accomplished via, for example, running the PCR products on a 2% agarose gel. Adaptor dimers appear as a thin bright band at the front edge of the library DNA, which forms a smear. By cutting the library DNA out of the gel and purifying it using an elution kit, adaptor dimers may be removed from the sample.

As used herein, "sequencing the iCLIP processed polynucleotide" comprises sequencing the amplified linearized polynucleotide fragment including the barcode and the polynucleotide fragment using a sequencing primer for at least 50 cycles of extension.

The sequence complementary to the sequencing primer is preferably incorporated in the amplification step (step (s)), as illustrated in step 9 of FIG. 1 (shown as black ends). The sequencing primer is preferably for use on an Illumina HiSeq platform. Illumina platforms utilize "sequencing-by-synthesis" technology, which involves single nucleotide primer extension on a solid support. Addition of nucleotide species linked to fluorescently labeled reversible terminator molecules during primer extension will extend primers annealed to amplified linearized polynucleotide fragments by a single nucleotide. The reversible terminator molecules serve as protecting groups that do not allow primer extension by more than one nucleotide at a time. Fluorescence is imaged across the solid support, generating a sequence consisting of a single base pair for each amplified linearized polynucleotide fragment. The reversible terminator molecules are then cleaved from the extended primer, allowing for subsequent nucleotide addition. A "cycle of extension", as used herein, thus comprises addition of reversible terminator-linked dNTPs, extension of the primer, detection of the fluorescent reversible terminator molecules, and removal of the reversible terminator molecules.

Other sequencing techniques known in the art may also be used for sequencing. These include, but are not limited to, Sanger sequencing (also referred to as dideoxy sequencing) and various sequencing-by-synthesis (SBS) methods as disclosed in, e.g., Metzker 2005, sequencing by hybridization, by ligation (for example, WO 2005021786), by degradation (for example, U.S. Pat. Nos. 5,622,824 and 6,140,053) and nanopore sequencing (which is commercially available from Oxford Nanopore Technologies, UK). In deep sequencing techniques, a given nucleotide in the sequence is read more than once during the sequencing process. Deep sequencing techniques are disclosed in e.g., U.S. Patent Publication No. 20120264632 and International Patent Publication No. WO2012125848.

In a preferred aspect of this embodiment, the method further comprises mapping the stop bases and their strand orientation to the genome.

As used herein, "mapping the stop bases" may comprise detecting the identity of the nucleotide directly downstream from the barcode sequence that is not part of a primer sequence. Strand orientation may be determined via, for example, computationally aligning a sequence to a reference genome and determining which strand the sequence is derived from.

Another embodiment of the present invention is a method for identifying where a polypeptide of interest binds in a genome. The method comprises:

(a) immunoprecipitating the polypeptide of interest which is cross-linked to a polynucleotide fragment using an antibody linked to a substrate;

(b) ligating an adaptor to the polynucleotide fragment, which adaptor comprises two tail-to-tail primer sequences, a restriction site, and a polynucleotide barcode, which barcode protrudes as a 5' end overhang to prevent ligation to the barcode optionally followed by a washing step;

(c) filling in the 5' overhang to copy the barcode and generate blunt ends for exonuclease digestion;

(d) digesting the blunt-ended polynucleotide fragment from step (c) with an exonuclease, which terminates digestion of the polynucleotide upon encountering a physical barrier caused by the polypeptide (stop base);

(e) extracting the polynucleotide fragment produced by the exonuclease digestion from step (d) and purify a single-stranded polynucleotide;

(f) self-circularizing the single-stranded polynucleotide from step (e) to place the barcode adjacent to the stop base;

(g) contacting the circularized polynucleotide with (1) an oligonucleotide designed to produce localized double-stranded DNA around the restriction site in the adaptor and (2) a restriction enzyme that recognizes and cleaves the circularized polynucleotide at the restriction site in the adaptor to re-linearize the polynucleotide fragment, wherein upon relinearization the polynucleotide fragment comprises a primer sequence at each end; and (h) amplifying the polynucleotide sequence to an extent sufficient for sequencing.

In this embodiment, various steps and reagents therein are as set forth above.

In one aspect of this embodiment, the method further comprises sequencing the amplified linearized polynucleotide fragment including the barcode and the polynucleotide fragment using a sequencing primer for at least 50 cycles of extension. Polynucleotide fragments, barcodes, sequencing primers, and cycles of extension are as set forth above.

A further embodiment of the present invention is a kit for carrying out any of the processes disclosed herein together with instructions for its use.

An additional embodiment of the present invention is a kit for identifying where a polypeptide of interest binds in a genome. The kit comprises:

(a) reagents sufficient to carry out a ChIP-exo process;

(b) reagents sufficient to carry out a library preparation protocol adapted from an iCLIP process; and (c) instructions for use.

In one aspect of this embodiment, the reagents sufficient to carry out ChIP-exo comprise:

(d) an exonuclease having 5'-3' single-stranded-specific exonuclease activity;

(e) an exonuclease having 5'-3' double-stranded-specific exonuclease activity;

(f) reagents for at least one buffer;

(g) reagents for at least one wash solution;

(f) reagents for at least one elution solution;

(g) reagents for at least one primer;

(h) at least one adaptor;

(i) a least one DNA polymerase;

(j) a polynucleotide kinase;

(k) dNTPs; and (l) a DNA ligase.

Exonucleases having 5'-3' single-stranded- or double-stranded-specific exonuclease activity are as set forth above and include, but are not limited to, lambda exonuclease, T7 exonuclease, T5 exonuclease, exonuclease II, exonuclease VIII, CCR4, RecJ$_f$ exonuclease, exonuclease I, and exonuclease VII. Preferably, the exonuclease having 5'-3' double-stranded-DNA-specific exonuclease activity is lambda exonuclease, and the exonuclease having 5'-3' single-stranded-DNA-specific exonuclease activity is RecJ$_f$ exonuclease.

Reagents for at least one buffer, wash solution, or elution solution include, but are not limited to, Tris-HCl, MgCl$_2$, dithiothreitol (DTT), bovine serum albumin (BSA), dNTPs, ATP, (NH$_4$)$_2$SO$_4$, glycine-KOH, EDTA, Triton X-100, NaCl, sucrose, sodium dodecyl sulfate (SDS), 4-(2-hydroxyethyl)-1-piperazineethanesulfonic acid (HEPES), sodium deoxycholate, LiCl, octylphenoxypolyethoxyethanol (IG-EPAL CA-630), polyethylene glycol (e.g. PEG 6000), DMSO, water, MnCl$_2$, glycogen, sodium acetate, ethanol, and glycerol. It is to be understood that the preceding list is not to be construed as limiting in any way and that any buffer, wash solution, or elution solution reagent not listed herein is well known to those of skill in the art.

Reagents for at least one primer include, but are not limited to, primers that may anneal to an adaptor of the present invention, such as Illumina's universal PCR primer (SEQ ID NO: 4) and TruSeq barcoded PCR primers (SEQ ID NOs: 5-10), single-end sequencing primers, and other primers having sequences disclosed herein.

Adaptors of the present invention include, but are not limited to, those adaptors with sequences such as those disclosed herein (SEQ ID NOs: 1-2) as well as any adaptor comprising two tail-to-tail primer sequences, a restriction site, and a 9-nucleotide barcode comprising five random bases and four fixed bases, which barcode protrudes as a 5' end overhang to prevent ligation to the barcode.

DNA polymerases of the present invention include, but are not limited to, T4 DNA polymerase, DNA polymerase I, large fragment, Klenow fragment, phi29 DNA polymerase, and Phusion polymerase. Polynucleotide kinases of the present invention include, but are not limited to, T4 polynucleotide kinase. dNTPs of the present invention include, but are not limited to, adenine, thymine, cytosine, guanine, and uracil. DNA ligases of the present invention include, but are not limited to, T4 DNA ligase, Quick T4 DNA ligase, and CircLigase. It is to be understood that DNA polymerases, polynucleotide kinases, dNTPs, and DNA ligases are well known to those of skill in the art and that the preceding lists should not be construed as limiting in any way.

In another aspect of this embodiment, reagents sufficient to carry out a library preparation protocol adapted from an iCLIP process comprise:

(l) a ligase;

(m) an oligonucleotide complementary to the restriction site in the adaptor;

(n) a restriction enzyme that binds to and clips the restriction site in the adaptor; and (o) amplification primers and amplification reagents.

Ligases are as set forth above. Preferably, CircLigase is utilized in an iCLIP protocol. An oligonucleotide complementary to the restriction site in the adaptor may be comprised of any sequence that is complementary to a restriction site disclosed herein. In the context of the present invention, an oligonucleotide complementary to the restriction site in the adaptor is represented by, for example, SEQ ID NO: 3. A restriction enzyme that binds to and clips the restriction site in the adaptor may be any restriction enzyme that recognizes and clips any of the restriction sites disclosed herein. Preferably, the restriction enzyme is BamHI. Amplification primers are those primers used in PCR as set forth above, and are represented herein by SEQ ID NOs: 4-10. Amplification reagents include, but are not limited to, template DNA, dNTPs, DNA polymerase, a buffer, and primers.

Another embodiment of the present invention is a kit for identifying where a polypeptide of interest binds in a genome. The kit comprises:

(a) reagents to wash chromatin;

(b) reagents for carrying out end repair;

(c) reagents for carrying out dA tailing;

(d) an adaptor;

(e) reagents for ligating the adaptor to the chromatin;

(f) reagents for filling in 5' overhang in the chromatin caused by the adaptor;

(g) reagents for end trimming;

(h) reagents for carrying out 5'-3' double-stranded-specific exonuclease digestion;

(i) reagents for carrying out 5'-3' single-stranded-specific exonuclease digestion;

(j) reagents for carrying out self-circularization of single stranded polynucleotide sequence;

(k) reagents for re-linearizing the circular polynucleotide sequence; and (l) reagents for carrying out PCR amplification of the re-linearized polynucleotide sequence.

Reagents to wash chromatin include, but are not limited to, Tris-EDTA buffer, Triton X-100, mixed micelle buffer, Buffer 500, LiCl/detergent buffer, and Tris-HCl. Reagents for carrying out end repair include, but are not limited to, DNA polymerase I, large fragment, T4 DNA polymerase, T4 polynucleotide kinase, dNTPs, and T4 ligase buffer. Reagents for carrying out dA tailing include, but are not limited to, Klenow fragment (3'-5' exo$^-$), ATP, and NEBuffer 2. Reagents for ligating the adaptor to the chromatin include, but are not limited to, Quick T4 DNA ligase, adaptors as set forth above, and Quick Ligation Reaction Buffer. Reagents for filling in 5' overhangs in the chromatin caused by the adaptor include, but are not limited to, Klenow fragment (3'-5' exo$^-$), dNTPs, and NEBuffer 2. Reagents for end trimming include, but are not limited to, T4 DNA polymerase, dNTPs, and T4 ligase buffer. Reagents for carrying out 5'-3' double-stranded-specific exonuclease digestion include, but are not limited to, lambda exonuclease, DMSO, Triton X-100, and lambda exonuclease reaction buffer. Reagents for carrying out 5'-3' single-stranded-specific exonuclease digestion include, but are not limited to, RecJf exonuclease, DMSO, Triton X-100, and NEBuffer 2.

Reagents for carrying out self-circularization of single stranded polynucleotide sequence (i.e. fragments) include, but are not limited to, water, CircLigase buffer, ATP, MnCl$_2$, and CircLigase. Reagents for re-linearizing the circular polynucleotide sequence include, but are not limited to, water, FastDigest buffer, cut-oligo (SEQ ID NO: 3), and BamHI. Reagents for carrying out PCR amplification of the re-linearized polynucleotide sequence include, but are not limited to, Phusion buffer, dNTPs, universal and barcode primers, Phusion polymerase, water, and DNA. All buffer recipes and components are disclosed in the Examples or are well known to those of skill in the art.

Any kit of the invention may also include suitable storage containers, e.g., ampules, vials, tubes, etc., for each reagent disclosed herein. The reagents may be present in the kits in any convenient form, such as, e.g., in a solution or in a powder form. The kits may further include a packaging container, optionally having one or more partitions for housing the various reagents.

Additional Definitions

As used herein, terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

The term "amino acid" means naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. An "amino acid analog" means compounds that have the same basic chemical structure as a naturally occurring amino acid, e.g., a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. An "amino acid mimetic" means a chemical compound that has a structure that is different from the general chemical structure of an amino acid, but that functions similarly to a naturally occurring amino acid.

"Nucleic acid" or "oligonucleotide" or "polynucleotide" used herein mean at least two nucleotides covalently linked together. Nucleic acids may be single stranded or double stranded, or may contain portions of both double stranded and single stranded sequences. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be synthesized as a single stranded molecule or expressed in a cell (in vitro or in vivo) using a synthetic gene. Nucleic acids may be obtained by chemical synthesis methods or by recombinant methods.

The nucleic acid may also be a RNA such as a mRNA, tRNA, short hairpin RNA (shRNA), short interfering RNA (siRNA), double-stranded RNA (dsRNA), transcriptional gene silencing RNA (ptgsRNA), Piwi-interacting RNA, pri-miRNA, pre-miRNA, micro-RNA (miRNA), or anti-miRNA, as described, e.g., in U.S. patent application Ser. Nos. 11/429,720, 11/384,049, 11/418,870, and 11/429,720 and Published International Application Nos. WO 2005/116250 and WO 2006/126040.

A nucleic acid will generally contain phosphodiester bonds, although nucleic acid analogs may be included that may have at least one different linkage, e.g., phosphoramidate, phosphorothioate, phosphorodithioate, or O-methyl-phosphoroamidite linkages and peptide nucleic acid backbones and linkages. Other analog nucleic acids include those with positive backbones; non-ionic backbones, and non-ribose backbones, including those disclosed in U.S. Pat. Nos. 5,235,033 and 5,034,506. Nucleic acids containing one or more non-naturally occurring or modified nucleotides are also included within the definition of nucleic acid. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; 0- and N-alkylated nucleotides, e.g. N6-methyl adenosine are suitable. The 2'-OH-group may be replaced by a group selected from H, OR, R, halo, SH, SR, NH$_2$, NHR, NR$_2$ or CN, wherein R is C$_1$-C$_6$ alkyl, alkenyl or alkynyl and halo is F, Cl, Br or I. Modified nucleotides also include nucleotides conjugated with cholesterol through, e.g., a hydroxyprolinol linkage as disclosed in Krutzfeldt et al., Nature (Oct. 30, 2005), Soutschek et al., Nature 432:173-178 (2004), and U.S. Patent Application Publication No. 20050107325. Modified nucleotides and nucleic acids may also include locked nucleic acids (LNA), as disclosed in U.S. Patent Application Publication No. 20020115080. Additional modified nucleotides and nucleic acids are disclosed in U.S. Patent Application Publication No. 20050182005. Modifications of the ribose-phosphate backbone may be done for a variety of reasons, e.g., to increase the stability and half-life of such molecules in physiological environments, to enhance diffusion across cell membranes, or as probes on a biochip. Mixtures of naturally occurring nucleic acids and analogs may be made; alternatively, mixtures of different nucleic acid analogs, and mixtures of naturally occurring nucleic acids and analogs may be made.

The terminology used herein is for the purpose of describing particular embodiments only and is not intended to be limiting. As used in the specification and the appended claims, the singular forms "a," "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

The following examples are provided to further illustrate the methods of the present invention. These examples are illustrative only and are not intended to limit the scope of the invention in any way.

EXAMPLES

Example 1

The Advantage of ChIP-Nexus

To achieve a robust protocol for the genome-wide profiling of transcription factor footprints, we combined the ChIP-exo protocol with the library preparation protocol from the iCLIP method developed for mapping RNA-protein interactions (Konig et al., 2010). We also added a unique randomized barcode to the adaptor, which enables monitoring over-amplification. (Kivioja et al., 2012, Casbon et al., 2011). We termed this method ChIP-nexus, which stands for ChIP experiments with nucleotide resolution through exonuclease, unique barcode and single ligation, but also for the Latin word nexus for "the act of binding together".

The important advantage of ChIP-nexus is that it requires adaptor ligation to only one end of the DNA fragment, while standard ChIP-seq and ChIP-exo protocols require adaptor ligation to both ends. ChIP-nexus circumvents one ligation step by using a circularization reaction, which is known to occur to completion and thus is not rate-limiting. Even if adaptor ligation only occurred on one end of the fragment, lambda exonuclease will nevertheless digest from both ends and the ligated strand can still be circularized and produce an amplifiable fragment. Since a ligation is generally a low-efficiency reaction, removing one ligation step from the library preparation significantly improves efficiency.

FIG. 1 illustrates how the unique barcode and the self-circularization reaction are incorporated into the ChIP-exo protocol. Briefly, chromatin fragments cross-linked by formaldehyde are immunoprecipitated as in a traditional ChIP-seq experiment (step 1). While still bound by the antibodies on beads, the fragments are then ligated to a uniquely designed adaptor: it contains two tail-to-tail primer sequences, which are utilized later for the Illumina library DNA amplification and sequencing; it also has a 9-nucleotide barcode composed of 5 random bases and 4 fixed bases protruding as a 5' end overhang (step 2). The overhang prevents ligation to this end and is filled in by Klenow (exo-), which copies the barcode by filling the recessive 3' end (step 3). After lambda exonuclease digestion, only the 3' end then carries the adaptor with barcode, marking the end without the stop base. After purification (step 5), the single-stranded DNA is self-circularized by circLigase (step 6), which places the "stop base" immediately downstream of the barcode. The circularized DNA product is then re-linearized by restriction enzyme digestion after adding an oligonucleotide that produces localized double-stranded DNA (step 7). The re-linearized DNA fragments now have the two Illumina primer sequences placed on either end of the DNA fragment, which allows for PCR library amplification (step 8). Using the standard Illumina primer, the unique barcode and the DNA fragment starting from the stop base are sequenced (step 9). The stop bases and their strand orientation are then mapped to the genome (step 10).

This ChIP-nexus protocol allowed us to reliably produce high-quality libraries from the low yields of DNA after lambda digestion (typically <10 ng in *Drosophila*) and achieved high level resolution without requiring more starting material than traditional ChIP-seq experiments. It is also less costly than commercial kits, as the library preparation reagents are based on made-to-order oligonucleotides.

Example 2

Sample Preparation for Chromatin Immunoprecipitation

K562 cells were growth at 37° C., 5% $CO_2$ with humidity in Iscove's DMEM media with 10% fetal bovine serum. Ten million cells were harvested for each ChIP-seq or ChIP-nexus experiment, respectively. Cells were cross-linked with 1/10 volume of fresh 11% formaldehyde solution (50 mM HEPES-KOH, pH 7.5; 100 mM NaCl; 1 mM EDTA; 0.5 mM EGTA; 11% formaldehyde) and rotated for 10 minutes at room temperature. Cross-linking was quenched by adding glycine to 0.125 M and cells and rotating for 5 minutes at room temperature. Cells were spun down, washed by PBS and re-suspended in A1 buffer (15 mM HEPES pH 7.5; 15 mM NaCl; 60 mM KCl; 4 mM $MgCl_2$; 0.5% Triton X-100; 0.5 mM DTT), transferred to a Wheaton Dounce homogenizer and broken down by twenty strokes with each pestle. Homogenates were spun down at 3000 g and washed three times with A1 buffer and once with A2 buffer (15 mM HEPES pH 7.5; 140 mM NaCl; 1 mM EDTA; 0.5 mM EGTA; 1% Triton X-100; 0.1% sodium deoxycholate; 1% SDS; 0.5% N-lauroylsarcosine sodium). Nuclei were re-suspended in 0.7 ml A2 buffer. Chromatin was sonicated by a Branson sonicator to 200-500 bp average size using the following parameters: power at 6.0; 6 minutes of accumulated sonication time; 30 seconds of individual bursts; and 90 seconds cooling time after each burst. Sonicated chromatin was cleared by centrifugation and the supernatant was used for ChIP.

*D. melanogaster* embryos were collected on apple plates from OregonR flies raised and kept at 25° C. and 60% humidity. The apple plates were placed into fly cages for 2 hours and then incubated for another two hours outside such that the embryos were aged 2-4 hours after egg laying (AEL). Embryo collections and whole cell extract (WCE) preparations were performed as previously described (Sandmann et al., 2007, Zeitlinger et al., 2007). About 0.1 g of fixed embryos were used per ChIP-seq or ChIP-nexus.

S2 cells were grown at 25° C. in HyClone SFX-Insect Cell Culture Media with 1× penicillin and streptomycin (Sigma-Aldrich). About twenty million cells were harvested for each ChIP-seq or ChIP-nexus experiment. S2 sells were cross-linked by 1% formaldehyde for 10 minutes at room temperature. Formaldehyde was quenched by 0.125 M glycine for 5 minutes. Cells were washed with PBS, re-suspended in Orlando and Paro's Buffer A (0.25% triton X-100, 10 mM EDTA, 0.5 mM EGTA, 10 mM Tris-HCl, pH 8.0) and rotated for 10 minutes at room temperature. Nuclei were spun down and re-suspended in RIPA buffer (10 mM Tris-HCl, pH 8.0; 140 mM NaCl; 0.1% SDS; 0.1% sodium deoxycholate; 0.5% sarkosyl; 1% Triton X-100). Chromatin was fragmented with the Bioruptor by two rounds of 15 minutes sonication at high power. Chromatin was cleared by centrifugation and the supernatant was used for ChIP.

Chromatin immunoprecipitations were performed as previously described (He et al., 2011) with rabbit polyclonal antibodies against TBP (sc-204X, 3 µg/ChIP), Dorsal (20 µg/ChIP), Twist (10 µg/ChIP), Max (sc-28209, 8 µg/ChIP) and Myc (sc-28207, 8 µg/ChIP). The rabbit polyclonal antibodies against Dorsal protein (a.a. 39-346) and Twist protein (C-terminal a.a. 340-490) were produced by GenScript.

Example 3

ChIP-Nexus Digestion Steps

The digestion with lambda exonuclease was carried out using a modified version of the published ChIP-exo protocol (Rhee et al., 2011), while the chromatin was immunoprecipitated on Dynabeads. A detailed protocol is available as Supplementary Protocol 1 from our web page (research.stowers.org/zeitlingerlab). This protocol is hereby incorporated by reference as if recited in full herein.

(1) Wash steps: The chromatin was first washed five times with the following buffers: 10 mM Tris-EDTA Buffer, 0.1% Triton X-100; Mixed Micelle buffer (150 mM NaCl, 20 mM tri-HCl (pH 8.0), 5 mM EDTA, 5.2% sucrose, 1.0% Triton X-100 and 0.2% SDS); Buffer 500 (250 mM NaCl, 5 mM Tris-HCl (pH 8.0), 25 mM HEPES, 0.5% Triton X-100, 0.05% sodium deoxycholate and 0.5 mM EDTA); LiCl/Detergent buffer (250 mM LiCl, 0.5% IGEPAL CA-630, 10 mM Tris-HCl (pH 8.0), 0.5% sodium deoxycholate and 10 mM EDTA); 10 mM Tris-HCl (pH 8.0, pH 7.5, or pH 9.5 depending on the next enzymatic step). After the last wash, residual buffer was drained before the next enzymatic reaction was added. These washing steps were repeated between all following steps.

(2) End repair: 0.05 u/µl DNA polymerase I, large fragment (New England Biolabs, M0210), 0.15 u/µl T4 DNA polymerase (New England Biolabs, M0203), 0.5 u/µl T4 polynucleotide kinase (New England Biolabs, M0201) and 0.4 mM/µl dNTPs in 30-40 µl 1×NEB T4 ligase buffer (New England Biolabs, B0202) at 12° C. for 30 minutes. Washing steps were as above.

(3) dA tailing: 0.3 u/µl klenow fragment (3'-5' exo-) (New England Biolabs, M0212) and 0.2 mM/µl ATP in 50 µl 1×NEBuffer 2 at 37° C. for 30 minutes. Washing steps were as above.

(4) Adaptor ligation: 200 u/µl Quick T4 DNA ligase (New England Biolabs, M2200) and 60 nM/µl adaptor (see Table 1 for full sequences and conditions for annealing) in 50 µl 1× Quick Ligation Reaction Buffer at 25° C. for 60 minute. Washing steps were as above.

(5) End fill: 0.1 u/µl klenow fragment (3'-5' exo-) (New England Biolabs, M0212) and 0.1 mM/µl dNTPs in 50 µl 1×NEBuffer 2 at 37° C. for 30 minutes. Washing steps were as above.

(6) End trim: 0.09 u/µl T4 DNA polymerase (New England Biolabs, M0203) and 0.1 mM/µl dNTPs in 50 µl 1×NEB T4 ligase buffer at 12° C. for 5 minutes. Washing steps were as above.

(7) Lambda exonuclease digestion: 0.2 u/µl lambda exonuclease (New England Biolabs, M0262), 5% DMSO and 0.1% Triton X-100 in 100 µl 1×NEB Lambda exonuclease reaction buffer at 37° C. for 60 minutes with constant agitation. Washing steps were as above.

(8) RecJf exonuclease: 0.75 u/µl RecJf exonuclease (New England Biolabs, M0264), 5% DMSO and 0.1% Triton X-100 in 100 µl 1×NEBuffer 2 at 37° C. for 60 minutes with constant agitation.

After RecJf digestion, the Dynabeads were washed three times with RIPA buffer (50 mM HEPES, pH7.5, 1 mM EDTA, 0.7% sodium deoxycholate, 1% IGEPAL CA-630, 0.5 M LiCl). DNA elution, reverse cross-linking, DNA purification and precipitation were performed as previously described (Sandmann et al., 2007, Zeitlinger et al., 2007).

Enrichments for each transcription factor of interest were confirmed at known target sites by real-time PCR (StepOnePlus, Applied Biosystem) before library preparation.

Example 4

ChIP-Nexus Library Preparation

The library preparation protocol is based on the iCLIP protocol (Konig et al., 2010).

(1) Self-circularization: precipitated DNA samples were dissolved in 11.25 µl H$_2$O, 1.5 µl 10× CircLigase buffer, 0.75 µl 1 mM ATP, 0.75 µl 50 mM MnCl$_2$, 0.75 µl CircLigase (Epicentre) and incubated for 60 minutes at 60° C.

(2) Preparation for linearization by BamHI: an oligonucleotide complementary to the BamHI restriction site (cut-oligo, see oligo list for full sequences) was annealed by adding 26 µl H$_2$O, 5 µl FastDigest buffer (Fermentas) and 1 µl 10 µM cut-oligo. The mixture was incubated with the following program on a thermocycler: 5 minutes at 95° C., ramp down to 25° C. at a rate of about 3.5° C./minute, and held at 25° C. for 30 minutes.

(3) BamHI cleavage: add 3 µl Fastdigest BamHI (Fermentas) and incubate for 30 min at 37° C.

(4) DNA precipitation: after BamHI digestion, samples were mixed with 150 µl TE buffer, 30 µg glycogen, 20 µl 3 M/I sodium acetate (pH 5.5) and 500 µl 100% ethanol and incubated for 2.5 h at −80° C. DNA samples were precipitated by centrifugation for 30 minutes at 16,100 g at 4° C., washed with 500 µl 80% ethanol, dried overnight at room temperature and resuspended in 25 µl H$_2$O.

(5) PCR amplification: add 10 µl 5× Phusion buffer, 1.5 µl 10 mM dNTP, 1 µl each of 10 µM universal and barcode primer (see oligo list for full sequences), and 0.5 µl Phusion Polymerase (New England Biolabs, M0530), and H$_2$O to dissolved DNA to give a volume of 50 µl in total. DNA was amplified by the following program: 98° C. for 30 seconds; 18× (98° C. for 10 seconds, 65° C. for 30 seconds, 72° C. for 30 seconds); 72° C. for 5 minutes.

(6) Removal of contaminating adaptor dimers: PCR products were run on a 2% agarose gel. The adaptor dimers usually form a thin bright band migrating at the front edge of the library DNA, which forms a smear. The library DNA was carefully sliced out, purified by MinElute kit (Qiagen, 28006) and eluted into 12 µl elution buffer.

(7) Sequencing: DNA samples were sequenced on an Illumina HiSeq platform with the single-end sequencing primer over 50 cycles of extension according to manufacturer's instructions.

TABLE 1

List of ChIP-Nexus Oligonucleotides

| Name | Identity | Modification | Barcode | Sequence |
|---|---|---|---|---|
| Nex_adapter_UBamHI | Adaptor: universal | 5' phosphate | / | /5Phos/GATCGGAAGAGCACACGTCTGGATCCACGACGCTCTTCC (SEQ ID NO: 1) |

TABLE 1-continued

List of ChIP-Nexus Oligonucleotides

| Name | Identity | Modification | Barcode | Sequence |
|---|---|---|---|---|
| Nex_adapter_BN5BamHI | Adaptor: barcoded | 5' phosphate | TCAGNNNNN | /5Phos/TCAGNNNNNAGATCGGAAGAGCGTCGTGGATCCAGACGTGTGCTCTTCCGATCT (SEQ ID NO: 2) |
| Nex_cut_BamHI | Oligo for digestion | / | / | GAAGAGCGTCGTGGATCCAGACGTG (SEQ ID NO: 3) |
| Nex_primer_U | Primer: universal | 3' phosphoro-thioate bond | / | AATGATACGGCGACCACCGAGATCTACACTCTTTCCCTACACGACGCTCTTCCGATC*T (SEQ ID NO: 4) |
| Nex_primer_B01 | Primer: barcoded | 3' phosphoro-thioate bond | ATCACG | CAAGCAGAAGACGGCATACGAGATCGTGATGTGACTGGAGTTCAGACGTGTGCTCTTCCGATC*T (SEQ ID NO: 5) |
| Nex_primer_B02 | Primer: barcoded | 3' phosphoro-thioate bond | CGATGT | CAAGCAGAAGACGGCATACGAGATACATCGGTGACTGGAGTTCAGACGTGTGCTCTTCCGATC*T (SEQ ID NO: 6) |
| Nex_primer_B03 | Primer: barcoded | 3' phosphoro-thioate bond | TTAGGC | CAAGCAGAAGACGGCATACGAGATGCCTAAGTGACTGGAGTTCAGACGTGTGCTCTTCCGATC*T (SEQ ID NO: 7) |
| Nex_primer_B04 | Primer: barcoded | 3' phosphoro-thioate bond | TGACCA | CAAGCAGAAGACGGCATACGAGATTGGTCAGTGACTGGAGTTCAGACGTGTGCTCTTCCGATC*T (SEQ ID NO: 8) |
| Nex_primer_B05 | Primer: barcoded | 3' phosphoro-thioate bond | ACAGTG | CAAGCAGAAGACGGCATACGAGATCACTGTGTGACTGGAGTTCAGACGTGTGCTCTTCCGATC*T (SEQ ID NO: 9) |
| Nex_primer_B06 | Primer: barcoded | 3' phosphoro-thioate bond | GCCAAT | CAAGCAGAAGACGGCATACGAGATATTGGCGTGACTGGAGTTCAGACGTGTGCTCTTCCGATC*T (SEQ ID NO: 10) |
| Nex_primer_B07 | Primer: barcoded | 3' phosphoro-thioate bond | CAGATC | CAAGCAGAAGACGGCATACGAGATGATCTGGTGACTGGAGTTCAGACGTGTGCTCTTCCGATC*T |
| Nex_primer_B08 | Primer: barcoded | 3' phosphoro-thioate bond | ACTTGA | CAAGCAGAAGACGGCATACGAGATTCAAGTGTGACTGGAGTTCAGACGTGTGCTCTTCCGATC*T |

*To anneal the adaptor oligonucleotides, 50 µM of each are mixed in 1x TE and 50 mM NaCl. The mixture is placed in a thermocycler and heated to 95° C. for 5 minutes. The temperature is ramped down to 25° C. at a rate of about 3.5° C./minute, and held at 25° C. for 30 minutes.
Note:
SEQ ID NOS: 1 and 2 comprise a 5'-phosphate and SEQ ID NOs: 4-10 comprise a phosphoro-thioate bond between the final two nucleotides (C and T)

Example 5

ChIP-Nexus Analysis

Data Processing
ChIP-Nexus Samples

Sequencing reads passing the default Illumina quality filter (CASAVA v1.8.2) were further filtered for the presence of the fixed barcode CTGA starting at read position 6. The random and fixed barcode sequences were then removed (read positions 1 through 9), while retaining the 5-bp random barcode sequence for each read separately. Adaptor sequences from the right end were then trimmed using the cutadapt tool (Martin et al., 2011). All reads of at least 22 bp in length after adaptor trimming were then aligned to the appropriate reference genome (dm3 for *Drosophila melanogaster* and hg19 for *Homo sapiens*) using bowtie v1.0.0 (Langmead et al., 2009). Only uniquely aligning reads with a maximum of 2 mismatches were kept. To remove duplicates, reads with identical alignment coordinates (chromosome, start position and strand) and identical random barcode were removed using R (R Core Team, 2013) and Bioconductor (Gentleman et al., 2004). All reads were then split by strand orientation and a genome-wide count of the start positions (lambda exonuclease's stop position) was calculated for each strand.
Peconic Samples Peconic provided aligned BAM files for both Dorsal replicates. Aligned reads were separated by strand orientation and reduced to the first sequenced base (lambda exonuclease's stop position). Genome-wide counts for read start positions were then calculated.

ChIP-Exo TBP Samples

Previously published ChIP-exo TBP data from human K562 cells (Venters et al., 2013) were downloaded from the Sequence Read Archive (accession numbers SRR770743 and SRR770744) and aligned to the UCSC hg19 reference genome using the same parameters as for ChIP-nexus. Aligned reads were separated by strand and reduced to the first sequenced base (lambda exonuclease's stop position). Genome-wide counts for read start positions were then calculated.

ChIP-Seq Samples

ChIP-seq reads were aligned to the appropriate reference genome (dm3 or hg19) using the same parameters as for the ChIP-nexus samples. After alignment, reads were extended in the 5' to 3' direction to each sample's estimated library insert size as determined by a Bioanalyzer. These extensions were 136 bp for Dorsal, 83 bp for Max and 74 bp for TBP. After extension, genome-wide coverage values were calculated.

Reference Genome Modification for Dorsal Rho Enhancer Region

The rho enhancer from the Oregon-R strain disclosed above differed from the reference genome by multiple SNPs and resulted in visible gaps of read coverage. To correct for this problem genome-wide, the following procedure was performed: The Dorsal ChIP-seq replicate 1 was realigned to the reference genome while allowing up to 3 mismatches.

Using samtools (Li et al., 2009), genome-wide variants were identified using the following parameters:

```
samtools mpileup -uD -f dm3.fasta
    dmel_embryo_dl_chipseq_01_mm3.bam | bcftools view -vcg
```

Figure 2:
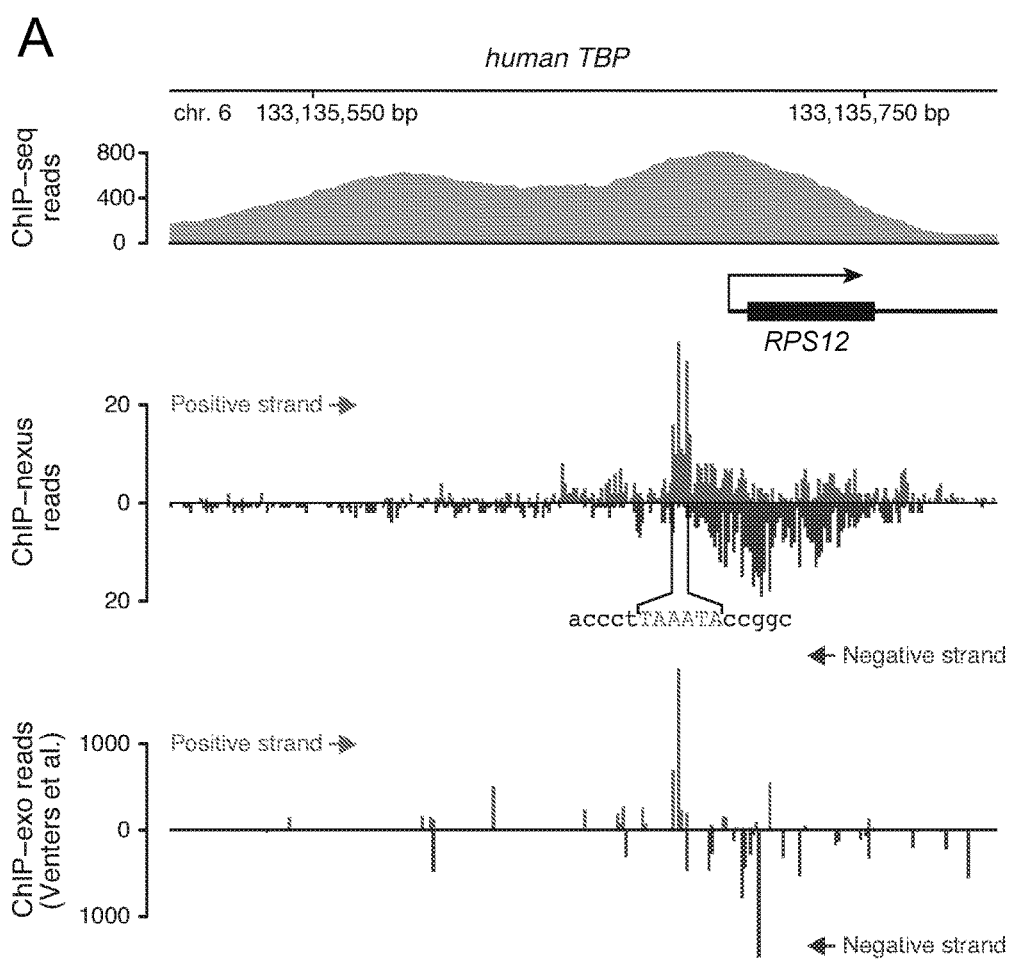
FIG. 2 shows superior performance of a ChIP-nexus process according to the present invention in discovering relevant binding footprints for transcription factors. Standard ChIP-seq data (extended reads) and ChIP-nexus data (raw stop base reads) are shown in comparison.

The identified single-allele variants were then used to create a modified reference genome matching the sequence of the Oregon-R strain disclosed herein. The Dorsal ChIP-nexus replicate 1 sample was then realigned to this modified reference genome and processed as originally described. Data from this realignment were used to plot the Dorsal ChIPnexus profiles in FIG. 2. As Peconic did not provide the unaligned reads for the Dorsal ChIP-exo data, this read recovery procedure was only performed on the ChIP-nexus data.

Peak Calling

MACS v.2.0.10 (Gordan et al., 2013) was run on the ChIP-nexus replicate #1 samples and the ChIP-seq samples for TBP, Dorsal, Twist and Max using the following parameters:

macs2 callpeak -g dm-keep-dup=all-call-summits

Resulting peak summits were sorted by score and a maximum of 10,000 were retained per sample.

Comparison Scatterplots

For each scatterplot, the peaks detected in the sample on the x axis were resized to 201 bp centered at the summit. Each peak was scored using the genome-wide coverage values for the two samples. For ChIP-seq, these coverage values were calculated using the entire extended fragment size. For ChIP-nexus and ChIP-exo, coverage values were calculated using only the first base pair of each aligned fragment. Pearson correlations were calculated using the raw values before log transformation.

ChIP-Nexus and ChIP-Seq Motif Presence

For Dorsal, Twist and Max, the top 200 peaks by MACS score were used. Motif frequency plots were generated by scoring each position in the genome as either 1 or 0 based on the presence of a consensus motif for each factor. These consensus motifs were GGRWWTTCC with up to one mismatch for Dorsal, CABATG with no mismatches for Twist and CACGTG with no mismatches for Max. The average motif presence around the top 200 peak summits was then calculated and plotted for both ChIP-seq and ChIP-nexus (replicate 1) samples.

For each peak, the distance from the peak summit to the nearest consensus motif was calculated. For distance thresholds of 10, 20, 50 and 100 bp, a two-sided Chi-squared test was used to test for a significant difference in proportion of peaks near a consensus motif between ChIP-nexus and ChIP-seq.

Motif Average Profiles and Heatmaps

For each factor, all non-overlapping instances of its motif with up to one mismatch were scored for ChIP-nexus signal by summing the total reads from both strands in a region centered on the motif (29 bp for Dorsal, 15 bp for Max and 51 bp for Twist).

For the heatmap, the data from the top 200 motifs were oriented such that the motif was on the positive strand. The 200 profiles were then sorted by total reads in a 50-bp window centered on the motif. Positive and negative strand reads were normalized from zero reads (minimum) to the read value at the $98^{th}$ percentile or higher (maximum) for display.

E-box specificity plots were constructed by separately averaging the positive and negative strand ChIP-nexus signal among the top scoring 200 non-overlapping instances of each unique E-box motif CANNTG. Each motif was scored by summing the ChIP-nexus reads in a window 50 bp centered on the motif.

Figure 5:
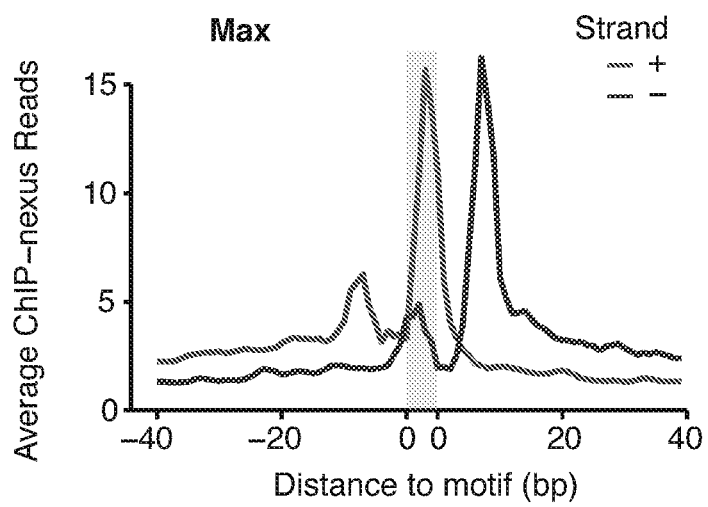
FIG. 5 shows that the favored interaction side of Max at E-Box motifs correlates with features of DNA shape.
Figure 5:
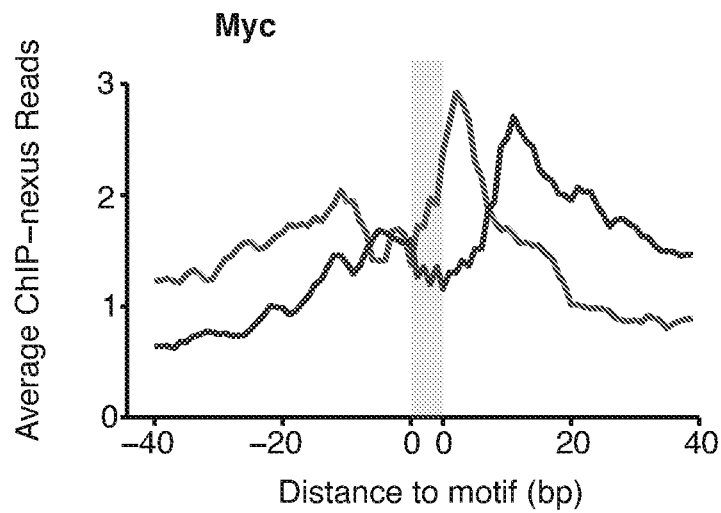

To analyze the favored interaction side of Max in FIG. 5, the same top 200 Max motifs described above were scored for ChIP-nexus signal on the left and right side. The left side signal was calculated by summing the positive strand reads in a region 9-bp wide centered 8-bp upstream of the motif and the negative strand reads in a region 9-bp wide centered on the motif +1 position. The right side signal was calculated by summing the positive strand reads in a region 9-bp wide centered on the motif +4 position and the negative strand reads in a region 9-bp wide centered 8-bp downstream of the motif. Each motif was then oriented so that the side with higher signal was to the right of the motif.

DNA Shape

Genome-wide DNA shape parameters were collected for the positive strand of the *Drosophila melanogaster* UCSC dm3 reference genome. First, all 1,024 DNA pentamers were uploaded to the DNA Shape web service (Zhou et al., 2013) to obtain predictions for minor groove width, roll, propeller twist and helix twist. For the minor groove width and propeller twist, a single value was provided for the center base of each pentamer. These values were applied genome-wide by aligning the pentamers to the positive strand of the reference genome. Roll and helix twist were provided as two step values between the center base of each pentamer and its two adjacent bases. For these two parameters, the two values were labeled as the "left" and "right" values for each pentamer's center base and applied genome-wide in the same way.

To order the top 200 Max-bound E-box motifs by the difference in DNA propeller twist (FIG. 5F), the mean propeller twist was calculated for the six base pairs immediately to the left and right of the motif. The motifs were then ordered by the difference between right and left mean propeller twist.

Data and Analysis Access

The ChIP-seq, ChIP-nexus and Peconic ChIP-exo datasets have been deposited to the Gene Expression Omnibus under accession number GSE55306. All analysis code used for data processing and figure generation is available via GitHub at github.com/zeitlingerlab.

Example 6

Superior Performance and Precise Identification of Known In Vivo Binding Sites

To compare the ChIP-nexus protocol to the original ChIP-exo protocol, the occupancy of TBP in human K562 cells was mapped. This was done previously with a ChIP-exo protocol adapted to Illumina sequencing (Venters et al., 2013). TBP ChIP-nexus experiments were conducted with the same amount of K562 cells and the same TBP antibody, and raw data of the stop bases on each strand was then compared with those of the published dataset. As seen at the RPS12 gene (FIG. 2A), which Venters et al. presented (Id.), as well as the AMD1 promoter (FIG. 2B), which also has prominent TBP ChIP-seq signal, ChIP-nexus produced visibly better results. The previous ChIP-exo data show signs of over-amplification since the reads often occur in extremely high numbers at the same position without any reads at neighboring positions. In contrast, ChIP-nexus produces signal across the entire promoter region in a pattern that is similar across genes. Such a pattern is observed with regular ChIP-exo data only after averaging across many genes (Id.). Thus, while the overall pattern is comparable to ChIP-exo, ChIP-nexus produces high-quality data that can be analyzed at the single-gene level.

Next, transcription factors in the early Drosophila embryo were mapped as the many very well characterized enhancers allowed assessment of the ChIP-nexus method in light of more traditional techniques. One of the best-studied transcriptional regulatory networks is dorso-ventral patterning, which is controlled by an activity gradient of Dorsal, the homologue of the vertebrate transcription factor NFkB. Dorsal induces the rhomboid (rho) gene in the neuroectoderm by binding and activating an extensively characterized upstream enhancer (rho NEE) (Fakhouri et al., 2010, Ip et al., 1991, Zinzen et al., 2006). In vitro footprinting revealed four Dorsal sites in the rho NEE enhancer (d1-d4). Mutation of d2, d3, and d4 almost completely abolishes the enhancer activity (Ip et al., 1992) and d3 plays the most important role in computer models of its activity (Fakhouri et al., 2010). Indeed, a strong Dorsal binding footprint was found, with prominent peaks at both strands directly over the d3 binding site (FIG. 2C). Less prominent Dorsal footprints were found on d1 and d2, while no footprint was found on d4, consistent with previous findings that not all binding sites in vitro are necessarily bound in vivo (Liu et al., 2006). Indeed, d3 is likely to be the most important Dorsal binding site due to its proximity to two E-box motifs (Fakhouri et al., 2010; Szymanski et al., 1995). Both E-boxes can be bound by the basic helix-loop-helix (bHLH) transcription factor Twist in vitro (Ip et al., 1992) and are important for enhancer activity in vivo (Ip et al., 1992; Ozdemir et al., 2011). We, therefore, tested whether ChIP-nexus with Twist would identify these two binding sites. Indeed, prominent ChIP-nexus footprints of Twist were found exactly over the two known binding sites next to the d3 Dorsal site (FIG. 2E).

In contrast with these clear results, when Peconic LLC performed a ChIP-exo experiment based on the original protocol, the results did not show any clear footprint at this enhancer (FIG. 2C). This may be in part because Peconic used SOLiD sequencing, which results in much lower read counts than Illumina sequencing. However, while the reduced quality of the Dorsal experiment is in part because of the lower read number obtained (FIGS. 2C and 2D), even the Twist ChIP-exo experiment, which had comparable read counts to our ChIP-nexus data, shows a less precise footprint (FIG. 2E), supporting our conclusion that ChIP-nexus produces better results at the single-gene level.

Figure 3:
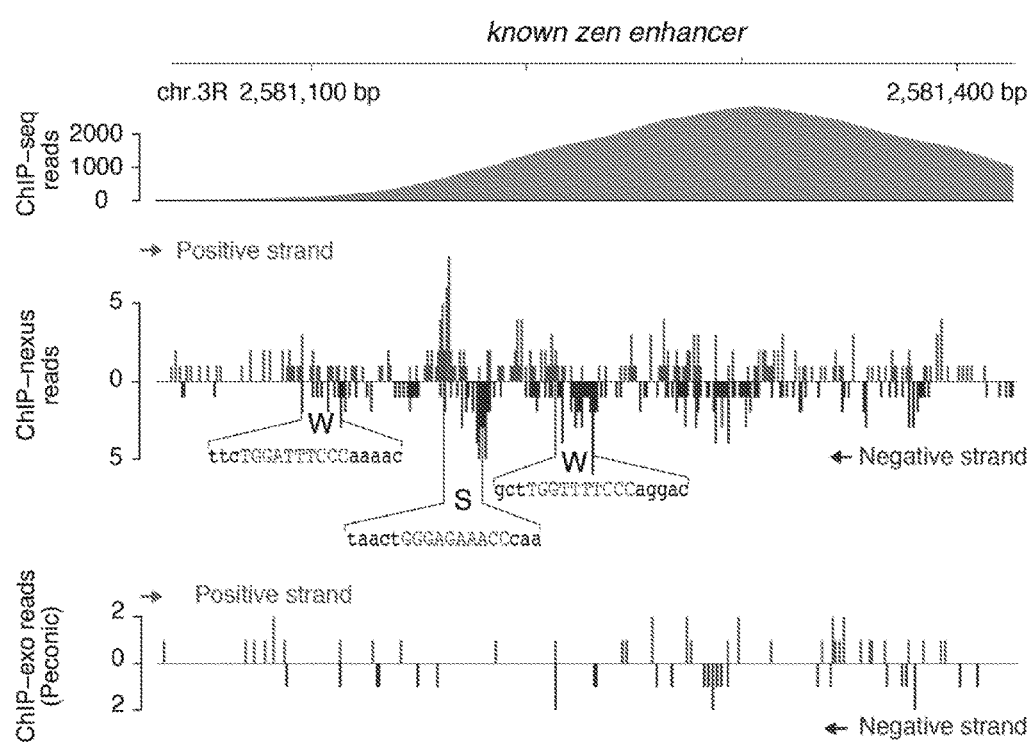
FIG. 3 shows Dorsal ChIP-nexus profile at *D. melanogaster* zen enhancer. Three dorsal binding sites (S: strong; W: weak) were mapped previously by in vitro footprinting (Ip et al., 1991). The strong site mapped was also revealed by ChIP-nexus as the strongest site among them.

Dorsal binding was also analyzed at the known intronic decapentaplegic (dpp) enhancer (FIG. 2D), as well as the upstream enhancer of zen (FIG. 3). Both enhancers mediate repression on the ventral side of the embryo. By in vitro footprinting, several strong Dorsal binding sites had been identified in the dpp enhancer and simultaneous mutation of two of them (S3 and S4) abolished ventral repression (Huang et al., 1993). The ChIP-nexus data show a clear footprint of Dorsal at the previously mapped S4 binding site, but not at other mapped Dorsal sites (FIG. 2D). Also, the boundaries of the footprint extend beyond the NFkB consensus motif, similar to the DNase footprints in vitro. In contrast, the Peconic ChIP-exo data did not show identifiable footprints. Likewise, at the zen enhancer, ChIP-nexus, but not ChIP-exo, identifies a clear footprint of the expected size at the strongest in vitro footprint (FIG. 3). Taken together, ChIP-nexus binding of Dorsal at the most important characterized binding sites was confirmed, demonstrating that ChIP-nexus can successfully pinpoint critical binding sites within an enhancer.

Example 7

Characterization of the NFkB and Max Binding Footprints

Figure 4:
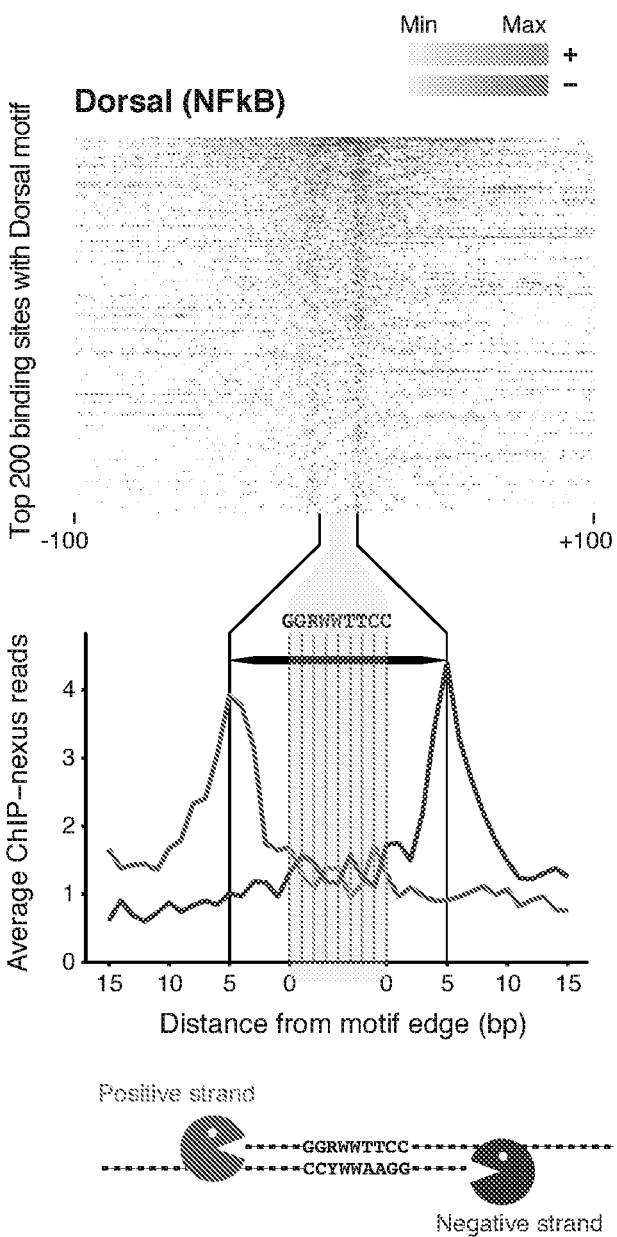
FIG. 4 shows analysis of the NFkB and Max in vivo footprint.

Since NFkB is a well-studied transcription factor, the binding profile of the Dorsal footprint was examined next. For this, the average profile from the 200 Dorsal motifs (GGRWWTTCC) with the highest ChIP-nexus counts was calculated (FIG. 4A). It looks very similar to the footprints on known Dorsal targets, with the boundaries located five nucleotides upstream of the motif. This is consistent with the crystal structure of NFkB, which also suggests that the footprint is wider than the binding sequence (Chen et al., 1998), but whether lambda exonuclease stops exactly at the protein-DNA boundary or perhaps a few nucleotides before remains unclear.

To analyze another well-studied transcription factor, ChIP-nexus was performed on Max in Drosophila S2 cells (FIG. 4B). Max is a basic helix-loop-helix (bHLH) transcription factor that binds to the palindromic E-box motif CACGTG either as homodimer or as heterodimer with other bHLH proteins such as Myc (Blackwood et al., 1991, Prendergast et al., 1991). The average footprint at the motif showed clear boundaries located 8 bp upstream of the motif (FIG. 4B). This indicates protection by Max on flanking DNA sequences that could not be observed in the crystal structure of Max-Max, Max-Myc and Max-Mad, which only included 6 base pairs flanking either side of the E-box motif and did not use full-length Max or Myc (Nair et al., 2003, Ferre-D'Amare et al., 1993). However, in vitro footprinting assays of Max and Myc show protection of 4-6 bases beyond the motif (Wechsler et al., 1994, Walhout et al., 1997), consistent with the results disclosed herein.

Example 8

The Asymmetric Binding Profile of Max

The Max profile showed high read counts at two positions within the motif (middle peaks), in addition to the outside footprint boundaries (outside peaks) (FIG. 4B). This was unexpected since it suggests that lambda exonuclease can in many cases digest through half of the footprint. Inspection of the footprints at individual genes confirmed the frequent asymmetry of the Max footprint. This asymmetry might explain why the reads from regular ChIP-seq experiments often do not peak over the motif (FIGS. 4C, 4D). To understand this asymmetry, the Max profile was analyzed in more detail.

First, whether Max binding might differ between different E-box variants (CANNTG) was tested (FIG. 4E). For each possible middle sequence, 200 motifs with the highest ChIP-nexus read counts were selected. As expected, the binding was most prominent at the canonical CACGTG motif. A smaller but otherwise identical footprint was observed at the CACATG motif, and none of the other E-box variants showed significant binding. These results are in agreement with the binding specificity of Max in vitro (Nair et al., 2003, Orian et al., 2003) and suggest that the shape of the Max footprint does not depend on the E-box motif.

Next we analyzed the ChIP-nexus footprint of Twist over the known binding motifs (CABATG, thus CATATG, CACATG or CAGATG). We found that Twist has two boundaries, one located 11 nucleotides and another one two nucleotides upstream of the motif (FIG. 4F), indicating interactions between Twist and the DNA flanking sequences outside the binding motif. We next tested whether the binding footprint of Twist varies across E-box variants of the pattern CANNTG (FIG. 4G). Consistent with previous data (Ozdemir et al., 2011; Zhu et al., 2011), Twist binding occurred at multiple E-boxes (FIG. 4G). But the shapes of these footprints varied in that the outer boundary (at 11 bp from the motif) was dominant at the CATATG motif and to a lesser extent the CACATG motif, the two motifs with the highest evolutionary conservation across *Drosophila* species 17. In contrast, the inner boundary (at 2 bp from the motif) was more prominent at the CAGATG motif. Although the basis for these differences in footprints is unknown, the results may indicate an unappreciated specificity in the way transcription factors are detected in vivo.

Second, whether binding to a half site might reflect the binding of Max as a heterodimer with its partner Myc was tested. To do this, the 200 Max binding footprints were computationally oriented such that the higher read counts were oriented to the right of the CACGTG motif (FIG. 5A). ChIP-nexus was then performed with Myc and investigated as to whether Myc footprints follow the opposite trend at these Max sites, i.e. whether the higher signal would be found to the left of the motif. Although there are subtle differences between the profiles, the Myc profile was also oriented to the right, similar to the Max profile (FIG. 5B). The only minor difference between heterodimeric partners is consistent with the fact that formaldehyde efficiently cross-links protein-protein interactions (Orlando et al., 2000), which predicts that heterodimeric partners are frequently co-detected in ChIP experiments. Taken together, these results suggest that both Max and Myc footprints are preferentially located on one side of the E-box motif, which is referred to herein as the favored interaction side.

Example 9

DNA Shape Predicts the Favored Interaction Side

Figure 6:
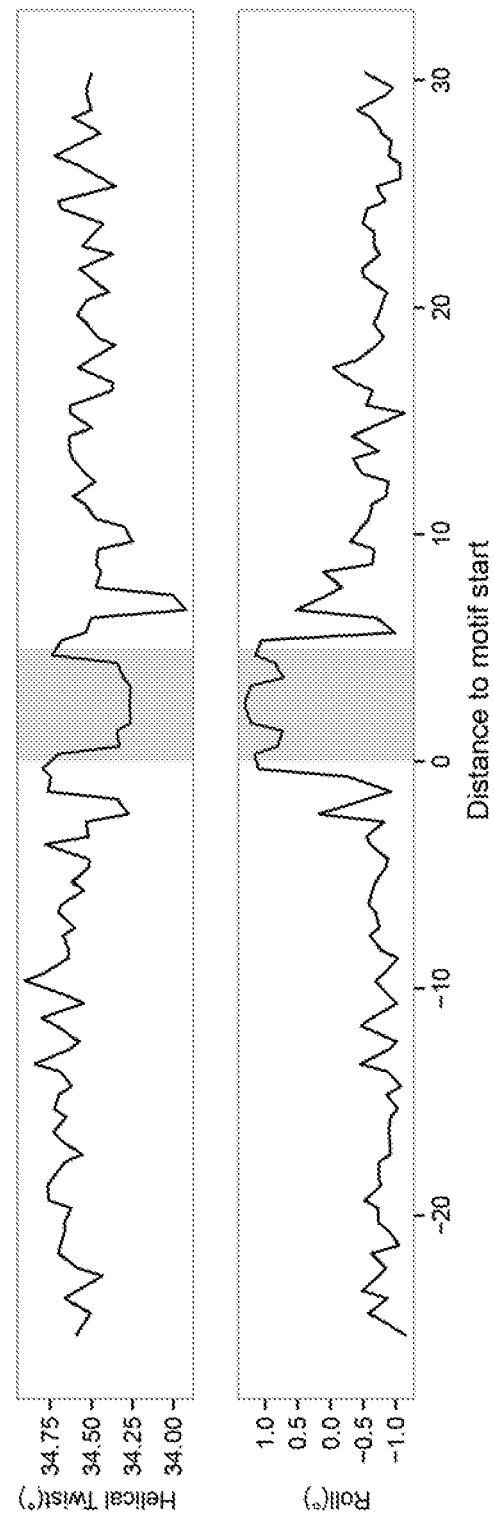
FIG. 6 shows additional DNA shape characteristics around Max-bound motifs. Two additional DNA shape characteristics, helical twist and roll (both measured in degrees), show differences between the preferred interaction side of Max-bound motifs (left of the gray box) and the less favored interaction side (right of the gray box), similar to the minor groove width and propeller twist predictions shown in FIGS. 5D and 5E. Predicted DNA shape characteristics were obtained using the DNAshape web service (Zhou et al., 2013).

Next, it was asked what features of the sequences flanking the Max motif may predict the favored interaction side of Max. We found that the base composition shows significant biases next to the E-box, which creates a directional motif of the consensus RCACGTGYTG. Analysis of the base composition showed that G was more prevalent on the favored interaction side at the third position from the motif, while A was more prevalent on the less favored side (FIG. 5C). Next, whether DNA shape could explain the orientation of the Max binding footprint was tested. The specificity of bHLH factors has previously been shown to correlate with parameters of the DNA shape in flanking sequences (Gordan et al., 2013). It was found that the propeller twist, a measurement for the relative rotation between two base pairs, is significantly closer to 0 degrees at the favored interaction side and is on average significantly stronger at the less favored interaction side (FIG. 5D, paired t-test $p<10^{-21}$). The minor groove is also slightly larger in this region (FIG. 5E), and the base pair roll and helical twist also show subtle differences (FIG. 6). To visualize the correlation between propeller twist and favored interaction side, the 200 Max footprints were sorted based on the difference in propeller twist between the two sides and the Max footprint was then plotted in the same order (FIG. 5F). This shows that a strong asymmetry with regard to the propeller twist is an excellent predictor for the favored interaction side.

Example 10

Additional Comparison of ChIP-Nexus and ChIP-Seq

Figure 7:
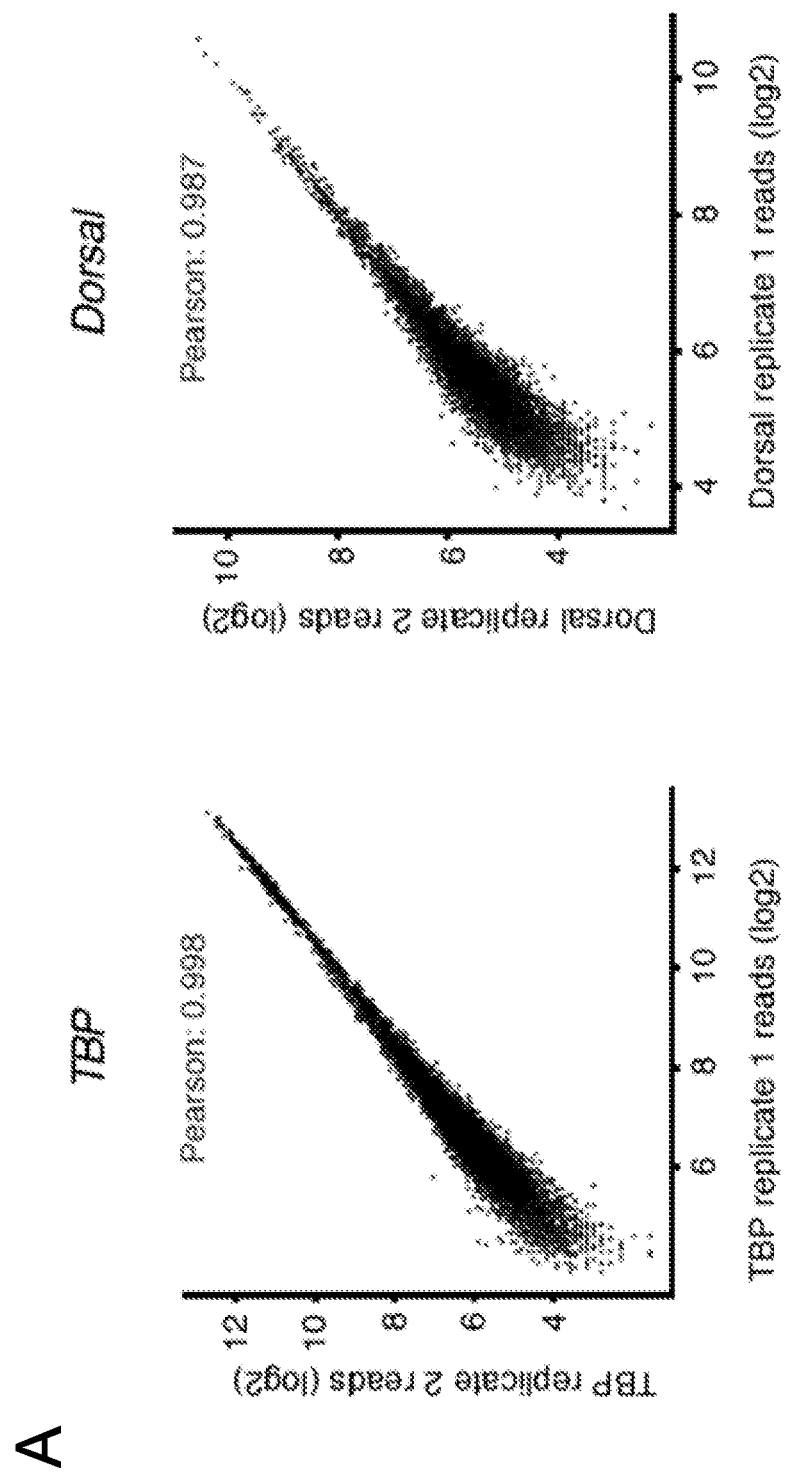
FIG. 7 shows high reproducibility, resolution and specificity of ChIP-nexus as compared to ChIP-seq.

We next analyzed the relationship between ChIP-nexus and ChIP-seq signal. The Pearson correlation of the reads was lower than between replicates but still very high (FIG. 7B, TBP 0.85, Dorsal 0.59). Scatterplots confirm that the bulk signal is similar between ChIP-nexus and ChIP-seq signal but that many bound regions have higher signal in the ChIP-nexus data (FIG. 7B). Regions with higher ChIP-nexus/ChIP-seq ratio include many known Dorsal enhancers (e.g. rho NEE, dpp, zen, vnd, vn), while regions with lower ChIP-nexus/ChIP-seq signal often lack a specific footprint, indicating that they may be enriched through unspecific binding to open chromatin. For instance, the dpp promoter shows high Dorsal ChIP-seq enrichments comparable to the known dpp enhancer, but has no specific footprint in the ChIP-nexus data (FIG. 7C).

To test more systematically whether ChIP-nexus indeed has increased specificity and resolution compared to ChIP-seq, we analyzed the presence and location of consensus binding motifs within peaks (FIG. 7C, 7D). Among the top 200 Dorsal and Twist ChIP-nexus binding peaks, the corresponding consensus motif was found directly at the center of the ChIP-nexus binding peaks much more frequently than at the ChIP-seq binding peaks (FIG. 7D), underscoring the increased resolution. Indeed, within 10 bp of the peak summit, there was a significant improvement in motif enrichment in the ChIP-nexus data compared to the ChIP-seq data (Chi$^2$ test, Dorsal $p<10^{-10}$, Twist $p<10^{-22}$, FIG. 7E). Yet even at 100 bp from the summit, ChIP-nexus still had significantly higher motif enrichment than ChIP-seq (Chi$^2$ test, Dorsal $p<10^{-3}$, Twist $p<10^{-10}$, FIG. 7E), supporting the notion that ChIP-nexus not only has improved resolution but also improved specificity.

ChIP-nexus was found to be a robust protocol to map the in vivo binding footprints of transcription factors genome-wide. The increased resolution compared to regular ChIP-seq and the increased robustness compared to ChIP-exo provides an unprecedented view on the in vivo binding landscape of transcription factors. While ChIP-seq experiments are excellent at identifying cis-regulatory regions, ChIP-nexus utilizes a similar amount of cells but pinpoints more precisely relevant binding sites within individual enhancers and provides information on how different motif variants are bound in vivo. Although high-resolution in vivo binding data can also be obtained by digital genomic footprinting (Hesselberth et al., 2009), this requires substantially more sequencing depth and does not reveal the identity of the bound transcription factors. Also, it is noted that only some bioinformatics packages can currently handle high-resolution ChIP-nexus data (Bardet et al., 2013, Venters et al., 2013, Rhee et al., 2011). However, with further development of analysis tools, ChIP-nexus has the potential to replace routine ChIP-seq experiments.

The increased resolution shows a surprising asymmetric footprint of Max, indicating that sequences flanking E-box motifs may make additional contacts with Max and hence influence binding affinity. This asymmetric interaction can be predicted by parameters of DNA shape in the flanking sequences. While the possibility cannot be excluded that the favored side is the preferred side of cross-linking by formaldehyde, it is unlikely that this is the only explanation. It is becoming more and more evident that local DNA features around a motif contribute to the specificity of protein-DNA interactions, whether measured in vitro without formaldehyde cross-linking (Gordan et al., 2013) or in vivo using reporter assays (White et al., 2013). Furthermore, there is no evidence that formaldehyde would better cross-link at bases with a neutral propeller twist (cross-linking may be preferred at open of Hoogsteen base pairs (Bohnuud et al., 2012)). Thus, it is possible that Max and Myc indeed have a favored interaction side in vivo.

The high resolution and robustness of the protocol opens the possibility for a much more extended analysis of the in vivo binding site specificity of transcription factors. For example, ChIP-nexus is ideally suited for identification of single nucleotide polymorphisms (SNPs) that alter transcription factor binding, either across species or between individuals within a population. Furthermore, since it precisely identifies which binding motif is bound in vivo, it will help in identifying the influence of nucleosomes, other transcription factors or DNA methylation on the in vivo binding of transcription factors. Therefore, ChIP-nexus could become an invaluable tool for untangling the mechanisms of combinatorial regulation.

DOCUMENTS

ARNOLD, T. and Linke, D. 2008. The Use of Detergents to Purify Membrane Proteins. Current Protocols in Protein Science. 53:4.8.1-4.8.30.

BARDET, A. F. et al. Identification of transcription factor binding sites from ChIP-seq data at high resolution. *Bioinformatics* 29, 2705-2713 (2013).

BLACKWOOD, E. M. et al. Max: a helix-loop-helix zipper protein that forms a sequence-specific DNA-binding complex with Myc. *Science* 251, 1211-1217 (1991).

BOHNUUD, T. et al. Computational mapping reveals dramatic effect of Hoogsteen breathing on duplex DNA reactivity with formaldehyde. *Nucleic Acids Research* 40, 7644-7652 (2012).

BONIFACINO, et al. 2001. Immunoprecipitation. Current Protocols in Immunology. 41:8.3.1-8.3.28.

BYSTRYKH L V (2012) Generalized DNA Barcode Design Based on Hamming Codes. PLoS ONE 7(5): e36852. doi:10.1371/journal.pone.0036852

CASBON, J. A. et al. A method for counting PCR template molecules with application to next-generation sequencing. *Nucleic Acids Research* 39, e81 (2011).

CHEN, F. E. et al. Crystal structure of p50/p65 heterodimer of transcription factor NF-kappaB bound to DNA. *Nature* 391, 410-413 (1998).

EVANS, T. C. and Nichols, N. M. 2008. DNA Repair Enzymes. Current Protocols in Molecular Biology. 84:3.9.1-3.9.12.

FAKHOURI, W. D. et al. Deciphering a transcriptional regulatory code: modeling short-range repression in the *Drosophila* embryo. *Mol Syst Biol* 6, 341 (2010).

FENG, J., Liu, T., Qin, B., Zhang, Y. & Liu, X. S. Identifying ChIP-seq enrichment using MACS. *Nat Protoc* 7, 1728-1740 (2012).

FERRE-D'AMARE, A. R. et al. Recognition by Max of its cognate DNA through a dimeric b/HLH/Z domain. *Nature* 363, 38-45 (1993).

GENTLEMAN, R. C. et al. Bioconductor: open software development for computational biology and bioinformatics. *Genome Biology* 5, R80 (2004).

GORDAN, R. et al. Genomic regions flanking E-box binding sites influence DNA binding specificity of bHLH transcription factors through DNA shape. *Cell Rep* 3, 1093-1104 (2013).

HE, Q. et al. High conservation of transcriptional factor binding and evidence for combinatorial regulation across six *Drosophila* species. *Nature Genetics* 43, 414-420 (2011).

HESSELBERTH, J. R. et al. Global mapping of protein-DNA interactions in vivo by digital genomic footprinting. *Nat Methods* 6, 283-289 (2009).

HUANG, J. D. et al. The interplay between multiple enhancer and silencer elements defines the pattern of decapentaplegic expression. *Genes & Development* 7, 694-704 (1993).

IP, Y. T. et al. The dorsal gradient morphogen regulates strips of rhomboid expression in the presumptive neuroectoderm of the *Drosophila* embryo. *Genes & Development* 6, 1728-1739 (1992).

IP, Y. T. et al. The dorsal morphogen is a sequence-specific DNA-binding protein that interacts with a long-range repression element in *Drosophila*. *Cell* 64, 439-446 (1991).

KIVIOJA, T. et al. Counting absolute numbers of molecules using unique molecular identifiers. *Nat Methods* 9, 72-74 (2012).

KONIG, J. et al. iCLIP reveals the function of hnRNP particles in splicing at individual nucleotide resolution. *Nat Struct Mol Biol* 17, 909-915 (2010).

LANGMEAD, B. et al. Ultrafast and memory-efficient alignment of short DNA sequences to the human genome. *Genome Biology* 10, R25 (2009).

LI, H. et al. The sequence alignment/Map format and SAMtools. *Bioinformatics* 25, 2078-2079 (2009).

LIU, X. et al. Whole-genome comparison of Leu3 binding in vitro and in vivo reveals the importance of nucleosome occupancy in target site selection. *Genome Research* 16, 1517-1528 (2006).

MARTIN, M. Cutadapt removes adaptor sequences from high-throughput sequencing reads. *EMBnet.journal* 17, 3 (2011).

MIR, Katharina, et al. "Short Barcodes for Next Generation Sequencing." PLoS one 8.12 (2013): e82933.

NAIR, S. K. et al. X-ray structures of Myc-Max and Mad-Max recognizing DNA. Molecular bases of regulation by proto-oncogenic transcription factors. *Cell* 112, 193-205 (2003).

ORIAN, A. et al. Genomic binding by the *Drosophila* Myc, Max, Mad/Mnt transcription factor network. *Genes & Development* 17, 1101-1114 (2003).

ORLANDO, V. Mapping chromosomal proteins in vivo by formaldehyde-crosslinked-chromatin immunoprecipitation. *Trend Biochem Sci* 25, 99-104 (2000).

Ozdemir, A. et al. High resolution mapping of Twist to DNA in *Drosophila* embryos: Efficient functional analysis and evolutionary conservation. *Genome Res* 21, 566-577 (2011).

PRENDERGAST, G. C. et al. Association of Myn, the murine homolog of max with c-Myc stimulates methylation-sensitive DNA binding and ras cotransformation. *Cell* 65, 395-407 (1991).

R CORE TEAM. R: A language and environment for statistical computing. (2013).

RHEE, H. S. et al. ChIP-exo method for identifying genomic location of DNA-binding proteins with near-single-nucleotide accuracy. *Curr Protoc Mol Biol Chapter* 21, Unit 21 24 (2012b).

RHEE, H. S. et al. Comprehensive genome-wide protein-DNA interactions detected at single-nucleotide resolution. *Cell* 147, 1408-1419 (2011).

RHEE, H. S. et al. Genome-wide structure and organization of eukaryotic pre-initiation complexes. *Nature* 483, 295-301 (2012a).

SANDMANN, T et al. A core transcriptional network for early mesoderm development in *Drosophila melanogaster*. *Genes & Development* 21, 436-449 (2007).

SERANDOUR, A. A. et al. Development of an Illumina-based ChIP-exonuclease method provides insight into FoxA1-DNA binding properties. *Genome Biology* 14, R147 (2013).

SPITZ, F. et al. Transcription factors: from enhancer binding to developmental control. *Nat Rev Genet* 13, 613-626 (2012).

Szymanski, P. & Levine, M. Multiple modes of dorsal-bHLH transcriptional synergy in the *Drosophila* embryo. *Embo J* 14, 2229-2238 (1995).

THOMPSON, J. F. and Steinmann, K. E. 2010. Single Molecule Sequencing with a HeliScope Genetic Analysis System. Current Protocols in Molecular Biology. 92:7.10.1-7.10.14.

VENTERS, B. J. et al. Genomic organization of human transcription initiation complexes. *Nature* 502, 53-58 (2013).

WALHOUT, A. J. et al. c-Myc/Max heterodimers bind cooperatively to the E-box sequences located in the first intron of the rat ornithine decarboxylase (ODC) gene. *Nucleic Acids Research* 25, 1493-1501 (1997).

WECHSLER, D. S. et al. Differential binding of c-Myc and Max to nucleosomal DNA. *Molecular and Cellular Biology* 14, 4097-4107 (1994).

WHITE, M. A. et al. Massively parallel in vivo enhancer assay reveals that highly local features determine the cis-regulatory function of ChIP-seq peaks. *PNAS* 110, 11952-11957 (2013).

ZEITLINGER, J. et al. Whole-genome ChIP-chip analysis of Dorsal, Twist, and Snail suggest integration of diverse patterning processes in the *Drosophila* embryo. *Genes & Development* 21, 385-390 (2007).

ZHOU, T. et al. DNAshape: a method for the high-throughput prediction of DNA structural features on a genomic scale. *Nucleic Acids Research* 41, W56-62 (2013).

Zhu, L. J. et al. FlyFactorSurvey: a database of *Drosophila* transcription factor binding specificities determined using the bacterial one-hybrid system. *Nucleic Acids Res* 39, D111-117 (2011).

ZINZEN, R. P. et al. Computational models for neurogenic gene expression in the *Drosophila* embryo. *Curr Biol* 16, 1358-1365 (2006).

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

---

What is claimed is:

1. A method for identifying where a polypeptide of interest binds in a genome, the method comprising:
   (a) carrying out a chromatin immunoprecipitation coupled to an exonuclease digestion (ChIP-exo) process with an antibody against the polypeptide of interest;
   (b) extracting a polynucleotide fragment to which the polypeptide of interest binds;
   (c) carrying out a library preparation protocol adapted from an individual nucleotide resolution UV cross-linking and immunoprecipitation (iCLIP) process on the ChIP-exo processed polynucleotide fragment, wherein the end of the polynucleotide fragment is ligated to an adaptor comprising two tail-to-tail primer sequences, a restriction site, and a nucleotide barcode, which barcode protrudes as a 5' end overhang to prevent ligation of the end of the polynucleotide fragment to the barcode; and
   (d) sequencing the resulting polynucleotides.

2. The method according to claim 1, wherein the polypeptide of interest is selected from the group consisting of a transcription factor, a polymerase, a nuclease, and a hi stone.

3. The method according to claim 2, wherein the polynucleotide fragment comprises a binding site for the polypeptide.

4. The method according to claim 1 further comprising, prior to step (a), cross-linking the polypeptide to a polypeptide binding site on the polynucleotide fragment with a cross-linking agent to form a reversible complex.

5. The method according to claim 4, wherein the cross-linking agent is selected from the group consisting of formaldehyde, glutaraldehyde, and acetaldehyde.

6. The method according to claim 4 wherein the ChIP-exo process comprises:
   (e) immunoprecipitating the polypeptide of interest which is cross-linked to the polynucleotide fragment using an antibody linked to a substrate;
   (f) ligating the adaptor to the end of the polynucleotide fragment, which ligating step is optionally followed by a washing step;
   (g) filling in the 5' overhang to copy the barcode and to generate blunt ends for exonuclease digestion; and
   (h) digesting the blunt-ended polynucleotide fragment from step (g) with at least one exonuclease, which terminates digestion of the polynucleotide upon encountering a physical barrier caused by the polypeptide (stop base).

7. The method according to claim 6, wherein the barcode comprises at least 4 random nucleotides.

8. The method according to claim 6, wherein the substrate is selected from the group consisting of agarose, sepharose, and magnetic agents.

9. The method according to claim 6, wherein the substrate is a Dynabead.

10. The method according to claim 6 further comprising, prior to the ligation step:
    (i) end repairing the polynucleotide fragment with DNA polymerase I, T4 DNA polymerase, T4 polynucleotide kinase, and dNTPs optionally followed by a washing step; and
    (j) dA tailing the polynucleotide fragment with a Klenow fragment and ATP optionally followed by a washing step.

11. The method according to claim 6 further comprising, prior to the exonuclease digestion step, end trimming the polynucleotide fragment by contacting it with a T4 DNA polymerase and dNTPs optionally followed by a washing step.

12. The method according to claim 6, wherein prior to the ligation step the immunoprecipitated cross-linked polypeptide-polynucleotide complex is optionally washed at least once in one or more buffers, which may be the same or different.

13. The method according to claim 6, wherein the optional washing step includes washing sequentially in one or more buffers selected from the group consisting of 10 mM Tris-EDTA buffer, Mixed Micelle buffer, Buffer 500, LiCl/Detergent buffer, and 10 mM Tris-HCl buffer.

14. The method according to claim 6, wherein the at least one exonuclease has strand-specific double-stranded-DNA-specific exonuclease activity and is selected from the group consisting of lambda exonuclease, T7 exonuclease, T5 exonuclease, exonuclease III, exonuclease II, exonuclease VIII, and CCR4.

15. The method according to claim 14, wherein step (h) further comprises washing the polynucleotide fragment after digestion with an exonuclease having strand-specific double-stranded-DNA-specific activity followed by contacting the polynucleotide fragment with an exonuclease having strand-specific single-stranded-specific exonuclease activity.

16. The method according to claim 14, wherein the exonuclease having strand-specific single-stranded-specific exonuclease activity is selected from the group consisting of RecJ$_f$ exonuclease, exonuclease I, and exonuclease VII.

17. The method according to claim 1, wherein extraction step comprises:
- (k) washing the polypeptide-polynucleotide complex from step (h) with a buffer;
- (l) eluting the polypeptide-polynucleotide complex from the substrate;
- (m) reverse cross-linking the polypeptide-polynucleotide complex;
- (n) purifying the polynucleotide;
- (o) denature the purified polynucleotide to make a single stranded polynucleotide; and
- (p) precipitating the purified single stranded polynucleotide.

18. The method according to claim 6, wherein the restriction site is selected from the group consisting of a BamHI site, an AaaI site, an AbaI site, an AbeI site, an AbrI site, an Acc113I site, an Acc16I site, an Acc36I site, an Acc65I site, an AccB1I site, an AccB2I site, an AccB7I site, an AccBSI site, an AccEBI site, an AccI site, an AccII site, an AccIII site, an AceI site, an AceII site, an AceIII site, an AciI site, an AclI site, an AclNI site, an AclWI site, an AcpI site, an AcpII site, an AcrII site, an AcsI site, an AcuI site, an AcvI site, an AcyI site, an AdeI site, an AeuI site, an Afa16RI site, an Afa22MI site, an AfaI site, an AfeI site, an AflI site, an AflII site, an AflIII site, an AgeI site, an AglI site, an AhaB8I site, an AhaI site, an AhaII site, an AhaIII site, an AhdI site, an AhlI site, an AhyI site, an AitI site, an AjnI site, an AjoI site, an AleI site, an AlfI site, an AliAJI site, an AliI site, an AloI site, an AluI site, an Alw21I site, an Alw26I site, an Alw44I site, an AlwI site, an AlwNI site, an AlwXI site, an Ama87I site, an AocI site, an AocII site, an Aor13HI site, an Aor51HI site, an AorI site, an AosI site, an AosII site, an ApaBI site, an ApaCI site, an ApaI site, an ApaLI site, an ApaORI site, an ApeKI site, an ApiI site, an ApoI site, an ApyI site, an AquI site, an AscI site, an AseI site, an AseII site, an AsiAI site, an AsiI site, an AsiSI site, an AsnI site, an Asp10HI site, an Asp10HII site, an Asp26HI site, an Asp27HI site, an Asp35HI site, an Asp36HI site, an Asp40HI site, an Asp50HI site, an Asp700I site, an Asp713I site, an Asp718I site, an Asp745I site, an AspA2I site, an AspAI site, an AspEI site, an AspHI site, an AspI site, an AspLEI site, an AspMDI site, an AspMI site, an AspNI site, an AspS9I site, an AssI site, an AstWI site, an AsuC2I site, an AsuHPI site, an AsuI site, an AsuII site, an AsuIII site, an AsuNHI site, an AtsI site, an AvaI site, an AvaII site, an AvcI site, an AviII site, an AvrBII site, an AvrII site, an AxyI site, a Bac36I site, a BaeI site, a Ba1228I site, a BalI site, a BamNxI site, a BanAI site, a BanI site, a BanII site, a BanIII site, a BasI site, a BauI site, a BavAI site, a BavAII site, a BavBI site, a BavBII site, a BavCI site, a BavI site, a BbeI site, a Bbi24I site, a BbiII site, a Bbr7I site, a BbrI site, a BbrPI site, a BbsI site, a BbuI site, a Bbv12I site, a Bbv16II site, a BbvAI site, a BbvAII site, a BbvAIII site, a BbvBI site, a BbvCI site, a BbvI site, a BbvII site, a Bca77I site, a BccI site, a Bce22I site, a Bce243I site, a Bce4I site, a Bce751I site, a Bce83I site, a BceAI site, a BceBI site, a BceCI site, a BcefI site, a BcgI site, a Bci29I site, a BciBI site, a BciBII site, a BciVI site, a BclI site, a BcmI site, a BcnI site, a Bco116I site, a Bco118I site, a Bco27I site, a Bco5I site, a BcoAI site, a BcoI site, a BcoKI site, a BcuAI site, a BcuI site, a BdiI site, a BdiSI site, a BecAII site, a BepI site, a BetI site, a BfaI site, a Bfi57I site, a Bfi89I site, a BfiI site, a BflI site, a BfmI site, a BfrBI site, a BfrI site, a BfuAI site, a BfuCI site, a BfuI site, a BglI site, a BglII site, a Bim19I site, a Bim19II site, a BimI site, a BinI site, a BlfI site, a Bli41I site, a Bli736I site, a Bli86I site, a BliAI site, a BliRI site, a BlnI site, a BloHI site, a BloHII site, a BlpI site, a BluI site, a Bme12I site, a Bme1390I site, a Bme142I site, a Bme1580I site, a Bme18I site, a Bme216I site, a Bme361I site, a Bme585I site, a BmgBI site, a BmrI site, a BmtI site, a BmyI site, a BnaI site, a BoxI site, a BpcI site, a BpiI site, a Bp1I site, a BpmI site, a BpoAI site, a BptI site, a Bpu10I site, a Bpu1102I site, a Bpu14I site, a Bpu95I site, a BpuAI site, a BpuAmI site, a BpuB5I site, a BpuDI site, a BpuEI site, a BpuI site, a BpuJI site, a BpuSI site, a Bsa29I site, a BsaAI site, a BsaBI site, a BsaHI site, a BsaI site, a BsaJI site, a BsaMI site, a BsaOI site, a BsaWI site, a BsaXI site, a Bsc107I site, a Bsc4I site, a Bsc91I site, a BscAI site, a BscBI site, a BscCI site, a BscFI site, a BscI site, a Bse118I site, a Bse15I site, a Bse16I site, a Bse17I site, a BseII site, a Bse21I site, a Bse24I site, a Bse3DI site, a Bse634I site, a Bse64I site, a Bse8I site, a BseAI site, a BseBI site, a BseCI site, a BseDI site, a BseGI site, a BseJI site, a BseKI site, a BseLI site, a BseMI site, a BseMII site, a BseNI site, a BsePI site, a BseQI site, a BseRI site, a BseSI site, a BseT10I site, a BseT9I site, a BseX3I site, a BseXI site, a BseYI site, a BseZI site, a BsgI site, a Bsh1236I site, a Bsh1285I site, a Bsh1365I site, a Bsh45I site, a BshFI site, a BshGI site, a BshI site, a BshKI site, a BshNI site, a BshTI site, a BsiBI site, a BsiCI site, a BsiEI site, a BsiHKAI site, a BsiHKCI site, a BsiI site, a BsiKI site, a BsiLI site, a BsiMI site, a BsiQI site, a BsiSI site, a BsiWI site, a BsiXI site, a BsiYI site, a BsiZI site, a Bs1FI site, a BslI site, a BsmAI site, a BsmBI site, a BsmFI site, a BsmI site, a BsmSI site, a Bso31I site, a BsoBI site, a BsoCI site, a BsoFI site, a BsoMAI site, a Bsp105I site, a Bsp106I site, a Bsp119I site, a Bsp120I site, a Bsp123I site, a Bsp1286I site, a Bsp13I site, a Bsp1407I site, a Bsp143I site, a Bsp143II site, a Bsp153AI site, a Bsp1720I site, a Bsp1894I site, a Bsp19I site, a Bsp2095I site, a Bsp211I site, a Bsp24I site, a Bsp4009I site, a Bsp423I site, a Bsp50I site, a Bsp519I site, a Bsp63I site, a Bsp67I site, a Bsp68I site, a Bsp6I site, a Bsp98I site, a BspA2I site, a BspAAI site, a BspAAII site, a BspAAIII site, a BspAI site, a BspANI site, a BspBI site, a BspBII site, a BspBRI site, a BspBS31I site, a BspCI site, a BspCNI site, a BspD6I site, a BspDI site, a BspEI site, a BspF4I site, a BspFI site, a BspHI site, a BspIS4I site, a BspJI site, a BspJII site, a BspKI site, a BspKT5I site, a BspKT6I site, a BspKT8I site, a BspLAI site, a BspLAII site, a BspLAIII site, a BspLI site, a BspLS2I site, a BspLU11I site, a BspLU11III site, a BspLU4I site, a BspM39I site, a BspM90I site, a BspMAI site, a BspMI site, a BspMII site, a BspMKI site, a BspNI site, a BspO4I site, a BspOVI site, a BspOVII site, a BspPI site, a BspR7I site, a BspRI site, a BspST5I site, a BspT104I site, a BspT107I site, a BspTI site, a BspTNI site, a BspTS514I site, a BspWI site, a BspXI site, a BspXII site, a BspZEI site, a BsrAI site, a BsrBI site, a BsrBRI site, a BsrDI site, a BsrFI site, a BsrGI site, a BsrI site, a BsrSI site, a BssAI site, a BssECI site, a BssHI site, a BssHII site, a BssIMI site, a BssKI site, a BssNAI site, a BssNI site, a BssSI site, a BssT1I site, a Bst100I site, a Bst1107I site, a Bst11I site, a Bst12I site, a Bst19I site, a Bst19II site, a Bst1I site, a Bst28I site, a Bst2BI site, a Bst2I site, a Bst2UI site, a Bst31NI site, a Bst31TI site, a Bst38I site, a Bst40I site, a Bst4CI site, a Bst6I site, a Bst71I site, a Bst98I site, a BstACI site, a BstAPI site, a BstAUI site, a BstB7SI site, a BstBAI site, a BstBI site, a BstBS32I site, a BstBSI site, a BstBZ153I site, a BstC8I site, a BstD102I site, a BstDEI site, a BstDSI site, a BstEII site, a BstENI site, a BstENII site, a BstEZ359I site, a BstF5I site, a BstFI site, a BstFNI site, a BstFZ438I site, a BstGZ53I site, a BstH2I site, a BstH9I site, a BstHHI site, a BstHPI site, a BstHZ55I site, a BstI site, a BstIZ316I site, a BstJZ301I site, a BstKTI site, a BstM6I site, a BstMAI site, a BstMBI site, a BstMCI site, a BstMWI site, a BstMZ611I site, a BstNI site, a BstNSI site, a BstNZ169I site, a BstOI site, a BstOZ616I site, a BstPAI site, a BstPI site, a BstPZ418I site, a BstPZ740I site, a BstRZ246I site, a BstSCI site, a BstSFI site, a BstSI site, a BstSNI site, a BstSWI site, a BstT10I site, a BstT7I site, a BstT9I site, a BstTS5I site, a BstUI site, a BstV1I site, a BstV2I site, a BstVI site, a BstX2I site, a BstXI site, a BstYI site, a BstZ17I site, a BstZI site, a Bsu1532I site, a Bsu15I site, a Bsu1854I site, a Bsu23I site, a Bsu36I site, a Bsu54I site, a Bsu6I site, a BsuBI site, a BsuFI site, a BsuMI site, a BsuRI site, a BsuTUI site, a BteI site, a BtgI site, a BtgZI site, a BthAI site, a BthCI site, a BthDI site, a BthEI site, a BtkI site, a BtkII site, a BtrI site, a BtsI site, a BveI site, a BvuBI site, a BvuI site, a Cac8I site, a Cad site, a CaiI site, a CauB3I site, a CauI site, a CauII site, a CbiI site, a CboI site, a CbrI site, a CciNI site, a CcoI site, a CcrI site, a CcuI site, a CcyI site, a CdiI site, a CelI site, a CelII site, a CeqI site, a CfII site, a CfoI site, a Cfr10I site, a Cfr13I site, a Cfr42I site, a Cfr6I site, a Cfr9I site, a CfrA4I site, a CfrBI site, a CfrI site, a CfrJ4I site, a CfuI site, a CfuII site, a ChaI site, a CjeI site, a CjePI site, a ClaI site, a CltI site, a CpfI site, a CpoI site, a CscI site, a CsiAI site, a CsiBI site, a Csp45I site, a Csp68KI site, a Csp68KII site, a Csp68KIII site, a Csp68KVI site, a Csp6I site, a CspAI site, a CspBI site, a CspCI site, a CspI site, a CspKVI site, a CstI site, a CstMI site, a CthII site, a CviAI site, a CviAII site, a CviBI site, a CviJI site, a CviQI site, a CviRI site, a CviRII site, a CviTI site, a CvnI site, a DdeI site, a DmaI site, a DpaI site, a DpnI site, a DpnII site, a DraI site, a DraII site, a DraIII site, a DrdI site, a DriI site, a DsaI site, a DsaII site, a DsaIII site, a DsaIV site, a DsaV site, a DseDI site, an EacI site, an Eae46I site, an EaeAI site, an EaeI site, an EagBI site, an EagI site, an EagMI site, an Eam1104I site, an Eam1105I site, an EarI site, an EcaI site, an Eci125I site, an EciI site, an Ecl136II site, an Ecl18kI site, an Ecl2zI site, an Ecl37kI site, an EclHKI site, an EclI site, an EclRI site, an EclXI site, an Eco105I site, an Eco130I site, an Eco137kI site, an Eco13kI site, an Eco147I site, an Eco1831I site, an Eco21kI site, an Eco24I site, an Eco255I site, an Eco27kI site, an Eco29kI site, an Eco31I site, an Eco32I site, an Eco47I site, an Eco47III site, an Eco52I site, an Eco53kI site, an Eco56I site, an Eco57I site, an Eco57MI site, an Eco64I site, an Eco72I site, an Eco75KI site, an Eco78I site, an Eco81I site, an Eco88I site, an Eco91I site, an EcoA4I site, an EcoHI site, an EcoHK31I site, an EcoICRI site, an EcoNI site, an EcoO109I site, an EcoO128I site, an EcoO44I site, an EcoO65I site, an EcoP15I site, an EcoR124II site, an EcoRI site, an EcoRII site, an EcoRV site, an EcoT14I site, an EcoT22I site, an EcoT38I site, an EcoVIII site, an EgeI site, an EheI site, an ErhB9I site, an ErhB9II site, an ErhI site, an ErpI site, an EsaBC3I site, an EsaBC4I site, an Esp1396I site, an Esp3I site, an Esp4I site, an EspI site, a FalI site, a FalII site, a FaqI site, a FatI site, a FauBII site, a FauI site, a FauNDI site, a FbaI site, a FblI site, a FbrI site, a FdiI site, a FdiII site, a FgoI site, a FmuI site, a Fnu4HI site, a FnuAI site, a FnuCI site, a FnuDI site, a FnuDII site, a FnuDIII site, a FnuEI site, a FokI site, a FriOI site, a FseI site, a FsiI site, a Fsp1604I site, a Fsp4HI site, a FspAI site, a FspBI site, a FspI site, a FspII site, a FspMSI site, a FssI site, a FunI site, a FunII site, a GalI site, a GceGLI site, a GceI site, a GdiI site, a GdiII site, a GstI site, a GsuI site, a Had site, a HaeI site, a HaeII site, a HaeIII site, a HaeIV site, a HalI site, a HalII site, a HapII site, a HgaI site, a HgiAI site, a HgiBI site, a HgiCI site, a HgiCII site, a HgiCIII site, a HgiDI site, a HgiDII site, a HgiEI site, a HgiGI site, a HgiHI site, a HgiHII site, a HgiHIII site, a HgiI site, a HgiJI site, a HgiJII site, a HgiS22I site, a HhaI site, a HhaII site, a HinlI site, a HinlII site, a Hin2I site, a Hin4I site, a Hin6I site, a HincII site, a HindH site, a HindIII site, a HinfI site, a HinJCI site, a HinPlI site, a HjaI site, a HpaI site, a HpaII site, a HphI site, a Hpy178III site, a Hpy188I site, a Hpy188III site, a Hpy51I site, a Hpy8I site, a Hpy99I site, a HpyAV site, a HpyBI site, a HpyBII site, a HpyCI1 site, a HpyCH4I site, a HpyCH4III site, a HpyCH4IV site, a HpyCH4V site, a HpyCI site, a HpyF10VI site, a HpyF44III site, a HsoI site, a Hsp92I site, a Hsp92II site, a HspAI site, a HsuI site, an ItaI site, a KasI site, a Kaz48kI site, a KoxII site, a Kpn2I site, a Kpn2kI site, a Kpn378I site, a Kpn49kI site, a Kpn49kII site, a KpnI site, a Ksp22I site, a Ksp632I site, a KspAI site, a KspI site, a Kzo49I site, a Kzo9I site, a LcaI site, a LlaAI site, a LlaBI site, a LlaCI site, a LlaG2I site, a Lmu60I site, a LplI site, a LpnI site, a LspI site, a LweI site, a MabI site, a MaeI site, a MaeII site, a MaeIII site, a MaeK81I site, a MaeK81II site, a MamI site, a MavI site, a MbiI site, a MboI site, a MboII site, a MchAI site, a MchAII site, a MchI site, a McrI site, a MfeI site, a MflI site, a MfoAI site, a Mgl14481I site, a MgoI site, a MhaAI site, a MhlI site, a MkrAI site, a MlaAI site, a MlaI site, a MlsI site, a MltI site, a Mlu23I site, a Mlu31I site, a MluB2I site, a MluI site, a MluNI site, a Mly113I site, a MlyI site, a MmeI site, a MnlI site, a MnoI site, a Mph1103I site, a MroI site, a MroNI site, a MroXI site, a MscI site, a MseI site, a MslI site, a Msp17I site, a Msp20I site, a Msp67I site, a MspA1I site, a MspB4I site, a MspCI site, a MspI site, a MspR9I site, a MspSWI site, a MspV281I site, a MspYI site, a MssI site, a MstI site, a MstII site, a MthZI site, a MunI site, a Mva1269I site, a MvaI site, a MvnI site, a MvrI site, a MwoI site, a MxaI site, a NaeI site, a NalI site, a NblI site, a NelI site, a NcoI site, a NcrI site, a NcuI site, a NdaI site, a NdeI site, a NdeII site, a NgoAIII site, a NgoAIV site, a NgoMIV site, a NgoPII site, a NgoPIII site, a NheI site, a NlaII site, a NlaIII site, a NlaIV site, a Nli3877I site, a NmeCI site, a NmeRI site, a NmuCI site, a NopI site, a NotI site, a NphI site, a NruGI site, a NruI site, a NsbI site, a NsiCI site, a NsiI site, a Nsp29132II site, a Nsp7121I site, a NspBII site, a NspHI site, a NspI site, a NspII site, a NspIII site, a NspIV site, a NspLKI site, a NspMACI site, a NspSAI site, a NspSAII site, a NspSAIV site, a NspV site, a NunII site, an OfoI site, an OkrAI site, an OliI site, an OxaNI site, a PabI site, a Pac25I site, a PacI site, a Pae14kI site, a Pae17kI site, a Pae18kI site, a Pae2kI site, a Pae5kI site, a PaeAI site, a PaeBI site, a PaeHI site, a PaeI site, a PaePI site, a PaeQI site, a PaeR7I site, a PagI site, a PalI site, a PamI site, a PamII site, a PanI site, a PasI site, a PauAI site, a PauAII site, a PauI site, a PeeI site, a PciI site, a PctI site, a Pde12I site, a Pde133I site, a Pde137I site, a PdiI site, a PdmI site, a PfaAI site, a PfaAII site, a PfaAIII site, a PfeI site, a Pfl21I site, a Pfl23II site, a Pfl27I site, a Pfl8I site, a PflBI site, a PflFI site, a PflKI site, a PflMI site, a PfoI site, a PgaI site, a PhaI site, a PhoI site, a PinAI site, a PinBI site, a PinBII site, a PlaAI site, a PlaAII site, a PlaI site, a PlaII site, a Ple19I site, a PleI site, a PmaCI site, a Pme55I site, a PmeI site, a PmlI site, a PovII site, a PpaAI site, a PpaAII site, a PpeI site, a PpiI site, a PpsI site, a Ppu10I site, a Ppu1 11I site, a PpuAI site, a PpuMI site, a PpuXI site, a PshAI site, a PshBI site, a PsiI site, a PspO3I site, a Psp124BI site, a Psp1406I site, a Psp23I site, a Psp5II site, a Psp6I site, a PspAI site, a PspALI site, a PspCI site, a PspEI site, a PspGI site, a PspLI site, a PspN4I site, a PspOMI site, a PspPI site, a PspPPI site, a PspXI site, a PsrI site, a PssI site, a PstI site, a PstNHI site, a Psu161I site, a PauAI site, a PsuI site, a PsyI site, a PtaI site, a Pun14627I site, a Pun14627II site, a PunAI site, a PunAII site, a Pvu84II site, a PvuI site, a PvuII site, a RalF40I site, a ReaI site, a RflFI site, a RflFII site, a R1eAI site, a RmaI site, a Rme21I site, a RsaI site, a RshI site, a RspLKI site, a RspLKII site, a RspXI site, a Rsr2I site, a RsrI site, a RsrII site, a Rtr63I site, a RtrI site, a SacI site, a SacII site, a SacNI site, a SalI site, a SalPI site, a SanDI site, a SapI site, a SarI site, a SatI site, a Sau3239I site, a Sau3AI site, a Sau96I site, a SauBMKI site, a SauHPI site, a SauI site, a SauLPI site, a SauLPII site, a SauMI site, a SauNI site, a SauSI site, a SbfI site, a Sbi68I site, a Sbo13I site, a SbvI site, a SeaI site, a SceIII site, a SchI site, a SchZI site, a SciI site, a SciNI site, a ScrFI site, a SdaI site, a SdiI site, a SduI site, a SecI site, a SelI site, a SenPT14bI site, a SenPT16I site, a SepI site, a SexAI site, a SexBI site, a SexCI site, a SfaI site, a SfaNI site, a SfcI site, a SfeI site, a SfiI site, a SflI site, a SfoI site, a Sfr274I site, a Sfr303I site, a SfuI site, a SgfI site, a SgrAI site, a SgrBI site, a SimI site, a SinI site, a SlaI site, a SleI site, a Slu1777I site, a SmaI site, a SmiI site, a SmiMI site, a SmlI site, a SmuEI site, a SmuI site, a SnaBI site, a SniI site, a SnoI site, a Sol10179I site, a SolI site, a SpaHI site, a SpeI site, a SphI site, a SplI site, a SpmI site, a SpoI site, a SpuI site, a SrfI site, a Sr132DII site, a Sr155DI site, a Sr156DI site, a Sr15DI site, a SrlI site, a Sru30DI site, a Sru4DI site, a SruI site, a SsbI site, a SscL1I site, a Sse1825I site, a Sse232I site, a Sse8387I site, a Sse8647I site, a Sse9I site, a SseAI site, a SseBI site, a SshAI site, a SsiAI site, a SsiBI site, a SsiI site, a SslI site, a SsoI site, a SsoII site, a SspII site, a Ssp27144I site, a Ssp4800I site, a Ssp5230I site, a SspAI site, a SspBI site, a SspCI site, a SspD5I site, a SspD5II site, a SspI site, a SspRFI site, a SsrI site, a Sst12I site, a SstI site, a SstII site, a SteI site, a Sth117I site, a Sth132I site, a Sth134I site, a Sth368I site, a SthI site, a StrI site, a StsI site, a StuI site, a StyD4I site, a StyI site, a SuaI site, a SuiI site, a SunI site, a SurI site, a SviI site, a SwaI site, a TaaI site, a TaiI site, a Taq52I site, a TaqI site, a TaqII site, a TaqXI site, a TasI site, a TatI site, a TauI site, a TelI site, a TfiI site, a ThaI site, a TliI site, a TruII site, a Tru201I site, a Tru9I site, a TscI site, a TseI site, a Tsp1I site, a Tsp32I site, a Tsp32II site, a Tsp45I site, a Tsp49I site, a Tsp4CI site, a Tsp509I site, a Tsp8EI site, a TspBI site, a TspDTI site, a TspEI site, a TspGWI site, a TspMI site, a TspRI site, a Tth111I site, a Tth111II site, a TthHB8I site, an Uba153AI site, an Uba4009I site, an UbaM39I site, an UnbI site, an Uur960I site, a Van91I site, a Vha464I site, a VneI site, a VpaK11AI site, a VpaK11BI site, a VpaK32I site, a VspI site, a XagI site, a XapI site, a XbaI site, a XcaI site, a XceI site, a XciI site, a XcmI site, a XcyI site, a XhoI site, a XhoII site, a XmaCI site, a XmaI site, a XmaIII site, a XmaJI site, a XmiI site, a XmnI site, a XorII site, a XpaI site, a XspI site, a YenI site, a ZanI site, a ZhoI site, a ZraI site, a ZrmI site, and a Zsp2I site.

19. The method according to claim 17, wherein the library preparation protocol adapted from the iCLIP process comprises:

(q) self-circularizing the purified single-stranded polynucleotide to place the barcode adjacent to the stop base;

(r) contacting the circularized polynucleotide from step (q) with (1) an oligonucleotide designed to produce localized double-stranded DNA around the restriction site in the adaptor and (2) a restriction enzyme that recognizes and cleaves the circularized polynucleotide at the restriction site in the adaptor to re-linearize the polynucleotide fragment, wherein upon relinearization the polynucleotide fragment comprises a primer sequence at each end; and (s) amplifying the polynucleotide sequence to an extent sufficient for sequencing.

20. The method according to claim 19, wherein the self-circularizing step comprises contacting the isolated and purified polynucleotide fragment produced by the ChIP-exo process with CircLigase under conditions and for a period of time sufficient for the polynucleotide fragment to self-circularize.

21. The method according to claim 19, wherein the oligonucleotide from step (r)(1) is complementary to the restriction site and is contacted with the circularized polynucleotide fragment under conditions and for a period of time sufficient for the oligonucleotide to bind to the restriction site.

22. The method according to claim 19 further comprising, after the restriction enzyme digestion of step (r)(2), precipitating the linearized polynucleotide fragment.

23. The method according to claim 19, wherein the amplifying step comprises carrying out PCR amplification of the linearized polynucleotide fragment.

24. The method according to claim 19 further comprising, after the amplification step, removing any adaptor dimers from the linearized polynucleotide fragment.

25. The method according to claim 19, wherein the sequencing step comprises sequencing the amplified linearized polynucleotide fragment including the barcode and the polynucleotide fragment using a sequencing primer for at least 50 cycles of extension.

26. The method according to claim 25 further comprising mapping the stop bases and their strand orientation to the genome.

27. A method for identifying where a polypeptide of interest binds in a genome, the method comprising:

(a) immunoprecipitating the polypeptide of interest which is cross-linked to a polynucleotide fragment using an antibody linked to a substrate;

(b) ligating an adaptor to the polynucleotide fragment, which adaptor comprises two tail-to-tail primer sequences, a restriction site, and a nucleotide barcode, which barcode protrudes as a 5' end overhang to prevent ligation to the barcode optionally followed by a washing step;

(c) filling in the 5' overhang to copy the barcode and generate blunt ends for exonuclease digestion;

(d) digesting the blunt-ended polynucleotide fragment from step (c) with an exonuclease, which terminates digestion of the polynucleotide upon encountering a physical barrier caused by the polypeptide (stop base);

(e) extracting the polynucleotide fragment produced by the exonuclease digestion from step (d) and purifying a single-stranded polynucleotide;

(f) self-circularizing the single-stranded polynucleotide from step (e) to place the barcode adjacent to the stop base;

(g) contacting the circularized polynucleotide with (1) an oligonucleotide designed to produce localized double-stranded DNA around the restriction site in the adaptor and (2) a restriction enzyme that recognizes and cleaves the circularized polynucleotide at the restriction site in the adaptor to re-linearize the polynucleotide fragment, wherein upon relinearization the polynucleotide fragment comprises a primer sequence at each end; and (h) amplifying the polynucleotide sequence to an extent sufficient for sequencing.

28. The method according to claim 27 further comprising sequencing the amplified linearized polynucleotide fragment including the barcode and the polynucleotide fragment using the primer for at least 50 cycles of extension.

* * * * *